(12) United States Patent
Beaulieu et al.

(10) Patent No.: US 7,241,801 B2
(45) Date of Patent: Jul. 10, 2007

(54) VIRAL POLYMERASE INHIBITORS

(75) Inventors: Pierre Beaulieu, Rosemeré (CA); Christian Brochu, Blainville (CA); Stephen Kawai, Côte St-Luc (CA); Jean Rancourt, Laval (CA); Timothy A. Stammers, Rosemeére (CA); Bounkham Thavonekham, Longueuil (CA); Youla S. Tsantrizos, St-Laurent (CA)

(73) Assignee: Boehringer Ingelheim International GmbH, Ingelheim (DE)

( * ) Notice: Subject to any disclaimer, the term of this patent is extended or adjusted under 35 U.S.C. 154(b) by 173 days.

(21) Appl. No.: 11/182,987

(22) Filed: Jul. 15, 2005

(65) Prior Publication Data

US 2006/0052418 A1    Mar. 9, 2006

Related U.S. Application Data

(60) Provisional application No. 60/588,670, filed on Jul. 16, 2004.

(51) Int. Cl.
| | |
|---|---|
| *A61K 31/404* | (2006.01) |
| *A61K 31/4155* | (2006.01) |
| *A61K 31/427* | (2006.01) |
| *A61K 31/4427* | (2006.01) |
| *A61K 31/497* | (2006.01) |
| *C07D 209/12* | (2006.01) |
| *C07D 209/14* | (2006.01) |

(52) U.S. Cl. .................. 514/419; 514/365; 514/406; 514/255.04; 514/256; 514/339; 548/491; 548/204; 548/205; 548/356.1; 546/278.1; 544/333; 544/405

(58) Field of Classification Search ............... 548/491, 548/204, 205, 356.1; 546/278.1; 544/333, 544/405; 514/419, 365, 255.04, 256, 339, 514/406

See application file for complete search history.

(56) References Cited

U.S. PATENT DOCUMENTS

| | | |
|---|---|---|
| 6,448,281 B1 | 9/2002 | Beaulieu et al. |
| 6,479,508 B1 | 11/2002 | Beaulieu et al. |
| 6,794,404 B2 | 9/2004 | Beaulieu et al. |
| 6,841,566 B2 | 1/2005 | Beaulieu et al. |
| 7,141,574 B2 | 11/2006 | Beaulieu et al. |
| 7,157,486 B2 * | 1/2007 | Beaulieu et al. ............ 514/415 |
| 2003/0176433 A1 | 9/2003 | Beaulieu, et al. |
| 2004/0110126 A1 | 6/2004 | Kukolj, et al. |
| 2004/0171626 A1 | 9/2004 | Beaulieu et al. |
| 2004/0224955 A1 | 11/2004 | Beaulieu, et al. |

FOREIGN PATENT DOCUMENTS

| | | |
|---|---|---|
| CA | 2 412 718 A1 | 1/2002 |
| CA | 2 448 737 A1 | 1/2003 |
| CA | 2 449 180 A1 | 2/2003 |
| WO | WO 2004/065367 A1 | 8/2004 |

OTHER PUBLICATIONS

Kolykhalov, et al. J. Virology, 2000, 74(4): 2046-51.*

* cited by examiner

*Primary Examiner*—Kamal A. Saeed
*Assistant Examiner*—Michael P. Baker
(74) *Attorney, Agent, or Firm*—Michael Morris; Mary-Ellen M. Devlin; David Dow

(57) ABSTRACT

A compound, represented by formula (I):

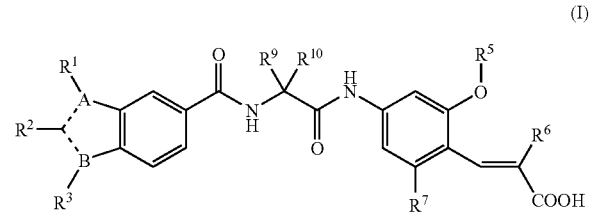

wherein A, B, $R^1$, $R^2$, $R^3$, $R^5$, $R^6$, $R^7$, $R^9$, and $R^{10}$ are as defined herein, or an enantiomer, diastereoisomer or tautomer thereof, including a salt, ester or derivative thereof, as an inhibitor of HCV NS5B polymerase.

33 Claims, No Drawings

VIRAL POLYMERASE INHIBITORS

This application claims benefit from U.S. Provisional Application No. 60/588,670, filed Jul. 16, 2004.

TECHNICAL FIELD OF THE INVENTION

The invention relates to inhibitors of RNA dependent RNA polymerases, particularly those viral polymerases within the Flaviviridae family, more particularly to HCV polymerase.

BACKGROUND OF THE INVENTION

About 30,000 new cases of hepatitis C virus (HCV) infection are estimated to occur in the United States each year (Kolykhalov, A. A.; Mihalik, K.; Feinstone, S. M.; Rice, C. M.; 2000; *J. Virol.* 74: 2046–2051). HCV is not easily cleared by the hosts' immunological defences; as many as 85% of the people infected with HCV become chronically infected. Many of these persistent infections result in chronic liver disease, including cirrhosis and hepatocellular carcinoma (Hoofnagle, J. H.; 1997; *Hepatology* 26: 15S–20S). There are an estimated 170 million HCV carriers world-wide, and HCV-associated end-stage liver disease is now the leading cause of liver transplantation. In the United States alone, hepatitis C is responsible for 8,000 to 10,000 deaths annually. Without effective intervention, the number is expected to triple in the next 10 to 20 years. There is no vaccine to prevent HCV infection.

Currently, the only approved therapy for patients chronically infected with HCV is treatment with interferon or a combination of interferon and ribavirin. Recently, pegylated versions of interferon (peginterferon alpha-2a (Pegasys™, Roche) and peginterferon alpha-2b (PEG-Intron™, Schering)) have been approved for marketing in some countries for treatment of chronic hepatitis C infection, both alone and in combination with ribavirin. However, it has been reported that these therapies achieve a sustained response in fewer than 60% of cases.

HCV belongs to the family Flaviviridae, genus Hepacivirus, which comprises three genera of small enveloped positive-strand RNA viruses (Rice, C. M.; 1996; "Flaviviridae: the viruses and their replication"; pp. 931–960 in *Fields Virology*; Fields, B. N.; Knipe, D. M.; Howley, P. M. (eds.); Lippincott-Raven Publishers, Philadelphia Pa.). The 9.6 kb genome of HCV consists of a long open reading frame (ORF) flanked by 5' and 3' non-translated regions (NTR's). The HCV 5' NTR is 341 nucleotides in length and functions as an internal ribosome entry site for cap-independent translation initiation (Lemon, S. H.; Honda, M.; 1997; *Semin. Virol.* 8: 274–288). The HCV polyprotein is cleaved co- and post-translationally into at least 10 individual polypeptides (Reed, K. E.; Rice, C. M.; 1999; *Curr. Top. Microbiol. Immunol.* 242: 55–84). Cleavage of the structural proteins in the N-terminal portion of the polyprotein is mediated by signal peptidases. Two viral proteases mediate downstream cleavages to produce non-structural (NS) proteins that function as components of the HCV RNA replicase. The NS2-3 protease spans the C-terminal half of the NS2 and the N-terminal one-third of NS3 and catalyses cis cleavage of the NS2/3 site. The same portion of NS3 also encodes the catalytic domain of the NS3-4A serine protease that cleaves at four downstream sites. The C-terminal two-thirds of NS3 is highly conserved amongst HCV isolates, with RNA-binding, RNA-stimulated NTPase, and RNA unwinding activities. Although NS4B and the NS5A phosphoprotein are also likely components of the replicase, their specific roles are unknown. The C-terminal polyprotein cleavage product, NS5B, is the elongation subunit of the HCV replicase possessing RNA-dependent RNA polymerase (RdRp) activity (Behrens, S. E.; Tomei, L.; DeFrancesco, R.; 1996; *EMBO J.* 15: 12–22; and Lohmann, V.; Körner, F.; Herian, U.; Bartenschlager, R.; 1997; *J. Virol.* 71: 8416–8428). It has been recently demonstrated that mutations destroying NS5B activity abolish infectivity of RNA in a chimp model (Kolykhalov, A. A.; Mihalik, K.; Feinstone, S. M.; Rice, C. M.; 2000; *J. Virol.* 74: 2046–2051).

The development of new and specific anti-HCV treatments is a high priority, and virus-specific functions essential for replication are the most attractive targets for drug development. The absence of RNA dependent RNA polymerases in mammals, and the fact that this enzyme appears to be essential to viral replication, would suggest that the NS5B polymerase is an ideal target for anti-HCV therapeutics. WO 01/47883, WO 02/04425, WO 03/000254, WO 03/007945, WO 03/010140, WO 03/026587, WO 03/101993 and WO 04/005286 report inhibitors of NS5B proposed for treatment of HCV.

Indole inhibitors of the NS5B polymerase of HCV are described in WO 03/010141. However, the inhibitors of the invention differ from those described in WO 03/010141 in that they exhibit at least one of the following advantages:
  unexpectedly good activity in a cell-based HCV RNA replication assay;
  improved drug metabolism and pharmokinetics (DMPK) profile; or
  more drug-like properties.

SUMMARY OF THE INVENTION

The present invention provides a novel series of compounds having good to very good inhibitory activity against HCV polymerase and/or at least one of the following advantages:
  unexpectedly good activity in a cell-based HCV RNA replication assay;
  improved drug metabolism and pharmokinetics (DMPK) profile; or
  more drug-like properties.

Further objects of this invention arise for the one skilled in the art from the following description and the examples.

In a first aspect of the invention, there is provided a compound, represented by formula (I):

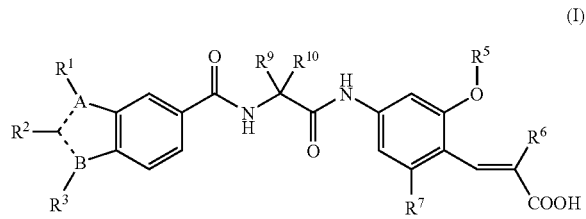

wherein:
either A or B is N and the other B or A is C, wherein—
  between two C-atoms represents a double bond and—
  between a C-atom and a N-atom represents a single bond;
$R^1$ is H or $(C_{1-6})$alkyl;
$R^2$ is $(C_{1-6})$alkyl, $(C_{2-6})$alkynyl, —C(=O)—$(C_{1-6})$alkyl, aryl or Het; the aryl and Het being optionally substituted with $R^{21}$;

wherein $R^{21}$ is one, two or three substituents each independently selected from $(C_{1-6})$alkyl, $(C_{3-7})$cycloalkyl, Het, —CN, —NH$_2$, —NH$(C_{1-6})$alkyl, —N$((C_{1-6})$alkyl$)_2$, halo, —O—$(C_{1-6})$alkyl, —S—$(C_{1-6})$alkyl, —SO—$(C_{1-6})$alkyl and —SO$_2$—$(C_{1-6})$alkyl;

wherein the $(C_{1-6})$alkyl, —O—$(C_{1-6})$alkyl, —S—$(C_{1-6})$alkyl, —SO—$(C_{1-6})$alkyl and —SO$_2$-$(C_{1-6})$alkyl are each optionally substituted with one, two or three halo substituents;

$R^3$ is $(C_{5-6})$cycloalkyl, optionally substituted with from one to four halo substituents;

$R^5$ is selected from H, $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, Het and Het-$(C_{1-6})$alkyl-;

wherein the $(C_{1-6})$alkyl is optionally substituted with from one to three substituents each independently selected from halo, cyano, $(C_{1-6})$alkoxy, —NH$(C_{1-6})$alkyl, —N$((C_{1-6})$alkyl$)_2$ and —NHSO$_2$$(C_{1-6})$alkyl; and wherein each of the Het and the Het portion of the Het-$(C_{1-6})$alkyl- is optionally substituted with $(C_{1-6})$alkyl; and $R^6$ is selected from H, $(C_{1-6})$alkyl and halo; or $R^5$ and $R^6$ are linked such that the group of the subformula

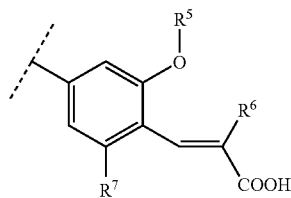

is a group of formula

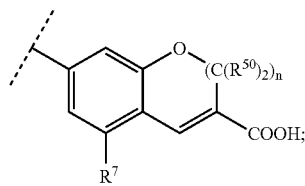

wherein n is 0, 1 or 2; and wherein $R^{50}$ is selected independently in each instance from H, halo, cyano, $(C_{1-6})$alkoxy, $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, Het and Het-$(C_{1-6})$alkyl-;

wherein the $(C_{1-6})$alkyl is optionally substituted with from one to three substituents each independently selected from halo, cyano, $(C_{1-6})$alkoxy, —NH$(C_{1-6})$alkyl, —N$((C_{1-6})$alkyl$)_2$ and —NHSO$_2$$(C_{1-6})$alkyl; and wherein each of the Het and the Het portion of the Het-$(C_{1-6})$alkyl- is optionally substituted with $(C_{1-6})$alkyl;

$R^7$ is selected from H, $(C_{1-6})$alkyl, $(C_{1-6})$alkoxy, $(C_{1-6})$alkylthio, —NH$_2$, —NH$(C_{1-6})$alkyl, —N$((C_{1-6})$alkyl$)_2$ and halo;

$R^9$ and $R^{10}$ are each independently selected from $(C_{1-6})$alkyl; or $R^9$ and $R^{10}$ are covalently bonded together to form $(C_{3-7})$cycloalkyl, $(C_{5-7})$cycloalkenyl or a 4-, 5- or 6-membered heterocycle having from 1 to 3 heteroatoms each independently selected from O, N, and S;

wherein the cycloalkyl, cycloalkenyl or heterocycle is optionally substituted with $(C_{1-4})$alkyl;

wherein Het is defined as a 4- to 7-membered heterocycle having 1 to 4 heteroatoms each independently selected from O, N and S, which may be saturated, unsaturated or aromatic, and which is optionally fused to at least one other cycle to form a 7 to 14-membered heteropolycycle having wherever possible 1 to 5 heteroatoms, each independently selected from O, N and S, the heteropolycycle being saturated, unsaturated or aromatic;

or an enantiomer, diastereoisomer or tautomer thereof, including a salt, ester or derivative thereof.

Included within the scope of this invention are derivatives of compounds of the formula (I) as described hereinbefore, to which at least one of a "detectable label", an "affinity tag" and a "photoreactive group" is linked.

The compounds according to this invention generally show an inhibitory activity against HCV polymerase. In particular compounds according to this invention inhibit RNA synthesis by the RNA dependent RNA polymerase of HCV, especially of the enzyme NS5B encoded by HCV. Furthermore, compounds according to this invention show at least one of the following advantages:

unexpectedly good activity in a cell-based HCV RNA replication assay;
improved drug metabolism and pharmokinetics (DMPK) profile; or
more drug-like properties.

A further advantage of compounds provided by this invention is their low to very low or even non-significant activity against other polymerases.

Another aspect of the invention provides a pharmaceutical composition for the treatment or prevention of HCV infection, comprising an effective amount of a compound of formula (I) according to this invention, or a pharmaceutically acceptable salt or ester thereof, and a pharmaceutically acceptable carrier.

According to a specific embodiment, the pharmaceutical composition of this invention additionally comprises a therapeutically effective amount of one or more antiviral agents. Examples of antiviral agents include, but are not limited to, ribavirin and amantadine.

According to a further specific embodiment, the pharmaceutical composition of this invention additionally comprises at least one other anti-HCV agent as an antiviral agent.

According to a more specific embodiment, the pharmaceutical composition of this invention comprises an additional immunomodulatory agent as an other anti-HCV agent. Examples of additional immunomodulatory agents include but are not limited to, inosine monophosphate inhibitors, α-, β-, δ- γ-, τ- and ω)-interferons, pegylated interferons and conjugated interferons.

According to another more specific embodiment, the pharmaceutical composition of this invention additionally comprises at least one other inhibitor of HCV polymerase as an other anti-HCV agent.

According to another more specific embodiment, the pharmaceutical composition of this invention additionally comprises at least one inhibitor of HCV NS3 protease as an other anti-HCV agent.

According to yet another more specific embodiment, the pharmaceutical composition of this invention additionally comprises at least one inhibitor of another target in the HCV life cycle as an other anti-HCV agent. Examples of such inhibitors include, but are not limited to, agents that inhibit a target selected from a helicase, a NS2/3 protease and an internal ribosome entry site (IRES) and agents that interfere with the function of other viral targets including but not limited to an NS5A protein.

In another aspect of the invention, there is provided a use of a compound of formula (I) according to this invention, or a pharmaceutically acceptable salt or ester thereof, as an HCV polymerase inhibitor.

In still another aspect of the invention, there is provided a use of a compound of the formula (I) according to this invention, or a pharmaceutically acceptable salt or ester thereof, as an inhibitor of RNA dependent RNA polymerase activity of the enzyme NS5B, encoded by HCV.

Yet another aspect of the invention provides a use of a compound of the formula (I) according to this invention, or a pharmaceutically acceptable salt or ester thereof, as an inhibitor of HCV replication.

An important aspect of the invention provides a method of inhibiting the RNA-dependent RNA polymerase activity of the enzyme NS5B, encoded by HCV, comprising exposing the enzyme NS5B to an effective amount of a compound of formula (I) under conditions where the RNA-dependent RNA polymerase activity of the enzyme NS5B is inhibited.

Included in the scope of the invention is a method of inhibiting HCV replication, comprising exposing a cell infected with HCV to an effective amount of a compound of formula (I) under conditions where replication of HCV is inhibited.

In a further aspect of the invention, there is provided a method of treating or preventing HCV infection in a mammal, comprising administering to the mammal an effective amount of a compound of formula (I) according to this invention, or a pharmaceutically acceptable salt or ester thereof.

Yet another aspect of the invention provides a method of treating or preventing HCV infection in a mammal, comprising administering to the mammal an effective amount of a compound of formula (I), or a pharmaceutically acceptable salt or ester thereof, in combination with at least one other antiviral agent.

Further included in the scope of the invention is a use of a compound of formula (I) according to this invention, or of a pharmaceutically acceptable salt or ester thereof, for the manufacture of a medicament for the treatment and/or the prevention of a Flaviviridae viral infection, preferably an HCV infection.

In another aspect of the invention, there is provided a use of a compound of formula (I) according to this invention, or of a pharmaceutically acceptable salt or ester thereof, in combination with at least one other antiviral agent, for the manufacture of a medicament for the treatment and/or the prevention of a Flaviviridae viral infection, preferably an HCV infection.

Yet another aspect of the invention provides an article of manufacture comprising a composition effective to treat an HCV infection or to inhibit the NS5B polymerase of HCV and packaging material comprising a label which indicates that the composition can be used to treat infection by the hepatitis C virus, wherein said composition comprises a compound of formula (I) according to this invention or a pharmaceutically acceptable salt or ester thereof.

DETAILED DESCRIPTION OF THE INVENTION

Definitions

The following definitions apply unless otherwise noted:

As used herein, the term "$(C_{1-n})$alkyl", wherein n is an integer, either alone or in combination with another radical, is intended to mean acyclic straight or branched chain alkyl radicals containing 1 to n carbon atoms respectively. Examples of such radicals include, but are not limited to, methyl, ethyl, n-propyl, 1-methylethyl (iso-propyl), n-butyl, 1-methylpropyl, 2-methylpropyl, 1,1-dimethylethyl (tert-butyl), n-pentyl, etc. In the following, the term Me denotes a methyl group; Et denotes an ethyl group, Pr denotes a propyl group and Bu denotes a butyl group.

If an alkyl group is substituted by halo, it is preferably mono-, di- or trisubstituted with fluoro or monosubstituted by chloro or bromo.

As used herein, the term "$(C_{2-n})$alkenyl", wherein n is an integer, either alone or in combination with another radical, is intended to mean an unsaturated, acyclic straight or branched chain radical containing two to n carbon atoms, at least two of which are bonded to each other by a double bond. Examples of such radicals include, but are not limited to, ethenyl (vinyl), 1-propenyl, 2-propenyl, 1-butenyl, etc. When a $(C_{2-n})$ alkenyl group is substituted, it is understood to be substituted on any carbon atom thereof which would otherwise bear a hydrogen atom, unless specified otherwise.

As used herein, the term "$(C_{2-n})$alkynyl", wherein n is an integer, either alone or in combination with another radical, is intended to mean an unsaturated, acyclic straight or branched chain radical containing two to n carbon atoms, at least two of which are bonded to each other by a triple bond. Examples of such radicals include, but are not limited to, ethynyl, 1-propynyl, 2-propynyl, 1-butynyl, 2-butynyl, 1-methyl-2-propynyl, etc. When a $(C_{2-n})$ alkynyl group is substituted, it is understood to be substituted on any carbon atom thereof which would otherwise bear a hydrogen atom, unless specified otherwise.

As used herein, the term "$(C_{3-n})$cycloalkyl", wherein n is an integer, either alone or in combination with another radical, means a cycloalkyl radical containing from three to n carbon atoms. Examples of such radicals include, but are not limited to, cyclopropyl, cyclobutyl, cyclopentyl, cyclohexyl and cycloheptyl.

As used herein, the term "$(C_{5-n})$cycloalkenyl", wherein n is an integer, either alone or in combination with another radical, means an unsaturated cyclic radical containing five to n carbon atoms. Examples include, but are not limited to, cyclopentenyl and cyclohexenyl.

As used herein the term "$(C_{3-m})$cycloalkyl-$(C_{1-n})$alkyl-", wherein n and m are integers, either alone or in combination with another radical, means a branched or straight chain alkyl radical having 1 to n carbon atoms to which a cycloalkyl radical containing from three to m carbon atoms is covalently bonded. Examples of $(C_{3-7})$cycloalkyl-$(C_{1-6})$alkyl- include, but are not limited to, cyclopropylmethyl, cyclobutylmethyl, cyclopentylmethyl, cyclohexylmethyl, 1-cyclopropylethyl, 2-cyclopropylethyl, 1-cyclobutylethyl, 2-cyclobutylethyl, 1-cyclopentylethyl, 2-cyclopentylethyl, 1-cyclohexylethyl, 2-cyclohexylethyl, etc. Unless specified otherwise, a cycloalkyl-$(C_{1-n})$alkyl- group may be substituted on either the cycloalkyl or the alkyl portion thereof, or both.

As used herein, the term "protecting group" defines protecting groups that can be used during synthetic transformation, examples of which are listed in Greene, "Protective Groups in Organic Chemistry", John Wiley & Sons, New York (1981) and "The Peptides: Analysis, Synthesis, Biology", Vol. 3, Academic Press, New York (1981).

As used herein, the term "aryl" either alone or in combination with another radical means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl and 2-naphthyl.

As used herein, the term "aryl-($C_{1-n}$)alkyl-" means an alkyl radical containing from 1 to n carbon atoms, wherein n is an integer, to which an aryl residue is bonded. Examples of aryl-($C_{1-3}$)alkyl- include, but are not limited to, benzyl (phenylmethyl), 1-phenylethyl, 2-phenylethyl and phenylpropyl. Unless specified otherwise, an aryl-($C_{1-n}$)alkyl- group may be substituted on either the aryl or the alkyl portion thereof, or both.

As used herein, the term "Het" defines a 4- to 7-membered heterocycle having 1 to 4 heteroatoms each independently selected from O, N and S, which may be saturated, unsaturated or aromatic, and which is optionally fused to at least one other cycle to form a 7- to 14-membered heteropolycycle having wherever possible 1 to 5 heteroatoms, each independently selected from O, N and S, the heteropolycycle being saturated, unsaturated or aromatic, unless specified otherwise. When a Het group is substituted, it may be substituted on any carbon atom or heteroatom thereof which would otherwise bear a hydrogen atom, unless specified otherwise. Substituents which may be bonded to carbon atoms or to heteroatoms are those which give rise to chemically stable compounds, such as are recognized by those skilled in the art.

As used herein, the term "Het-($C_{1-n}$)alkyl-" means an alkyl radical containing from 1 to n carbon atoms, wherein n is an integer, to which an Het residue is bonded. Unless specified otherwise, an Het-($C_{1-n}$)alkyl- group may be substituted on either the Het or the alkyl portion thereof, or both.

As used herein the term "heteroatom" means O, S or N.

As used herein, the term "heterocycle", either alone or in combination with another radical, means a monovalent radical derived by removal of a hydrogen from a three- to seven-membered saturated or unsaturated (including aromatic) heterocycle containing from one to four heteroatoms each independently selected from nitrogen, oxygen and sulfur. Examples of such heterocycles include, but are not limited to, azetidine, pyrrolidine, tetrahydrofuran, thiazolidine, pyrrole, thiophene, hydantoin, diazepine, 1H-imidazole, isoxazole, thiazole, tetrazole, piperidine, piperazine, homopiperidine, homopiperazine, 1,4-dioxane, 4-morpholine, 4-thiomorpholine, pyridine, pyridine-N-oxide or pyrimidine, or the following heterocycles:

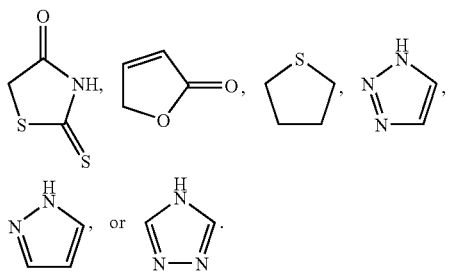

As used herein, the term "heteropolycycle" either alone or in combination with another radical, means a heterocycle as defined above fused to one or more other cycle, be it a heterocycle or any other cycle. Examples of such heteropolycycles include, but are not limited to, indole, benzimidazole, thiazolo[4,5-b]-pyridine, quinoline, isoquinoline, or coumarin, or the following:

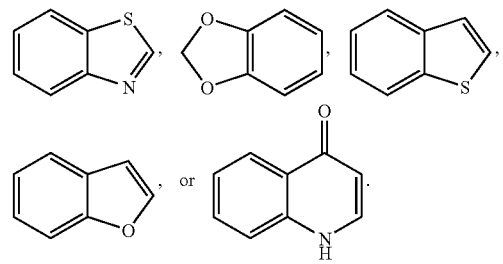

As used herein, the term "halo" means a halogen substituent and includes fluoro, chloro, bromo and iodo.

As used herein, the term "OH" refers to a hydroxyl group. It is well known to one skilled in the art that hydroxyl groups may be substituted by functional group equivalents. Examples of such functional group equivalents that are contemplated by this invention include, but are not limited to, ethers, sulfhydryls, and primary, secondary or tertiary amines.

As used herein, the term "SH" refers to a sulfhydryl group. It is intended within the scope of the present invention that, whenever a "SH" or "SR" group is present, it can also be substituted by any other appropriate oxidation state such as SOR, $SO_2R$, or $SO_3R$.

As used herein, the term "—O—($C_{1-n}$)alkyl" or "($C_{1-n}$) alkoxy", used interchangeably, refers to an oxygen atom further bonded to an alkyl radical containing from 1 to n carbon atoms. Examples of ($C_{1-6}$)alkoxy include, but are not limited to, methoxy ($CH_3O$—), ethoxy ($CH_3CH_2O$—), propoxy ($CH_3CH_2CH_2O$—), 1-methylethoxy (isopropoxy; $(CH_3)_2CHO$—), 1,1-dimethylethoxy (tert-butoxy; $(CH_3)_3CO$—), etc. When an O—($C_{1-n}$)alkyl radical is substituted, it is understood to be substituted on the ($C_{1-n}$)alkyl portion thereof.

As used herein, the term "—S—($C_{1-n}$)alkyl" or "($C_{1-n}$) alkylthio", used interchangeably, refers to a sulfur atom further bonded to an alkyl radical containing from 1 to n carbon atoms. Examples of ($C_{1-6}$)alkylthio include, but are not limited to, methylthio ($CH_3S$—), ethylthio ($CH_3CH_2S$—), propylthio ($CH_3CH_2CH_2S$—), 1-methylethylthio (isopropylthio; $(CH_3)_2CHS$—), 1,1-dimethylethylthio (tert-butylthio; $(CH_3)_3CS$—), etc. When an —S—($C_{1-n}$) alkyl radical, an —SO—($C_{1-n}$)alkyl radical or an —$SO_2$— ($C_{1-n}$)alkyl radical are substituted, each is understood to be substituted on the ($C_{1-n}$)alkyl portion thereof.

As used herein, the term "COOH" refers to a carboxylic acid group. It is well known to one skilled in the art that carboxylic acid groups may be substituted by functional group equivalents. Examples of such functional group equivalents that are contemplated by this invention include, but are not limited to, esters, amides, imides, boronic acids, phosphonic acids, sulfonic acids, tetrazoles, triazoles, N-acylsulfamides ($RCONHSO_2NR_2$), and N-acylsulfonamides ($RCONHSO_2R$).

When protected, as during a synthetic transformation, for example, a carboxyl group is usually protected as an ester that can be cleaved to give the carboxylic acid. Protecting groups that can be used include, but are not limited to: 1) alkyl esters such as methyl, ethyl, trimethylsilylethyl and tert-butyl, 2) aralkyl esters such as benzyl and substituted benzyl, or 3) esters that can be cleaved by mild base treatment or mild reductive means such as trichloroethyl and phenacyl esters.

As used herein, the term "functional group equivalent" is intended to mean an element or group or a substituted derivative thereof, that is replaceable by another element or group that has similar electronic, hybridization or bonding properties.

The following signs ----- and ⁓⁓⁓ are used interchangeably in subformulas to indicate the bond, or in the case of a spirocyclic group the atom, which is bonded to the rest of the molecule as defined.

As used herein, the term "derivative thereof" means a compound to which at least one of a detectable label, an affinity tag and a photoreactive group is linked.

As used herein, the term "detectable label" means any group that may be linked to the polymerase or to a compound of the present invention such that when the compound is associated with the polymerase target, such label allows recognition either directly or indirectly of the compound such that it can be detected, measured and quantified. Examples of such "labels" are intended to include, but are not limited to, fluorescent labels, chemiluminescent labels, calorimetric labels, enzymatic markers, radioactive isotopes and affinity tags such as biotin. Such labels are attached to the compound or to the polymerase by well known methods.

As used herein, the term "affinity tag" means a ligand (that may be linked to the polymerase or to a compound of the present invention) whose strong affinity for a receptor can be used to extract from a solution the entity to which the ligand is attached. Examples of such ligands include, but are not limited to, biotin or a derivative thereof, a histidine polypeptide, a polyarginine, an amylose sugar moiety or a defined epitope recognizable by a specific antibody. Such affinity tags are attached to the compound or to the polymerase by well-known methods.

As used herein, the term "photoreactive group" means a group that is transformed, upon activation by light, from an inert group to a reactive species, such as a free radical. Such a group may be used as, for example, a photoaffinity label. Examples of such groups include, but are not limited to, benzophenones, azides, and the like.

The term "salt thereof" means any acid and/or base addition salt of a compound according to the invention; preferably a pharmaceutically acceptable salt thereof.

The term "pharmaceutically acceptable salt" means a salt of a compound of formula (I) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Examples of suitable salts are found in, e.g., S. M. Birge et al., J. Pharm. Sci., 1977, 66, pp. 1–19.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, sulfuric acid, sulfamic acid, nitric acid, phosphoric acid, and the like, and organic acids such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethane-sulfonic acid (isethionic acid), lactic acid, hydroxymaleic acid, malic acid, malonic acid, mandelic acid, mesitylenesulfonic acid, methanesulfonic acid, naphthalene-sulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic nontoxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "ester thereof" means any ester of a compound in which any of the carboxyl functions of the molecule is replaced by an alkoxycarbonyl function, including but not limited to pharmaceutically acceptable esters thereof.

The term "pharmaceutically acceptable ester" as used herein, either alone or in combination with another substituent, means esters of the compound of formula (I) in which any of the carboxyl functions of the molecule, but preferably the carboxy terminus, is replaced by an alkoxycarbonyl function:

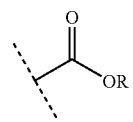

in which the R moiety of the ester is selected from alkyl (e.g. methyl, ethyl, n-propyl, tert-butyl, n-butyl); alkoxyalkyl (e.g. methoxymethyl); alkoxyacyl (e.g. acetoxymethyl); aralkyl (e.g. benzyl); aryloxyalkyl (e.g. phenoxymethyl);

aryl (e.g. phenyl), optionally substituted with halogen, $(C_{1-4})$ alkyl or $(C_{1-4})$alkoxy. Other suitable esters can be found in Design of prodrugs, Bundgaard, H. Ed. Elsevier (1985). Such pharmaceutically acceptable esters are usually hydrolyzed in vivo when administered to a mammal and transformed into the acid form of the compound of formula (I). With regard to the esters described above, unless otherwise specified, any alkyl moiety present advantageously contains 1 to 16 carbon atoms, particularly 1 to 6 carbon atoms. Any aryl moiety present in such esters advantageously comprises a phenyl group. In particular the esters may be a $(C_{1-16})$alkyl ester, an unsubstituted benzyl ester or a benzyl ester substituted with at least one halogen, $(C_{1-6})$alkyl, $(C_{1-6})$alkoxy, nitro or trifluoromethyl.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus inca mammal. Such agents include but are not limited to, another anti-HCV agent, an HIV inhibitor, an HAV inhibitor and an HBV inhibitor. Antiviral agents include, but are not limited to, ribavirin, amantadine, Levovirin, and Viramidine.

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, other inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, but are not limited to, inosine monophosphate inhibitors (such as VX-497 (merimepodib, Vertex Pharmaceuticals)), class I interferons (such as α-, β-, δ- and ω interferons, τ-interferons, consensus interferons and asialo-interferons), class II interferons (such as γ-interferons), pegylated interferons and conjugated interferons, including but not limited to interferons conjugated with other proteins including but not limited to human albumin.

The term "inhibitor of HCV NS3 protease" as used herein means an agent (compound or biological) that is effective to inhibit the function of HCV NS3 protease in a mammal. Inhibitors of HCV NS3 protease include, but are not limited to, those compounds described in WO 99/07733, WO 99/07734, WO 00/09558, WO 00/09543, WO 00/59929, WO 02/060926, U.S. 2002/0177725, WO 03/053349, WO 03/062265, WO 03/064416, WO 03/064455, WO 03/064456, WO 03/099316, WO 03/099274, WO 2004/030670, WO 2004/032827, WO 2004/037855, WO 2004/039833, WO 2004/043339, WO 2004/072243, WO 2004/093798, WO 2004/094452, WO 2004/101602, WO 2004/101605, WO 2004/103996, WO 2004/113365, the Boehringer Ingelheim clinical candidate identified as BILN 2061 and the Vertex candidate identified as VX-950.

The term "inhibitor of HCV polymerase" as used herein means an agent (compound or biological) that is effective to inhibit the function of an HCV polymerase in a mammal. This includes, but is not limited to, non-nucleoside and nucleoside inhibitors of HCV NS5B polymerase. Examples of inhibitors of HCV polymerase include but are not limited to those compounds described in: WO 02/04425, WO 03/007945, WO 03/010140, WO 03/010141, WO 2004/064925, WO 2004/065367 and U.S. application Ser. No. 11/062,305, herein incorporated by reference (all by Boehringer Ingelheim), WO 2005/012288 (Genelabs), WO 2004/087714 (IRBM), WO 03/101993 (Neogenesis), WO 03/026587 (BMS), WO 03/000254 (Japan Tobacco), and WO 01/47883 (Japan Tobacco), and the clinical candidates JTK-003 (Japan Tobacco), HCV 796 (ViroPharma/Wyeth), R-1626 (Roche) and NM 283 (Idenix/Novartis).

The term "inhibitor of another target in the HCV life cycle" as used herein means an agent (compound or biological) that is effective to inhibit the formation and/or replication of HCV in a mammal other than by inhibiting the function of the HCV NS3 protease. This includes agents that interfere with either host or HCV viral mechanisms necessary for the formation and/or replication of HCV in a mammal. Inhibitors of another target in the HCV life cycle include, but are not limited to, agents that inhibit a target selected from a helicase, a NS2/3 protease and an internal ribosome entry site (IRES) and agents that interfere with the function of other viral targets including but not limited to an NS5A protein.

The term "HIV inhibitor" as used herein means an agent (compound or biological) that is effective to inhibit the formation and/or replication of HIV in a mammal. This includes agents that interfere with either host or viral mechanisms necessary for the formation and/or replication of HIV in a mammal. HIV inhibitors include, but are not limited to, nucleoside inhibitors, non-nucleoside inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include, but are not limited to, Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include agents that inhibit HBV viral DNA polymerase or HBV vaccines. Specific examples of HBV inhibitors include, but are not limited to, Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type I. This includes both naturally and synthetically produced class I interferons. Examples of class I interferons include, but are not limited to, α-, β-, δ-, ω-interferons, τ-interferons, consensus interferons, asialo-interferons and pegylated forms thereof.

The term "class II interferon" as used herein means an interferon selected from a group of interferons that all bind to receptor type II. Examples of class II interferons include, but are not limited to, γ-interferons.

As discussed above, combination therapy is contemplated wherein a compound of formula (I), or a pharmaceutically acceptable salt or ester thereof, is co-administered with at least one additional agent selected from: an antiviral agent, an immunomodulatory agent, an inhibitor of HCV NS3 protease, another inhibitor of HCV polymerase, an inhibitor of another target in the HCV life cycle, an HIV inhibitor, an HAV inhibitor and an HBV inhibitor. Examples of such agents are provided in the Definitions section above. Specific preferred examples of such agents are listed below:

antiviral agents: ribavirin or amantadine;

immunomodulatory agents: inosine monophosphate inhibitors, class I interferons, class II interferons, pegylated interferons and conjugated interferons.

HCV NS3 protease inhibitors;

other inhibitors of the HCV polymerase: nucleoside or non-nucleoside inhibitors;

an inhibitor of another target in the HCV life cycle: agents that inhibit a target selected from a helicase, a NS2/3 protease and an internal ribosome entry site (IRES) and agents that interfere with the function of other viral targets including but not limited to an NS5A protein;

HIV inhibitors: nucleoside inhibitors, non-nucleoside inhibitors, protease inhibitors, fusion inhibitors or integrase inhibitors; or HBV inhibitors: agents that inhibit HBV viral DNA polymerase or an agent that is an HBV vaccine.

These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of a compound of formula (I), or a pharmaceutically acceptable salt or ester thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectible levels in the blood.

PREFERRED EMBODIMENTS

Unless stated otherwise, all groups and substituents, including but not limited to $R^1$, $R^2$, $R^3$, $R^5$, $R^6$, $R^7$, $R^9$, $R^{10}$, $R^{21}$, A, B, and Het, have the definitions as defined hereinbefore and hereinafter. In the following, the preferred embodiments, groups and substituents according to this invention are described.

Core:

This invention provides compounds of the formulas (Ia) and (Ib) below:

(Ia)

(Ib)

Any and each individual definition of Core as set out herein may be combined with any and each individual definition of $R^1$, $R^2$, $R^3$, $R^5$, $R^6$, $R^7$, $R^9$ and $R^{10}$ as set out herein.

$R^1$:

According to a preferred embodiment of this invention $R^1$ is selected from the group consisting of H and methyl. Most preferably $R^1$ is methyl.

Any and each individual definition of $R^1$ as set out herein may be combined with any and each individual definition of Core, $R^2$, $R^3$, $R^5$, $R^6$, $R^7$, $R^9$ and $R^{10}$ as set out herein.

$R^2$:

In a preferred embodiment, $R^2$ is $(C_{1-6})$alkyl.

More preferably within this embodiment, $R^2$ is methyl.

In an alternative preferred embodiment, $R^2$ is $(C_{2-6})$alkynyl.

More preferably within this embodiment, $R^2$ is ethynyl.

In another alternative preferred embodiment, $R^2$ is —C(=O)—$(C_{1-6})$alkyl.

More preferably within this embodiment, $R^2$ is ethanoyl.

In yet another alternative preferred embodiment, $R^2$ is aryl or Het, wherein Het is a 5- or 6-membered monocyclic aromatic heterocycle having 1 to 4 heteroatoms each independently selected from O, N and S, which is optionally fused to one other cycle to form an 8- to 11-membered aromatic heteropolycycle having wherever possible 1 to 5 heteroatoms, each independently selected from O, N and S; wherein $R^2$ is unsubstituted or substituted with $R^{21}$, wherein $R^{21}$ is as defined herein.

More preferably $R^2$ is phenyl or Het, wherein Het is selected from

-continued

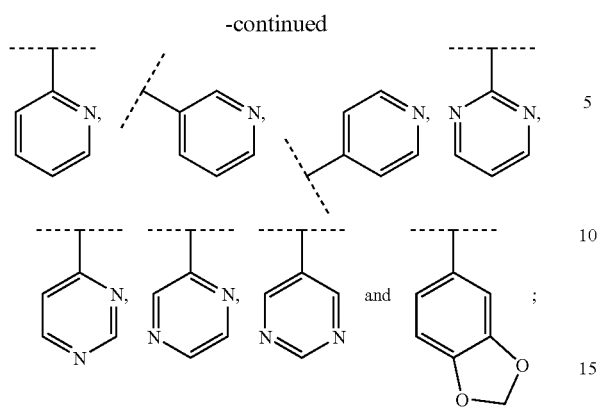

and wherein R² is unsubstituted or substituted with R²¹, wherein R²¹ is as defined herein.

Preferably, R²¹ is one, two or three substituents each independently selected from $(C_{1-3})$alkyl, $(C_{3-6})$cycloalkyl, —CN, —NH₂, —NH$(C_{1-3})$alkyl, —N$((C_{1-3})$alkyl$)_2$, halo, —O—$(C_{1-3})$alkyl, —S—$(C_{1-3})$alkyl, —SO—$(C_{1-3})$alkyl and —SO₂—$(C_{1-3})$alkyl;

wherein the $(C_{1-3})$alkyl, —O—$(C_{1-3})$alkyl, —S—$(C_{1-3})$alkyl, —SO—$(C_{1-3})$alkyl and —SO₂—$(C_{1-3})$alkyl are each optionally substituted with one, two or three halo substituents.

More preferably, R²¹ is one, two or three substituents each independently selected from fluoro, chloro, bromo, methyl, ethyl, propyl, 1-methylethyl, trifluoromethyl, cyclopropyl, cyclobutyl, cyclopentyl, cyclohexyl, methoxy, ethoxy, propoxy, 1-methylethoxy, methylthio, ethylthio, propylthio, 1-methylethylthio, amino, N-methylamino, N,N-dimethylamino, —SO₂CH₃ and cyano.

Most preferably, R²¹ is one or two substituents each independently selected from fluoro, chloro, bromo, methyl, methoxy, amino, —SO₂CH₃ and cyano.

Therefore, preferably, R² is selected from:

methyl, ethynyl, ethanoyl,

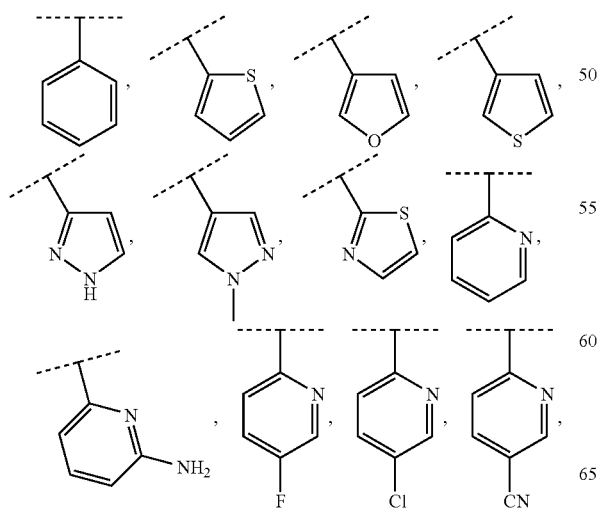

-continued

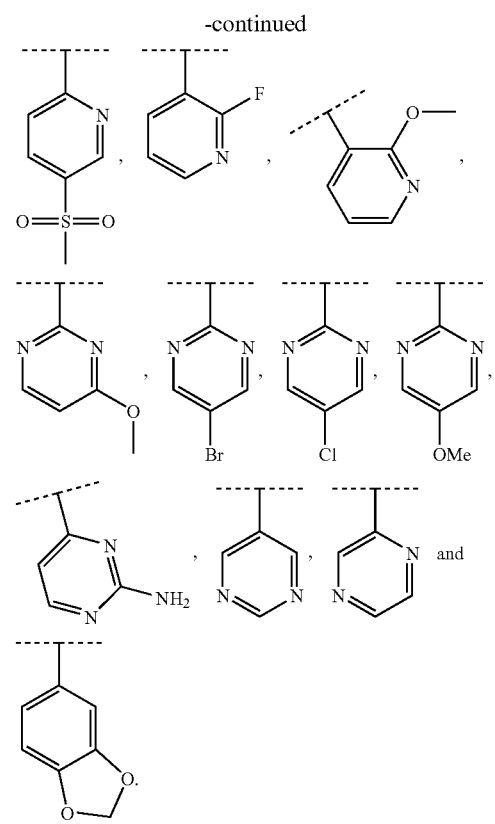

More preferably, R² is selected from:

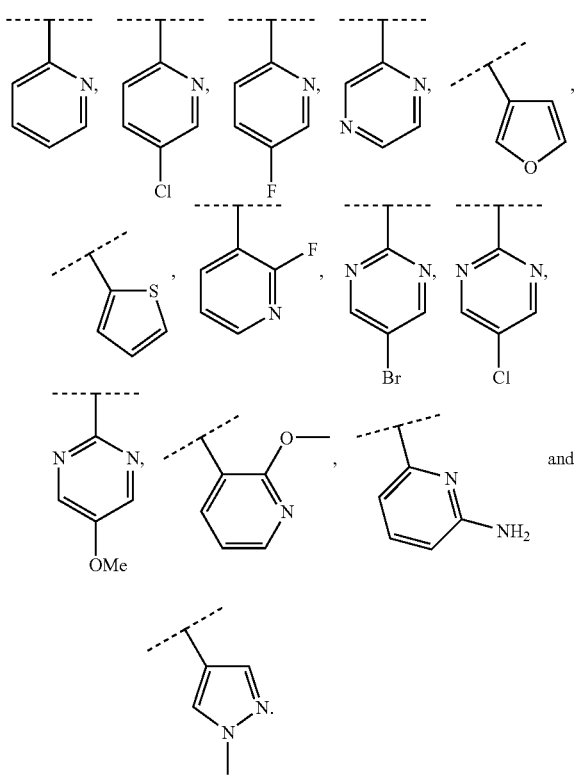

Most preferably, $R^2$ is selected from:

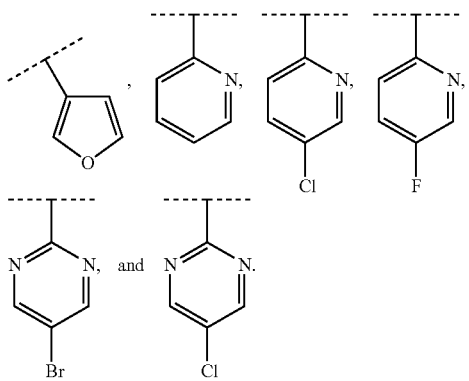

Any and each individual definition of $R^2$ as set out herein may be combined with any and each individual definition of Core, $R^1$, $R^3$, $R^5$, $R^6$, $R^7$, $R^9$ and $R^{10}$ as set out herein.

$R^3$:

Preferably, $R^3$ is cyclopentyl or cyclohexyl, each being optionally substituted with one to four fluoro substituents.

More preferably, $R^3$ is cyclopentyl, optionally substituted with one to four fluoro substituents. Alternatively more preferably, $R^3$ is cyclohexyl, optionally substituted with one to four fluoro substituents.

Most preferably, $R^3$ is cyclopentyl or cyclohexyl.

Any and each individual definition of $R^3$ as set out herein may be combined with any and each individual definition of Core, $R^1$, $R^2$, $R^5$, $R^6$, $R^7$, $R^9$ and $R^{10}$ as set out herein.

$R^5$:

In one preferred embodiment, $R^5$ is selected from $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, Het and Het-$(C_{1-6})$alkyl-; wherein the Het and the Het portion of the Het-$(C_{1-6})$alkyl- are each selected from a 5- or 6-membered saturated, unsaturated or aromatic monocyclic heterocycle, having one to three heteroatoms each independently selected from N, O and S; and wherein the $(C_{1-6})$alkyl is optionally substituted with from one to three substituents each independently selected from halo, cyano, $(C_{1-6})$alkoxy, —NH$(C_{1-6})$alkyl, —N$((C_{1-6})$alkyl$)_2$ and —NHSO$_2(C_{1-6})$alkyl; and wherein each of the Het and the Het portion of the Het-$(C_{1-6})$alkyl- is optionally substituted with $(C_{1-6})$alkyl.

More preferably, $R^5$ is selected from methyl, ethyl, propyl, 1-methylethyl, butyl, 1-methylpropyl, 2-methylpropyl, 1,1-dimethylethyl, 2-propenyl, 2-propynyl, cyclopropyl, cyclobutyl, cyclopropylmethyl, cyclobutylmethyl,

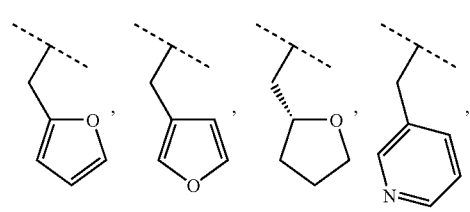

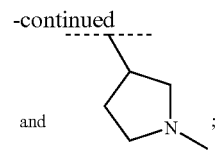

wherein the methyl, ethyl, propyl, 1-methylethyl, butyl, 1-methylpropyl, 2-methylpropyl and 11-dimethylethyl are each optionally substituted with from one to three substituents each independently selected from fluoro, methoxy, ethoxy, —N(CH$_3$)$_2$, and —NHSO$_2$CH$_3$.

Even more preferably, $R^5$ is selected from:

methyl, ethyl, propyl, 1-methylethyl, 1-methylpropyl, 2-methylpropyl, difluoromethyl, 2-methoxyethyl, 2-methoxy-1-methylethyl, 2-ethoxyethyl, 2-(N,N-dimethylamino)ethyl, 3-(N,N-dimethylamino)propyl, 2-propenyl, 2-propynyl, cyclobutyl, cyclopropylmethyl,

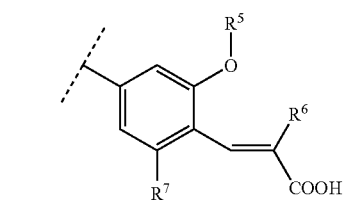

Still more preferably, $R^5$ is methyl, ethyl or 2-methoxyethyl.

Most preferably, $R^5$ is ethyl or 2-methoxyethyl.

Any and each individual definition of $R^5$ as set out herein may be combined with any and each individual definition of Core, $R^1$, $R^2$, $R^3$, $R^6$, $R^7$, $R^9$ and $R^{10}$ as set out herein.

$R^6$:

Preferably, $R^6$ is H, methyl, ethyl or fluoro.

More preferably, $R^6$ is H or methyl.

Most preferably, $R^6$ is H.

Any and each individual definition of $R^6$ as set out herein may be combined with any and each individual definition of Core, $R^1$, $R^2$, $R^3$, $R^5$, $R^7$, $R^9$ and $R^{10}$ as set out herein.

In an alternative preferred embodiment, $R^5$ and $R^6$ are linked such that the group of the subformula is preferably a group of formula

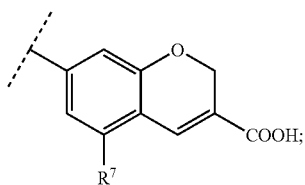

wherein R⁷ is as defined herein.

Any and each individual definition of $R^5$ and $R^6$ as set out herein may be combined with any and each individual definition of Core, $R^1$, $R^2$, $R^3$, $R^7$, $R^9$ and $R^{10}$ as set out herein.

$R^7$:

Preferably $R^7$ is H, methyl, ethyl, methoxy or ethoxy.

More preferably, $R^7$ is H or methoxy.

Most preferably, $R^7$ is H.

Any and each individual definition of $R^7$ as set out herein may be combined with any and each individual definition of Core, $R^1$, $R^2$, $R^3$, $R^5$, $R^6$, $R^9$ and $R^{10}$ as set out herein.

$R^9$ and $R^{10}$:

Preferably, $R^9$ and $R^{10}$ are each independently selected from $(C_{1-3})$alkyl or $R^9$ and $R^{10}$ are covalently bonded together to form $(C_{3-6})$cycloalkyl, $(C_{5-6})$cycloalkenyl or a 5- or 6-membered heterocycle having from 1 to 2 heteroatoms each independently selected from O and N; wherein the cycloalkyl, cycloalkenyl and heterocycle are each optionally substituted with $(C_{1-4})$alkyl.

More preferably, the group

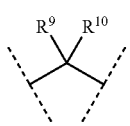

is selected from:

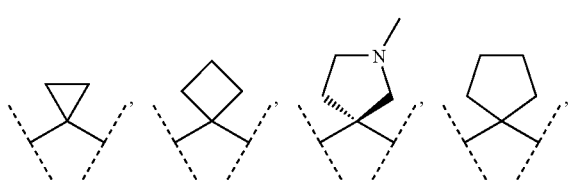

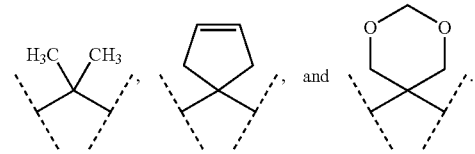

Even more preferably, the group

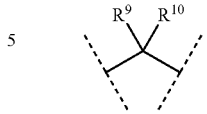

is selected from:

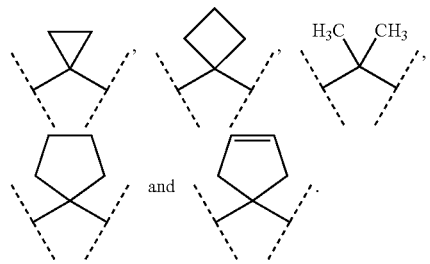

Most preferably, the group

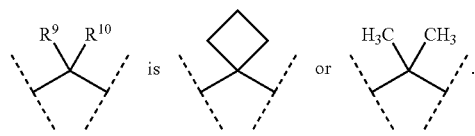

Any and each individual definition of $R^9$ and $R^{10}$ as set out herein may be combined with any and each individual definition of Core, $R^1$, $R^2$, $R^3$, $R^5$, $R^6$ and $R^7$ as set out herein.

Also encompassed within the scope of the present invention are compounds of formula (I):

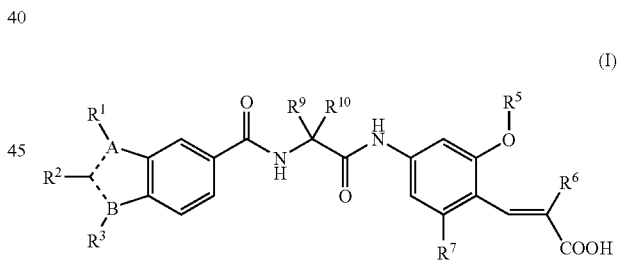

(I)

wherein:
either A or B is N and the other B or A is C, wherein— between two C-atoms represents a double bond and— between a C-atom and a N-atom represents a single bond;
$R^1$ is H or $(C_{1-6})$alkyl;
$R^2$ is $(C_{2-6})$alkynyl, —C(═O)—$(C_{1-6})$alkyl, aryl or Het; the aryl and Het being optionally substituted with $R^{21}$;
wherein $R^{21}$ is one, two or three substituents each independently selected from $(C_{1-6})$alkyl, $(C_{3-7})$cycloalkyl, Het, —CN, —NH₂, —NH$(C_{1-6})$alkyl, —N($(C_{1-6})$alkyl)₂, halo, —O—$(C_{1-6})$alkyl, —S—$(C_{1-6})$alkyl, —SO—$(C_{1-6})$alkyl and —SO₂—$(C_{1-6})$alkyl;
wherein the $(C_{1-6})$alkyl, —O—$(C_{1-6})$alkyl, —S—$(C_{1-6})$alkyl, —SO—$(C_{1-6})$alkyl and —SO₂—$(C_{1-6})$alkyl are each optionally substituted with one, two or three halo substituents;

$R^3$ is $(C_{5-6})$cycloalkyl, optionally substituted with from one to four halo substituents;

$R^5$ is selected from H, $(C_{1-6})$alkyl, $(C_{2-6})$alkenyl, $(C_{2-6})$alkynyl, $(C_{3-7})$cycloalkyl, and $(C_{3-7})$cycloalkyl-$(C_{1-6})$alkyl-;
wherein the $(C_{1-6})$alkyl is optionally substituted with from one to three substituents each independently selected from halo, cyano and $(C_{1-6})$alkoxy; and $R^6$ is selected from H, $(C_{1-6})$alkyl and halo; or $R^5$ and $R^6$ are linked, together with the atoms to which they are attached, to form a 5-, 6- or 7-membered ring;

$R^7$ is selected from H, $(C_{1-6})$alkyl, $(C_{1-6})$alkoxy, $(C_{1-6})$alkylthio, —$NH_2$, —$NH(C_{1-6})$alkyl, —$N((C_{1-6})$alkyl$)_2$ and halo;

$R^9$ and $R^{10}$ are each independently selected from $(C_{1-6})$alkyl; or $R^9$ and $R^{10}$ are covalently bonded together to form $(C_{3-7})$cycloalkyl, $(C_{5-7})$cycloalkenyl or a 4-, 5- or 6-membered heterocycle having from 1 to 3 heteroatoms each independently selected from O, N, and S;
wherein the cycloalkyl, cycloalkenyl or heterocycle are each optionally substituted with $(C_{1-4})$alkyl;

wherein Het is defined as a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, the heteropolycycle being saturated, unsaturated or aromatic;

or an enantiomer, diastereoisomer or tautomer thereof, including a salt thereof.

Preferably provided are compounds of formula (I), in particular of the formula (Ia) or (Ib), wherein:

$R^1$ is H or methyl;

$R^2$ is aryl or Het, wherein Het is a 5- or 6-membered monocyclic aromatic heterocycle having 1 to 4 heteroatoms each independently selected from O, N and S, which is optionally fused to one other cycle to form an 8- to 11-membered aromatic heteropolycycle having wherever possible 1 to 5 heteroatoms, each independently selected from O, N and S;

wherein the aryl and Het are each optionally substituted with $R^{21}$, wherein $R^{21}$ is one, two or three substituents each independently selected from $(C_{1-3})$alkyl, $(C_{3-6})$cycloalkyl, —CN, —$NH_2$, —$NH(C_{1-3})$alkyl, —$N((C_{1-3})$alkyl$)_2$, halo, —O—$(C_{1-3})$alkyl, —S—$(C_{1-3})$alkyl, —SO—$(C_{1-3})$alkyl and —$SO_2$—$(C_{1-3})$alkyl;
wherein the $(C_{1-3})$alkyl, —O—$(C_{1-3})$alkyl, —S—$(C_{1-3})$alkyl, —SO—$(C_{1-3})$alkyl and —$SO_2$—$(C_{1-3})$alkyl are each optionally substituted with one, two or three halo substituents;

$R^3$ is cyclopentyl or cyclohexyl, each being optionally substituted with one to four fluoro substituents;

$R^5$ is selected from $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, Het and Het-$(C_{1-6})$alkyl-; wherein the Het and the Het portion of the Het-$(C_{1-6})$alkyl- are each selected from a 5- or 6-membered saturated, unsaturated or aromatic monocyclic heterocycle, having one to three heteroatoms each independently selected from N, O and S; and
wherein the $(C_{1-6})$alkyl is optionally substituted with from one to three substituents each independently selected from halo, cyano, $(C_{1-6})$alkoxy, —$NH(C_{1-6})$alkyl, —$N((C_{1-6})$alkyl$)_2$ and —$NHSO_2(C_{1-6})$alkyl; and wherein each of the Het and the Het portion of the Het-$(C_{1-6})$alkyl- is optionally substituted with $(C_{1-6})$alkyl; and $R^6$ is H, methyl, ethyl or fluoro; or $R^5$ and $R^6$ are linked such that the group of the subformula is preferably a group of formula $R^7$ is H, methyl, ethyl, methoxy or ethoxy; and $R^9$ and $R^{10}$ are each independently selected from $(C_{1-3})$alkyl or $R^9$ and $R^{10}$ are covalently bonded together to form $(C_{3-6})$cycloalkyl, $(C_{5-6})$cycloalkenyl or a 5- or 6-membered heterocycle having from 1 to 2 heteroatoms each independently selected from O and N; wherein the cycloalkyl, cycloalkenyl and heterocycle are each optionally substituted with $(C_{1-4})$alkyl.

More preferably, $R^1$ is H or methyl;

$R^2$ is phenyl or Het, wherein Het is selected from wherein $R^2$ is unsubstituted or substituted with $R^{21}$, wherein
$R^{21}$ is one, two or three substituents each independently selected from fluoro, chloro, bromo, methyl, ethyl, propyl, 1-methylethyl, trifluoromethyl, cyclopropyl, cyclobutyl, cyclopentyl, cyclohexyl, methoxy, ethoxy, propoxy, 1-methylethoxy, methylthio, ethylthio, propylthio, 1-methylethylthio, amino, N-methylamino, N,N-dimethylamino, —$SO_2CH_3$ and cyano;
$R^3$ is cyclopentyl or cyclohexyl, each optionally substituted with one to four fluoro substituents;
$R^5$ is selected from methyl, ethyl, propyl, 1-methylethyl, butyl, 1-methylpropyl, 2-methylpropyl, 1,1-dimethylethyl, 2-propenyl, 2-propynyl, cyclopropyl, cyclobutyl, cyclopropylmethyl, cyclobutylmethyl,

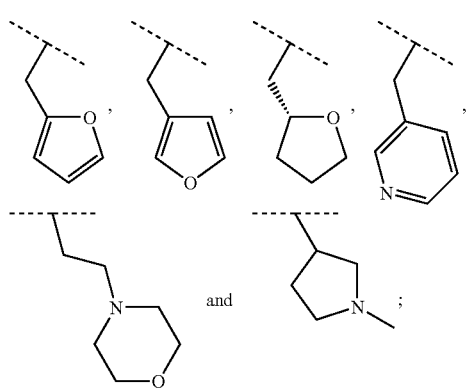

wherein the methyl, ethyl, propyl, 1-methylethyl, butyl, 1-methylpropyl, 2-methylpropyl and 1,1-dimethylethyl are each optionally substituted with from one to three substituents each independently selected from fluoro, methoxy, ethoxy, —$N(CH_3)_2$, and —$NHSO_2CH_3$;
$R^6$ is H, methyl, ethyl or fluoro;
$R^7$ is H or methoxy; and
the group

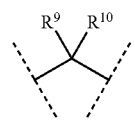

is selected from:

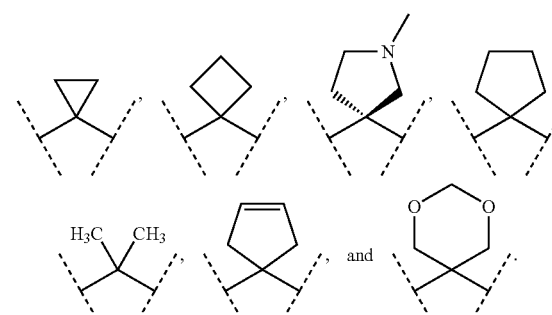

Alternatively more preferably,
$R^1$ is H or methyl;

$R^2$ is phenyl or Het, wherein Het is selected from

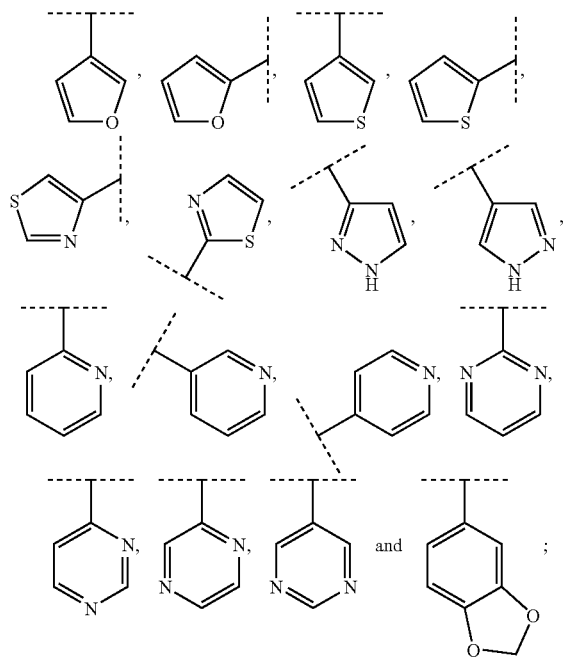

wherein $R^2$ is unsubstituted or substituted with $R^{21}$, wherein
$R^{21}$ is one, two or three substituents each independently selected from fluoro, chloro, bromo, methyl, ethyl, propyl, 1-methylethyl, trifluoromethyl, cyclopropyl, cyclobutyl, cyclopentyl, cyclohexyl, methoxy, ethoxy, propoxy, 1-methylethoxy, methylthio, ethylthio, propylthio, 1-methylethylthio, amino, N-methylamino, N,N-dimethylamino, —$SO_2CH_3$ and cyano;
$R^3$ is cyclopentyl or cyclohexyl, each optionally substituted with one to four fluoro substituents;
$R^5$ and $R^6$ are linked, together with the atoms to which they are attached, to form a 6-membered ring, such that the group of the subformula

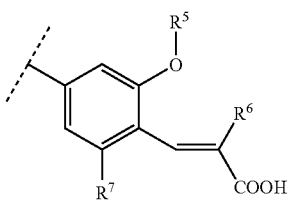

is a group of formula

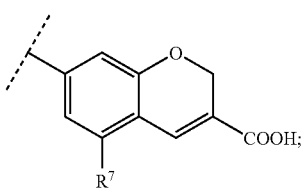

$R^7$ is H or methoxy; and the group

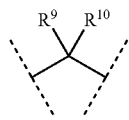

is selected from:

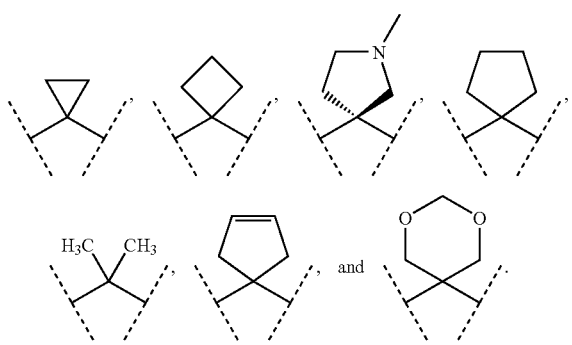

Even more preferably
R¹ is H or methyl;
R² is selected from:
methyl, ethynyl, ethanoyl,

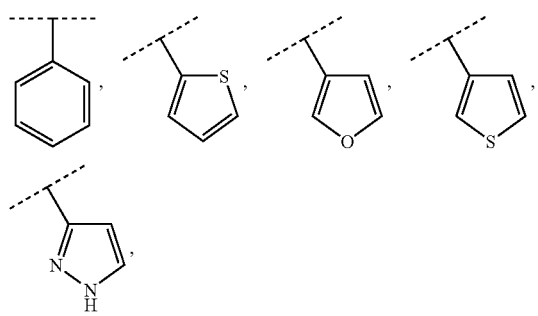

,

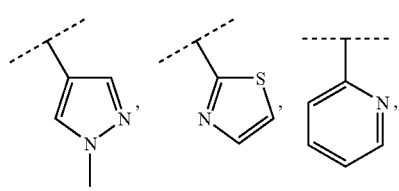

,

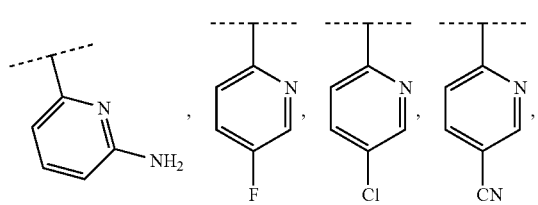

,

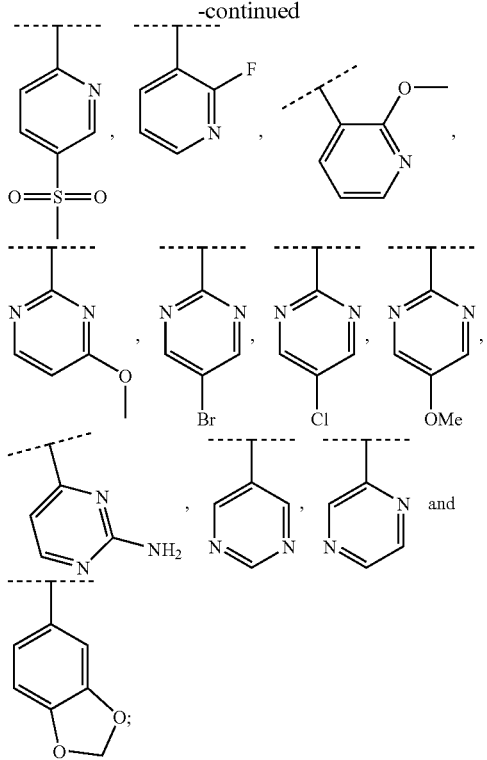

R³ is cyclopentyl or cyclohexyl, each optionally substituted with one to four fluoro substituents;
R⁵ is selected from methyl, ethyl, propyl, 1-methylethyl, 1-methylpropyl, 2-methylpropyl, difluoromethyl, 2-methoxyethyl, 2-methoxy-1-methylethyl, 2-ethoxyethyl, 2-(N,N-dimethylamino)ethyl, 3-(N,N-dimethylamino)propyl, 2-propenyl, 2-propynyl, cyclobutyl, cyclopropylmethyl,

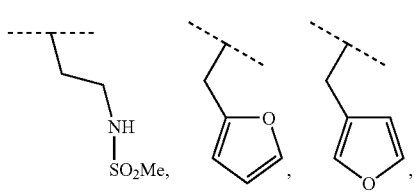

,

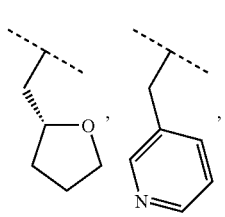

,

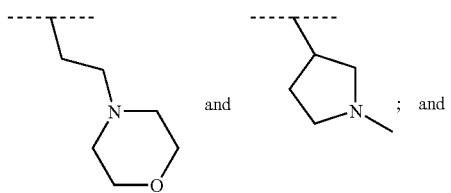

; and $R^6$ is H, methyl, ethyl or fluoro; or
$R^5$ and $R^6$ are linked, together with the atoms to which they are attached, to form a 6-membered ring, such that the group of the subformula

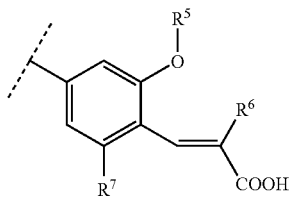

is a group of formula

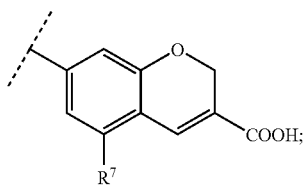

$R^7$ is H or methoxy; and
the group

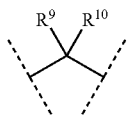

is selected from:

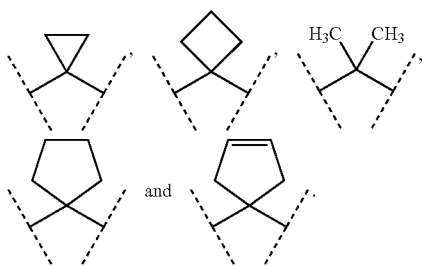

In a most preferable embodiment are provided compounds of formula Ia:

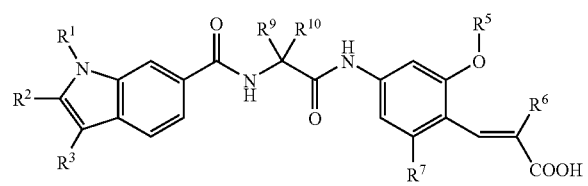

wherein
$R^1$ is methyl;

$R^2$ is selected from:

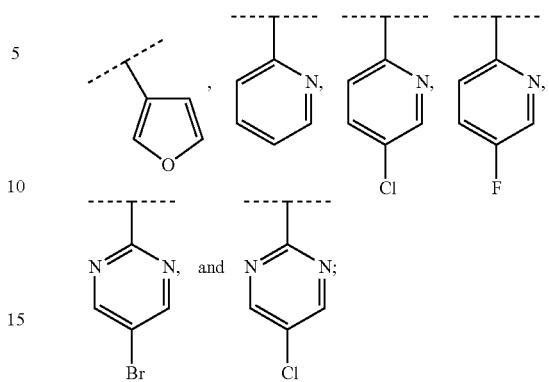

$R^3$ is cyclopentyl;
$R^5$ is ethyl or 2-methoxyethyl;
$R^6$ is H;
$R^7$ is H; and
the group

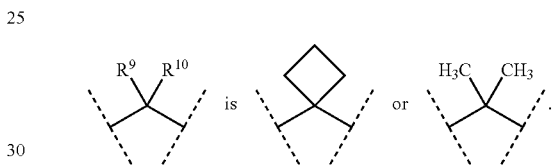

In an alternative most preferable embodiment are provided compounds of formula Ib:

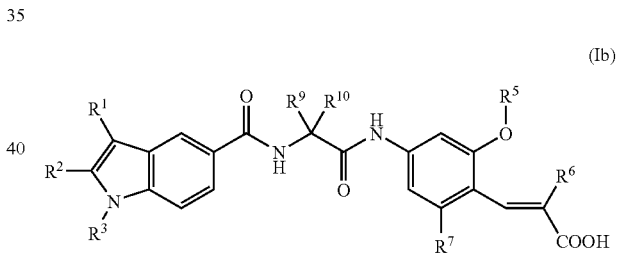

wherein
$R^1$ is methyl;
$R^2$ is selected from:

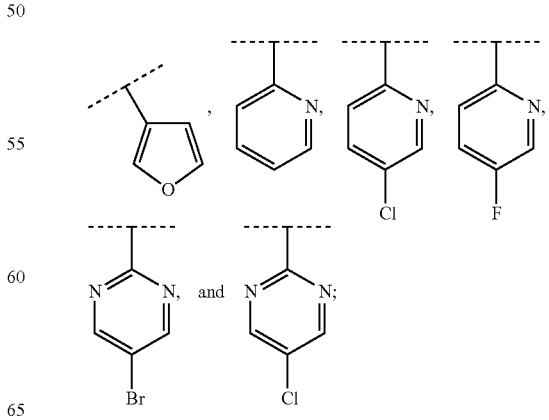

$R^3$ is cyclohexyl;

$R^5$ is ethyl or 2-methoxyethyl;
$R^6$ is H;
$R^7$ is H; and
the group

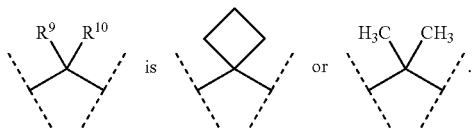

Included within the scope of this invention is each single compound of formula (I) as presented in Tables 1 to 5.

Polymerase Activity

The ability of the compounds of formula (I) to inhibit RNA synthesis by the RNA dependent RNA polymerase of HCV can be demonstrated by any assay capable of measuring HCV RNA dependent RNA polymerase activity. A suitable assay is described in the examples.

Specificity for RNA Dependent RNA Polymerase Activity

To demonstrate that the compounds of the invention act by specific inhibition of HCV polymerase, the compounds may be tested for inhibitory activity in an assay measuring the activity of an RNA-dependent RNA polymerase other than HCV polymerase or in a DNA dependent RNA polymerase assay.

Cell-based HCV RNA Replication Activity

The ability of the compounds of the invention to inhibit the replication of HCV RNA in cell culture may be demonstrated by testing the compounds for inhibitory activity in a cell-based HCV replication assay. A suitable assay is described in the examples.

When a compound of formula (I), or one of its therapeutically acceptable salts or esters, is employed as an antiviral agent, it can be administered orally, topically or systemically to mammals, including, but not limited to, humans, cattle, pig, dogs, cats, rabbits or mice, in a vehicle comprising one or more pharmaceutically acceptable carriers, the proportion of which is determined by the solubility and chemical nature of the compound, chosen route of administration and standard biological practice.

For oral administration, the compound or a therapeutically acceptable salt or ester thereof can be formulated in unit dosage forms such as capsules or tablets each containing a predetermined amount of the active ingredient, ranging from about 1 to about 500 mg, in a pharmaceutically acceptable carrier.

For topical administration, the compound can be formulated in pharmaceutically accepted vehicles containing about 0.1 to about 5 percent, preferably about 0.5 to about 5 percent, of the active agent. Such formulations can be in the form of a solution, cream or lotion.

For systemic administration, the compound of formula (I) can be administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers which may be used for the above noted formulations are described in pharmaceutical texts, e.g. in "Remington's The Science and Practice of Pharmacy", 19th ed., Mack Publishing Company, Easton, Pa., 1995, or in "Pharmaceutical Dosage Forms And Drugs Delivery Systems", 6th ed., H. C. Ansel et al., Eds., Williams & Wilkins, Baltimore, Md., 1995.

The dosage of the compound will vary with the form of administration and the particular active agent chosen. Furthermore, it will vary with the particular host under treatment. Generally, treatment is initiated with small increments until the optimum effect under the circumstance is reached. In general, the compound of formula (I) is most desirably administered at a concentration level that will generally afford antivirally effective results without causing any harmful or deleterious side effects.

For oral administration, the compound or a therapeutically acceptable salt or ester can be administered in the range of about 0.01 to about 200 mg per kilogram of body weight per day, with a preferred range of about 0.05 to about 100 mg per kilogram.

For systemic administration, the compound of formula (I) can be administered at a dosage of about 0.01 mg to about 100 mg per kilogram of body weight per day, although the aforementioned variations will occur. A dosage level that is in the range of from about about 0.05 mg to about 50 mg per kilogram of body weight per day is most desirably employed in order to achieve effective results.

When the compositions of this invention comprise a combination of a compound of formula (I) and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts or esters are formulated together with a pharmaceutically acceptable carrier, the resulting composition may be administered in vivo to mammals, such as man, to inhibit HCV polymerase or to treat or prevent HCV virus infection. Such treatment may also be achieved using the compounds of this invention in combination with agents which include, but are not limited to: immunomodulatory agents, such as α-, β-, or γ-interferons or pegylated forms thereof; other antiviral agents such as ribavirin, amantadine; other inhibitors of HCV NS5B polymerase; inhibitors of other targets in the HCV life cycle, which include but are not limited to, agents that inhibit a target selected from a helicase, a NS2/3 protease and an internal ribosome entry site (IRES) and agents that interfere with the function of other viral targets including but not limited to an NS5A protein; or combinations thereof. The additional agents may be combined with the compounds of this invention to create a single dosage form. Alternatively these additional agents may be separately administered to a mammal as part of a multiple dosage form.

Methodology and Synthesis

The synthesis of compounds according to this invention is preferably accomplished following the general procedure outlined in Scheme 1 below.

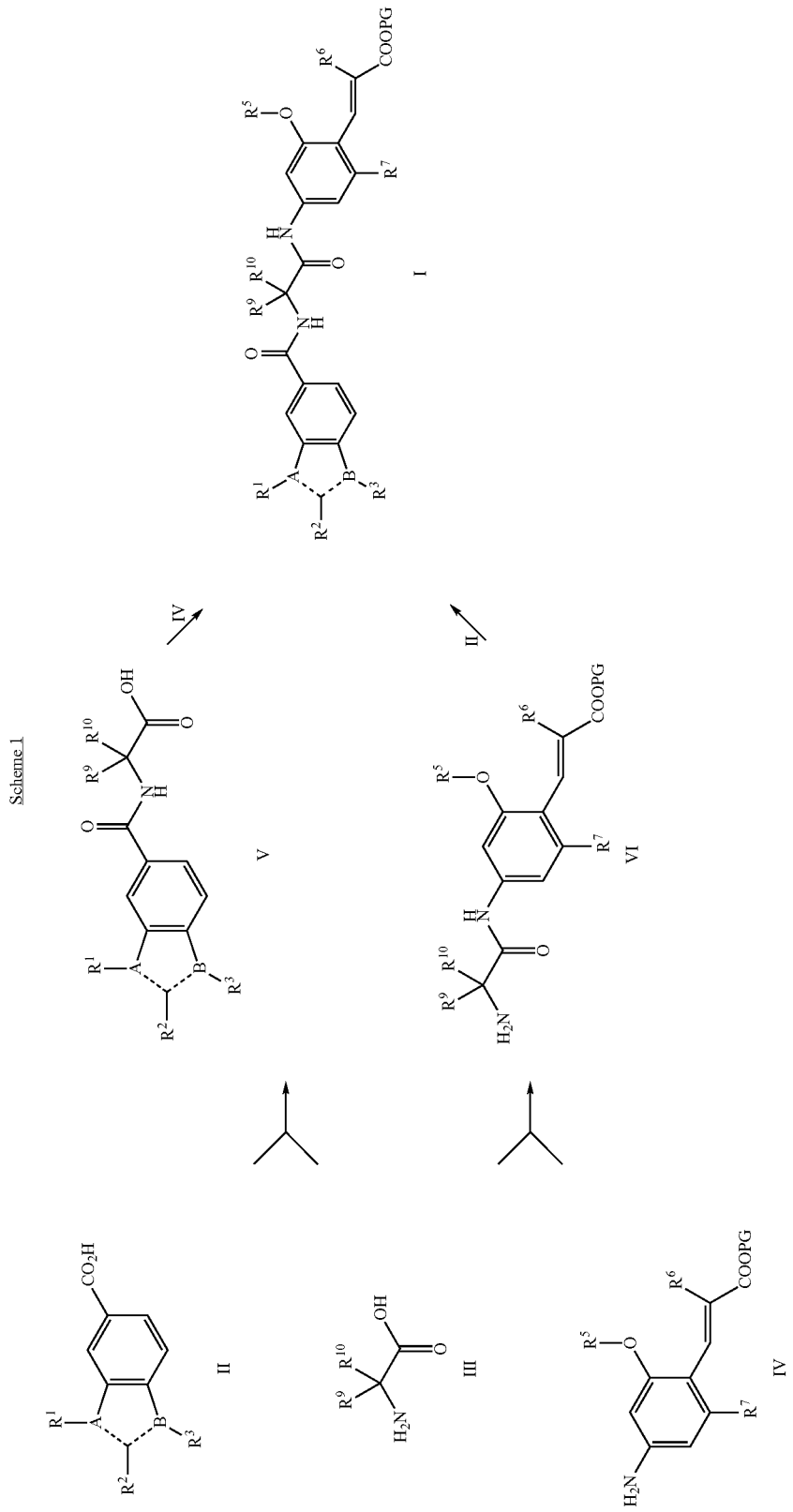

Compounds of formula I, wherein $R^1$, $R^2$, $R^3$, $R^5$, $R^6$, $R^7$, $R^9$, and $R^{10}$ are defined as hereinbefore, are preferably prepared by coupling carboxylic acids of general formula II, disubstituted amino acids of general formula III and anilines of general formula IV, wherein $R^1$, $R^2$, $R^3$, $R^5$, $R^6$, $R^7$, $R^9$, and $R^{10}$ are defined as hereinbefore and PG is H or an ester protecting group, as illustrated in Scheme 1 above. The fragments II, III and IV may be coupled so that fragments III and IV are coupled to give an amine of formula VI, which is subsequently coupled to the acid fragment II to give a product of formula. Alternatively, the fragments II and III may be coupled to give a carboxylic acid of formula V, which may then be coupled to fragment IV. It will be apparent to one skilled in the art that in the case when the amino group of fragment III is coupled to the carboxyl group of fragment II, the carboxyl group of fragment III may be protected prior to coupling with a suitable carboxyl protecting group which will subsequently be removed, using standard procedures, to give fragment V. Suitable carboxyl protecting groups are well known and include, but are not limited to, ester protecting groups such as methyl and ethyl esters. As well, in the case when the amino group of fragment IV is coupled to the carboxyl group of fragment III, the amino group of fragment III may be protected prior to coupling with a suitable amino protecting group, which will subsequently be removed, using standard procedures, to give fragment VI. Suitable amino protecting groups are also well known and include, but are not limited to, the tert-butyloxycarbonyl group (BOC).

The coupling is generally effected using carboxyl-activating reagents well known by those skilled in the art, including, but not limited to, TBTU, HATU, BOP, BrOP, EDAC, DCC, isobutyl chloroformate and the like. Alternatively, carboxylic acids of general formula 11 may be converted to the corresponding acid chlorides using standard reagents, then coupled with amine derivatives of the general formula VI. As well, carboxylic acids of formula V may be treated with a reagent such as acetic anhydride to form an azalactone intermediate which reacts with an aniline of formula IV to form an inhibitor of formula I. In the cases where PG is an ester protecting group, a saponification reaction is carried out (using protocols well known by those skilled in the art) to obtain the final inhibitor product of formula I as the free carboxylic acid.

Intermediate carboxylic acids of formula II may be prepared by procedures described in WO 03/010141, or by procedures described in the examples below.

Intermediate amines of formula VI may be prepared by coupling amino acids of formula III or suitable derivatives thereof with aniline derivatives of general formula IV by procedures described in WO 03/010141, or by procedures described in the examples below. For example, the nitrogen functionality of amino acids of formula III can be protected using standard N-protecting groups well known to those skilled in the art, such as Boc, CBz, Fmoc or other types of carbamates, and the carboxylic acid group can then be activated for coupling to anilines of formula IV. Such activating procedures are well known to those skilled in the art and may include, but are not limited to, such reagents as TBTU, HATU, BOP, BrOP, EDAC, DCC, isobutyl chloroformate and the like. Alternatively, amino acids of formula III may be converted to amino acid chloride hydrochlorides and coupled to anilines of formula IV following procedures such as those described in WO 03/010141.

Anilines of general formula IV can be prepared from the corresponding nitroaryl derivative of formula VII using reducing agents and procedures well known to those skilled in the art (Scheme 2). These include, but are not limited to, metals such as Fe, Sn, Zn and the like, metal salts such as $SnCl_2$, metal-based hydride reagents and sulfur-based reducing agents such as sodium hydrosulfite and the like. Representative procedures for the preparation of anilines of general formula IV or nitro precursors of general formula VII are described in the examples below; modifications thereof to produce other intermediates useful in the synthesis of compounds of formula I will be apparent to those skilled in the art.

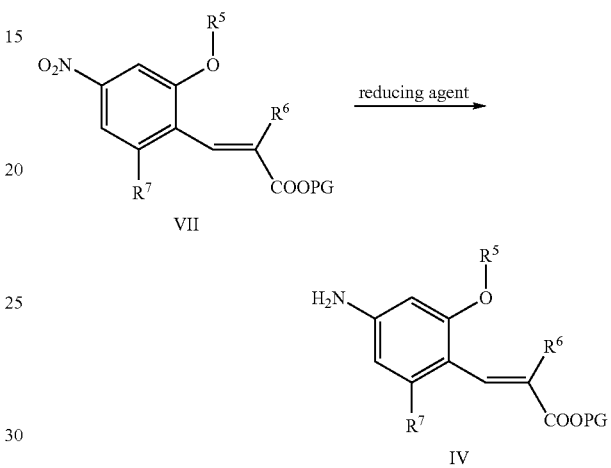

Scheme 2

EXAMPLES

The present invention is illustrated in further detail by the following non-limiting examples. As is well known by a person skilled in the art, reactions are performed in a nitrogen or argon atmosphere where necessary to protect reaction components from air or moisture. Temperatures are given in degrees Celsius. Flash chromatography is performed on silica gel. Solution percentages or ratios express a volume to volume relationship, unless stated otherwise. Mass spectral analyses are recorded using electrospray mass spectrometry. Analytical HPLC was carried out under standard conditions using a Combiscreen ODS-AQ C18 reverse phase column, YMC, 50×4.6 mm i.d., 5 µM, 120 Å at 220 nM, elution with a linear gradient as described in the following table (Solvent A is 0.06% TFA in $H_2O$; solvent B is 0.06% TFA in $CH_3CN$):

| Time (min) | Flow (mL/min) | Solvent A (%) | Solvent B (%) |
| --- | --- | --- | --- |
| 0 | 3.0 | 95 | 5 |
| 0.5 | 3.0 | 95 | 5 |
| 6.0 | 3.0 | 50 | 50 |
| 10.5 | 3.5 | 0 | 100 |

Hereinbefore and hereinafter the following abbreviations or symbols are used:
AcOH: acetic acid;
$Ac_2O$: acetic anhydride;
BOC or Boc: tert-butyloxycarbonyl;
BOP: benzotriazole-1-yloxy-tris(dimethylamino)phosphonium hexafluorophosphate;

BroP: Bromo tris(dimethylamino)phosphonium hexafluorophosphate;
Bu: butyl;
CPS: counts per second;
DAST: (diethylamino)sulfur trifluoride;
DCC: 1,3-Dicyclohexyl carbodiimide;
DCM: dichloromethane;
DIBAL-H: di-iso-butylaluminum hydride
DMEM: Dulbecco's Modified Earle Medium;
DMF: N,N-dimethylformamide;
DMSO: dimethylsulfoxide;
$EC_{50}$: 50% effective concentration;
EDAC: see EDC;
EDC: 1-(3-dimethylaminopropyl)-3-ethyl carbodiimide hydrochloride;
ES⁻: electro spray (negative ionization);
ES⁺: electro spray (positive ionization);
Et: ethyl;
$Et_2O$: diethyl ether;
EtOAc: ethyl acetate;
EtOH: ethanol;
FBS: fetal bovine serum
Fmoc: 9-fluorenylmethoxycarbonyl;
HATU: O-(7-azabenzotriazol-1-yl)-N,N,N',N'-tetramethyluronium hexafluorophosphate;
HBTU: O-Benzotriazol-1-yl-N,N,N',N'-tetramethyluronium hexafluorophosphate;
HOAT: 1-hydroxy-7-azabenzotriazole;
HOBt: 1-Hydroxybenzotriazole;
HPLC: high performance liquid chromatography;
ⁱPr or i-Pr: iso-propyl;
Me: methyl;
MeCN: acetonitrile;
MeOH: methanol;
MS (ES): electrospray mass spectrometry;
NMP: N-methyl-2-pyrrolidinone;
NMR: nuclear magnetic resonance spectroscopy;
PBS: phosphate buffer saline;
Ph: phenyl;
PG: protecting group;
Pr: propyl;
PVDF: polyvinylidene fluoride;
RT: room temperature (approximately 25° C.);
TBME: tert-butylmethyl ether;
TBTU: 2-(1H-benzotriazol-1-yl)-N,N,N',N'-tetramethyluronium tetrafluoroborate;
tBu: tert.-butyl;
Tf: trifluoromethylsulfonyl;
TfO: trifluoromethylsulfonate;
TFA: trifluoroacetic acid;
THF: tetrahydrofuran;
TLC: thin layer chromatography;
TMS: trimethylsilyl;
Troc: trichloroethoxycarbonyl.

Example 1

3-(3,3-Difluorocyclopentyl)-1-methyl-1H-indole-6-carboxylic acid methyl ester

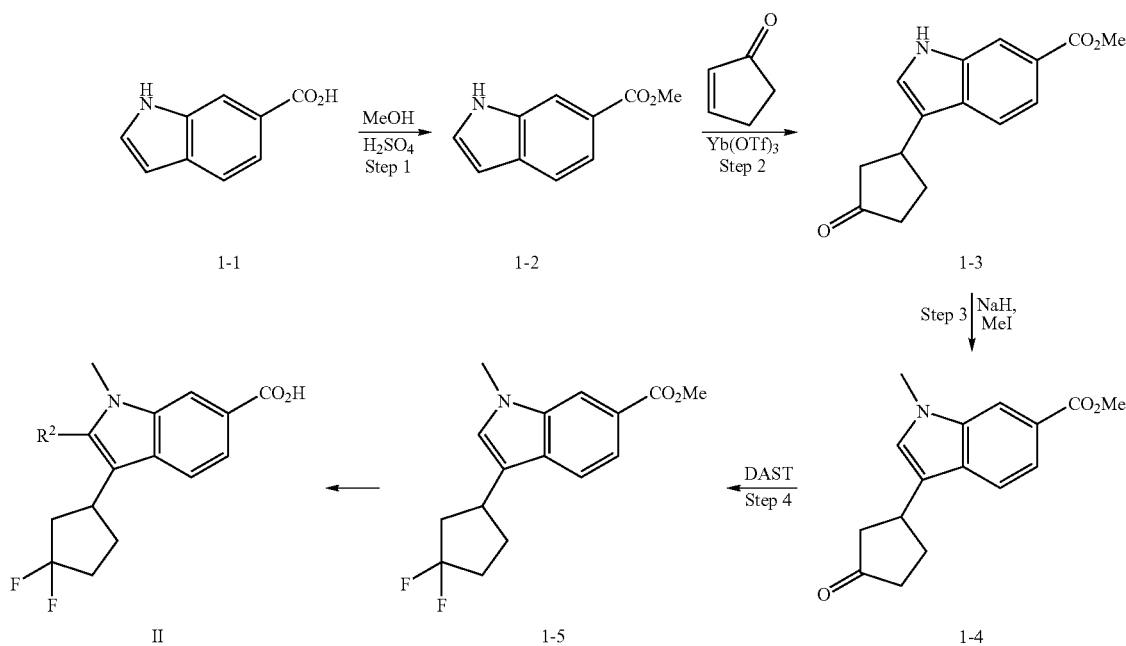

Step 1:

Indole-6-carboxylic acid 1-1 (5.0 g, 31.0 mmol) was dissolved in MeOH (100 mL), a catalytic amount of $H_2SO_4$ (1.0 mL) was added and the reaction mixture was stirred at reflux for 16 h. A small amount of solid $K_2CO_3$ was added, in order to neutralize the excess $H_2SO_4$, and stirring was continued at RT for 1 h. The reaction mixture was concentrated under vacuum to remove the MeOH, diluted with saturated aqueous $NaHCO_3$ (~50 mL) and extracted with EtOAc (~200 mL). The organic layer was washed with brine (100 mL), dried over anhydrous $MgSO_4$ and concentrated to dryness. The resulting residue was purified by flash column chromatography, using 30% EtOAc in hexane as the eluent, to obtain the pure methyl ester 1-2 (4.78 g, 88% yield).

Step 2:

The methyl ester 1-2 from step 1 (3.31 g, 18.9 mmol) was dissolved in MeCN (50 mL) and a catalytic amount of Yb(OTf)$_3$ (586 mg, 0.95 mmol) was added. 2-Cyclopenten-1-one (7.76 mL, 94.5 mmol) was added and the reaction mixture was stirred at reflux for 16 h. The MeCN solvent was removed under vacuum, the residue was re-dissolved in EtOAc (~200 mL) and extracted with aqueous saturated NaHCO$_3$ (~100 mL), H$_2$O (50 mL) and brine (50 mL). The organic layer was dried over anhydrous MgSO$_4$ and concentrated to dryness under vacuum. After purification of the residue by flash column chromatography, using 40% EtOAc in hexane as the solvent gradient, the desired cyclopentanone adduct 1-3 was isolated as isolated as a beige-colored powder (3.4 g, 70% yield).

Step 3:

To a solution of the cyclopentanone adduct intermediate 1-3 from step 2 (3.81 g, 14.8 mmol) in anhydrous DMF (150 mL) at 0° C., NaH (60% in oil, 770 mg, 19.2 mmol) was added slowly. The reaction mixture was stirred at 0° C. for 5 min, then MeI (1.2 mL, 19.2 mmol) was added drop-wise and stirring was continued at 0° C. for 3 h. The mixture was allowed to warm-up to RT and was quenched by the addition of aqueous saturated NH$_4$Cl (200 mL). The mixture was extracted with EtOAc (2×500 mL) and the organic layer was washed with aqueous saturated NH$_4$Cl (2×200 mL) H$_2$O (200 mL) and brine (200 mL). The combined organic layers were dried over anhydrous MgSO$_4$, evaporated to dryness and the residue was purified by flash column chromatography (using 30% EtOAc in hexane as the eluent) to isolate the N-methylindole intermediate 1-4 as a beige solid (3.1 g, 77% yield).

Step 4:

In a sealed tube, the N-methylindole intermediate 1-4 from step 3 (1.4 g, 5.16 mmol) and DAST (2.7 mL, 20.6 mmol) were dissolved in CH$_2$Cl$_2$ (50 mL) and stirred at reflux for 3 days. The mixture was poured into aqueous saturated NaHCO$_3$ (~50 mL) and once the evolution of CO$_2$ had stopped, the mixture was extracted with CH$_2$Cl$_2$ (2×100 mL). The combined organic layers were washed with brine (50 mL), dried over anhydrous MgSO$_4$ and concentrated to dryness. The residue was purified by flash column chromatography (using a solvent gradient from 10% to 20% EtOAc in hexane) to isolate 3-(3,3-difluorocyclopentyl)-1-methyl-1H-indole-6-carboxylic acid methyl ester 1-5 (750 mg, 50% yield).

3-(3,3-Difluorocyclopentyl)-1-methyl-1H-indole-6-carboxylic acid methyl ester 1-5 is converted to carboxylic acid intermediates of formula 11, wherein R$^1$ is methyl, R$^2$ is defined as hereinbefore and R$^3$ is 3,3-difluorocyclopentyl, using procedures described in WO 03/010141. These intermediates may be converted to compounds of general formula I using procedures illustrated in Scheme 1 above and described in WO 03/010141.

Example 2

2-Bromo-3-(4,4-difluorocyclohexyl)-1-methyl-1H-indole-6-carboxylic acid methyl ester

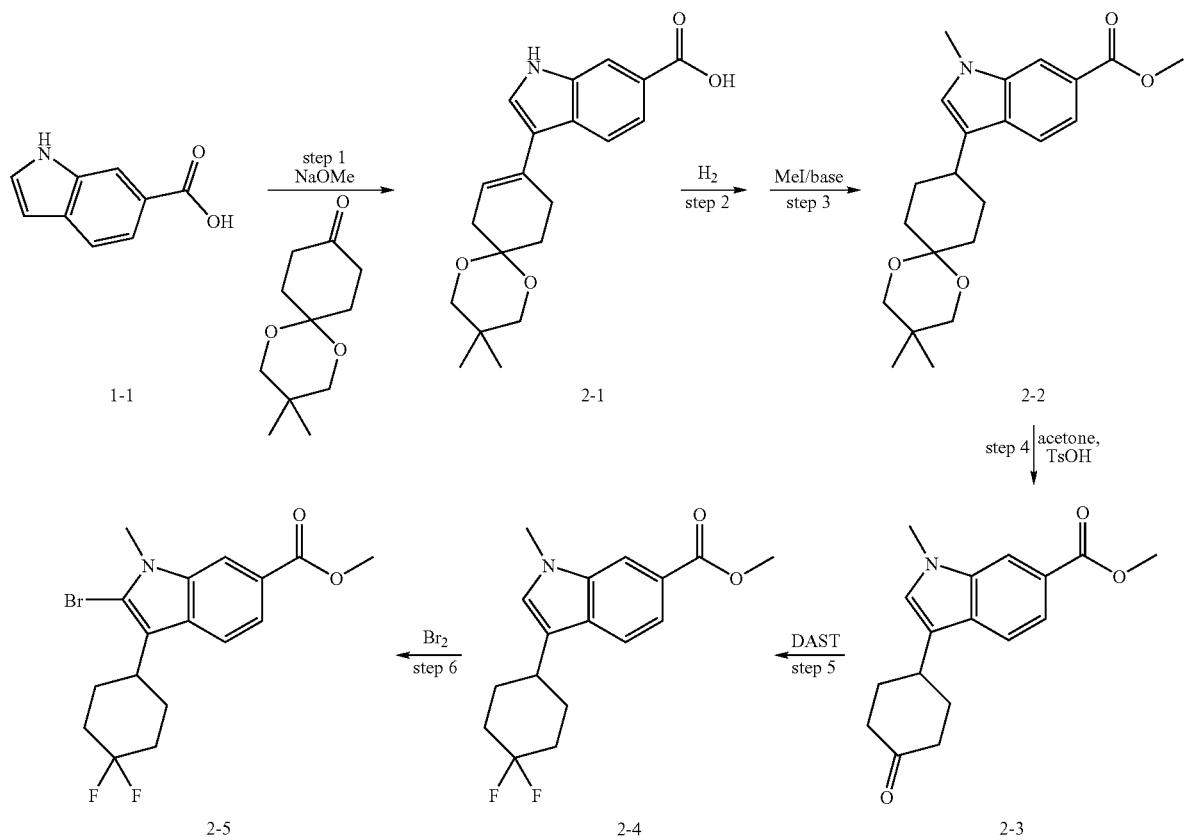

Step 1:

Indole 6-carboxylic acid 1-1 (10.0 g, 62 mmol) was dissolved in dry MeOH (200 mL) and 1,4-cyclohexanedione-mono-2,2-dimethyltrimethylene ketal (16.4 g, 81 mmol, 1.3 equivalent) was added. NaOMe (0.25 M in MeOH, 110 mL) was added and the mixture was refluxed for 48 h. The reaction mixture was then diluted with water (200 mL) and the MeOH removed under reduced pressure. Additional water (200 mL) was added to the residue and the mixture was stirred at 45° C. for 30 min to dissolve most solids. The solution was filtered to remove some insoluble material and the filtrate was acidified with formic acid to neutral pH (~10 mL). The precipitated solid was collected by filtration, washed with water (500 mL) and hexane (200 mL) and dried in vacuum to give the desired alkylated indole 2-1 as an off-white solid (23 g).

Step 2:

The indole 2-1 from Step 1 (35.5 g) was suspended in a mixture of THF (300 mL) and MeOH (300 mL) and hydrogenated over 20% Pd(OH)$_2$/C (0.76 g) at 55 psi for 5 h. Additional catalyst was added (0.56 g) and hydrogenation resumed overnight. A third portion of catalyst (0.36 g) had to be added to complete the reaction (3–4 h). The catalyst was then removed by filtration using 1:1 MeOH-THF (1.3 L) for rinses and the filtrate evaporated under reduced pressure (34 g, 96% yield).

Step 3:

The indole carboxylic acid derivative from step 2 (34.3 g, 0.1 mole) was dissolved in dry NMP (300 mL) and K$_2$CO$_3$ (30.4 g, 0.22 mole, 2.2 equivalents) was added. Dimethyl carbonate (42 mL, 0.5 mole, 5 equivalents) was added and the mixture heated to 140° C. overnight. The black mixture was cooled to room temperature and then in an ice bath and was quenched by dropwise addition of water (250 mL), maintaining an internal temperature <10° C. H$_3$PO$_4$ was then added dropwise in the cold to acidify the mixture to pH 4 (~40 mL). After stirring for an additional 1 h in the cold, the brown solid was collected by filtration, washed with water (~500 mL) and then hexane (3×30 mL). The material was purified by flash chromatography on silica gel using 5% to 40% EtOAc in hexane as eluent. The desired product 2-2 was obtained as a white solid (23 g).

Step 4:

The ketal 2-2 from Step 3 (17 g, 46 mmol) was dissolved in acetone (1.5 L) and para-toluenesulfonic acid (0.87 g) was added. The yellow solution was stirred overnight at room temperature and then refluxed for 10 h to complete the hydrolysis. Volatiles were removed under reduced pressure and the residue purified by flash chromatography on silica gel using 0% to 30% EtOAc in hexane. The desired ketone 2-3 was obtained as a white solid (11.5 g).

Step 5:

The ketone 2-4 from Step 4 (5.75 g, 20.2 mmol) was dissolved in dry DCM (115 mL) in a 200 mL pressure tube. The system was purged with argon and DAST (9.05 mL, 68.5 mmol, 3.4 equivalents) was added. The tube was sealed and heated to 50° C. for 50 h. After cooling in an ice bath, the reaction was quenched by dropwise addition of NaHCO$_3$ solution (~1 L) and the product was extracted with EtOAc (1 L). The extract was washed with water (500 mL) and brine (300 mL) and dried (Na$_2$SO$_4$). Removal of solvent gave a residue that was purified by flash chromatography on silica gel using 0% to 40% EtOAc in hexane. The product 2-4 was obtained as a white solid after trituration with hexane (12.2 g for two runs).

Step 6:

The indole 2-4 from Step 5 (10.00 g, 33 mmol) was dissolved in a mixture of THF (100 mL) and CHCl$_3$ (100 mL). The mixture was cooled in an ice-salt bath to 0° C. and pyridinium tribromide (14.26 g, 45 mmol, 1.37 equivalent) was added. After stirring for 3 h in the cold, the reaction mixture was quenched by addition of water (50 mL) and solvents removed under reduced pressure. The residue was partitioned between EtOAc (200 mL) and aqueous NaHCO$_3$ (200 mL). The organic phase was washed with water (2×100 mL) and brine (100 mL) and the aqueous phase back-extracted with another portion of EtOAc (3×50 mL). The combined extracts were dried (Na$_2$SO$_4$) and concentrated to give a yellow solid that was purified by flash chromatography on silica gel using 0% to 10% EtOAc in hexane. A second column using 1–3% EtOAc in hexane followed by DCM was required to further purify the product. The material (11 g) was then triturated twice with 10% ether in hexane (600 mL). The desired bromoindole 2-5 (7.9 g) was obtained as a white solid.

2-Bromo-3-(4,4-difluorocyclohexyl)-1-methyl-1H-indole-6-carboxylic acid methyl ester 2–5 is converted to carboxylic acid intermediates of formula II, wherein R$^1$ is methyl, R$^2$ is defined as hereinbefore and R$^3$ is 3,3-difluorocyclohexyl, using procedures described in WO 03/010141. These intermediates may be converted to compounds of general formula I using procedures illustrated in Scheme 1 above and described in WO 03/010141.

Example 3

3-Cyclopentyl-1-methyl-2-(1H-pyrazol-3-yl)-1H-indole-6-carboxylic acid

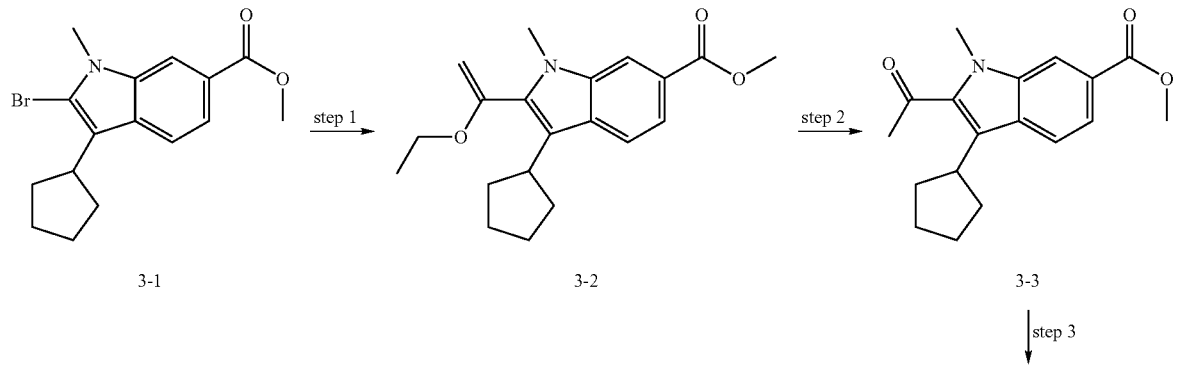

3-1    3-2    3-3 step 3

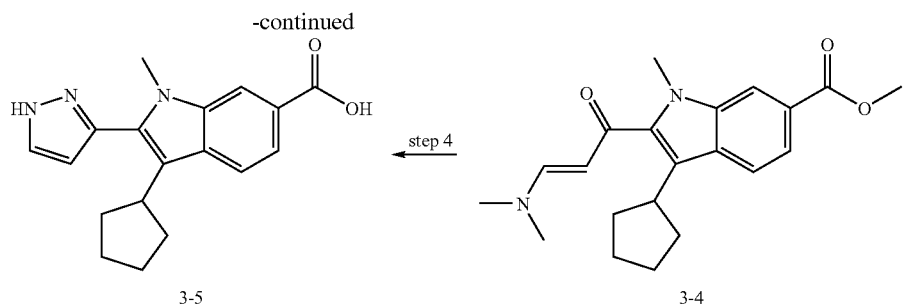

3-5    3-4

Step 1:

The bromoindole 3-1 prepared as described in WO 03/010141 (3.00 g, 8.9 mmol) was dissolved in dioxane (40 mL) and 1-(ethoxyvinyl)tributyltin (3.6 mL, 10.7 mmol, 1.2 equivalent) was added. The solution was degassed with argon and dichlorobis(triphenylphosphine)palladium (0.376 g, 0.5 mmol, 0.06 equivalent) was added. The mixture was stirred at 120° C. overnight. The reaction mixture was cooled to room temperature, diluted with EtOAc and concentrated under reduced pressure to remove dioxane. The residue was purified by flash chromatography on silica gel using 0% to 2% EtOAc in hexane as eluent. The ethoxyvinylindole 3-2 was obtained as a yellow oil (2.50 g, 86% yield).

Step 2:

The derivative 3-2 from Step 1 (2.50 g, 7.6 mmol) was dissolved in EtOAc (80 mL) and 2N HCl (50 mL) was added. The biphasic mixture was vigorously stirred for 2.5 h, at which point TLC indicated complete conversion to the 2-acetylindole. The organic phase was separated and washed with NaHCO$_3$ (100 mL) and brine (30 mL). The solution was dried (Na$_2$SO$_4$) and concentrated to give a yellow solid. Trituration with hexane gave the desired product 3-3 as an off-white solid (1.50 g, 65% yield).

Step 3:

The acetylindole 3-3 derivative from step 2 (0.45 g, 1.5 mmol) was dissolved in toluene (15 mL) and N,N-dimethylformamide dimethyl acetal (0.60 mL, 4.5 mmol, 3 equivalents) was added. The mixture was heated to 100° C. in a sealed tube for 5 h. Another portion of N,N-dimethylformamide dimethyl acetal (0.60 mL, 4.5 mmol, 3 equivalents) was added and heating was resumed for another 20 h. The reaction mixture was cooled to room temperature and volatiles removed under vacuum. The residue was co-evaporated with ether, yielding a beige foam 3-4 (0.55 g) that was used directly in the next step.

Step 4:

Following the procedure of Kikelj et al. (*Bioorg. Med. Chem. Lett.* 2003, 13, 789), the crude material 3-4 from Step 3 (106 mg, 0.30 mmol) was dissolved in EtOH (4 mL) and hydrazine monohydrate (47 µL, 1.5 mmol, 5 equivalents) was added. The mixture was then stirred overnight at room temperature. The reaction was diluted with THF (4 mL) and 5N LiOH (0.3 mL) was added. The mixture was stirred at 50° C. for 5 h after which saponification of the methyl ester was complete. Volatiles were removed under reduced pressure and the residue acidified with 1N HCl. The indole derivative was extracted into EtOAc and washed with water and brine. The extract was dried (MgSO$_4$) and solvents evaporated to give the desired pyrazole-indole 3-5 (75 mg) as an oil.

3-Cyclopentyl-1-methyl-2-(1H-pyrazol-3-yl)-1H-indole-6-carboxylic acid 3-5 is converted to inhibitors of formula I, wherein R$^1$ is methyl, R$^2$ is 1H-pyrazolyl-3-yl and R$^3$ is cyclopentyl, using procedures illustrated in Scheme 1 above and described in WO 03/010141.

Example 4

3-(4-Amino-2-ethoxyphenyl)acrylic acid methyl-ester

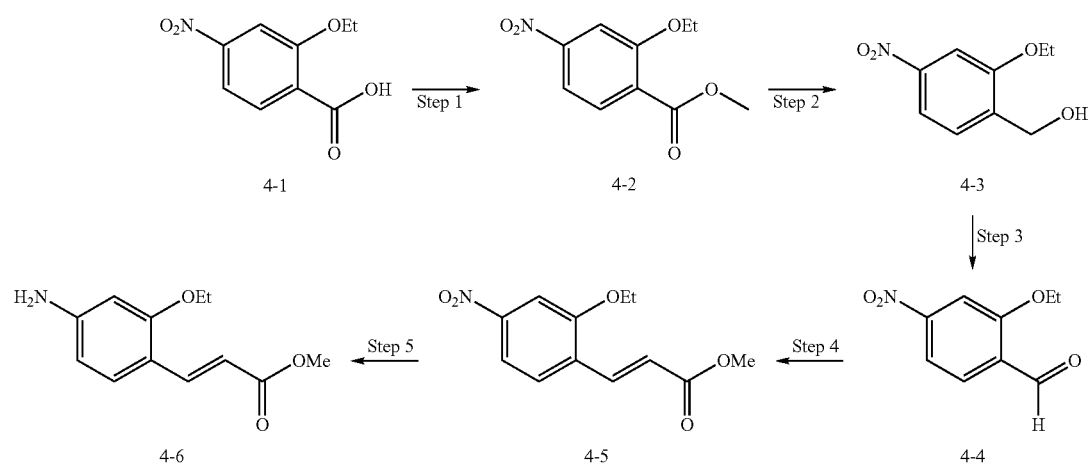

Step 1:

2-Ethoxy-4-nitrobenzoic acid 4-1 (1.56 g; 7.38 mmol) was dissolved in methanol (15 mL) and the resulting solution stirred at 0° C. A solution of diazomethane in ethyl ether was slowly added until the yellow color persisted and the mixture was stirred for a further 20 min. The solvents were evaporated to afford the methyl ester 4-2 as a pale yellow solid (1.66 g, quant.) which was used without further purification.

Step 2:

The ester 4-2 from above (1.60 g; 7.10 mmol) was dissolved in dry toluene and the solution cooled to −78° C. under a nitrogen atmosphere. A solution of diisobutylaluminum hydride in tetrahydrofuran (1M; 8 mL; 8 mmol) was added and the reaction allowed to warm to ambient temperature. Two additional portions of DIBAL-H were added in this way (7 and 10 mL) after 1 h and a further 1.5 h. 0.5 h after the last addition, the reaction was cooled to 0° C. and 1N HCl (25 mL) was slowly added and the mixture stirred vigorously for 0.5 h. The organic solvents were then evaporated and the aqueous residue was extracted with ethyl acetate (2×50 mL) and washed with water (50 mL) and brine (50 mL). The combined extracts were then dried over $MgSO_4$ and evaporated to afford the alcohol 4-3 as a pale yellow, fibrous solid (1.40 g; quant.) which was used as such.

Step 3:

A turbid solution of 1,1,1-tris(acetyloxy-1,1-dihydro-1,2-benzodioxol-3-(1H)-one (Dess-Martin periodinane) (2.32 g; 5.47 mmol) in dichloromethane (40 mL+5 mL rinse) was added to a stirred solution of the above alcohol 4-3 (0.98 g; 4.97 mmol) in DCM (40 mL) and the reaction stirred at ambient temperature under a nitrogen atmosphere. After 4 h, saturated $NaHCO_3/10\%$ $Na_2S_2O_3$ (1:1, 160 mL) was added and the mixture stirred vigorously until the phases were clear (ca. 0.5 h). The organic phase was separated and the aqueous phase was extracted with dichloromethane (50 mL) and washed with saturated $NaHCO_3$ (2×150 mL). The combined organic phases were then dried over $MgSO_4$ and evaporated to yield the aldehyde 4-4 as a pale yellow solid (960 mg; 99%) which was used as such.

Step 4:

Sodium hydride (95% dry powder; 158 mg; 6.25 mmol) was suspended in anhydrous THF (10 mL) and trimethyl phosphonoacetate (0.945 mL; 5.84 mmol) added dropwise at 0° C. under a nitrogen atmosphere resulting in a solid white mass which could not be stirred. A solution of the aldehyde 4-4 from above (950 mg; 4.87 mmol) in THF (7 mL+3 mL rinse) was then added dropwise resulting in a yellow colour and slow dissolution of the white solid mass. After the addition, the reaction was allowed to warm to ambient temperature. After 15 h, the cloudy reaction mixture was evaporated to a pale yellow solid which was extracted with ethyl acetate (2×50 mL) and washed with saturated $NaHCO_3$ (3×75 mL). The combined extracts were dried over $MgSO_4$ and evaporated to afford the cinnamate ester 4-5 as pale yellow solid (1.212 g; 99%) which was used without further purification.

Step 5:

The nitro cinnamate 4-5 from above (0,300 g, 1.2 mmol) was suspended in EtOH (12 mL) and water (7.5 mL) and $K_2CO_3$ (0.990 g, 7.16 mmol) and 85% sodium hydrosulfite (1.247 g. 7.16 mmol) were added successively. The mixture was stirred vigorously at room temperature for 1.5 h. It was then diluted with water (10 mL) and the ethanol removed under reduced pressure. The reaction mixture was extracted with EtOAc (2×), washed with water and brine and dried ($MgSO_4$). Removal of the solvent under reduced pressure gave the desired aniline 4-6 as a yellow solid.

Note: the analogous methoxy derivative was prepared in the same manner using commercially available 2-methoxy-4-nitrobenzoic acid as starting material. In addition, by using the appropriate phosphonate reagent and following similar procedures to those described above, one can incorporate groups such as small alkyl (e.g. Me, Et) or halogens (e.g. F) on the olefinic cinnamate carbon atom α- to the carboxylic acid function.

Example 5

(Z)-3-(2-Hydroxy-4-nitrophenyl)acrylic acid methyl ester

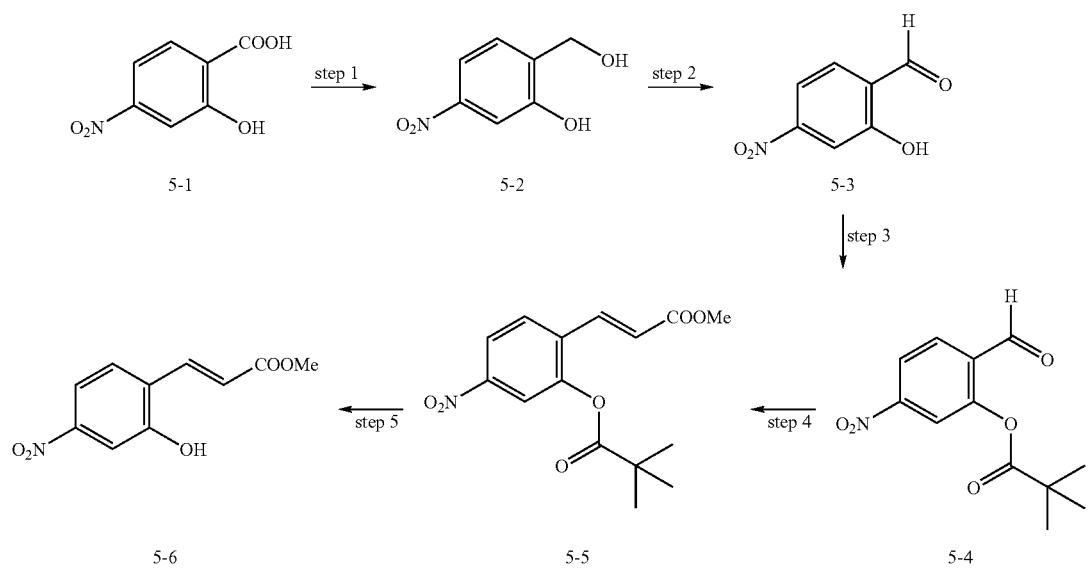

Step 1:

2-Hydroxy-4-nitrobenzoic acid 5-1 (25.74 g, 0.140 mol) was charged in a 1 L 3-necked-flask equipped with a thermometer and addition funnel. Dry THF (400 mL) was transferred into the flask and the solution cooled to −2° C. in an ice-salt bath.

Borane-dimethyl sulfide complex (10 M, 30.9 mL, 0.309 mole, 2.2 equivalents) was added dropwise over 20 min. The reaction mixture was then allowed to warm up to room temperature and stirred overnight. The reaction mixture was then cooled again in an ice-water bath and quenched by careful dropwise addition of water (90 mL) over 30 min. THF was removed under reduced pressure and the residue extracted with EtOAc (2×500 mL). The extract was washed with water (400 mL), 1 N HCl (2×400 mL) and brine (300 mL). After drying ($Na_2SO_4$), volatiles were removed under reduced pressure and the residue was co-evaporated with hexane (3×50 mL) and dried under vacuum. The benzylic alcohol derivative 5-2 was obtained as a yellow solid (22.5 g, 95% yield).

Step 2:

The alcohol 5-2 from step 1 (69.6 g, 0.41 mole) was charged in a 5 L 3-necked flask equipped with a reflux condenser and mechanical stirrer. Chloroform (2.5 L) was added and the mixture heated slowly. Activated $MnO_2$ (85%, 252 g, 2.46 moles, 6 equivalents) was added in small portions over 15 min, during which time, the temperature reached 55–58° C. Reflux was maintained for 1 h, after which TLC analysis indicated complete conversion to the aldehyde. The reaction mixture was cooled to room temperature and filtered through celite using $CHCl_3$ for washings. The yellow filtrate was concentrated under reduced pressure to give aldehyde 5-3 as a a yellow solid that was dried under vacuum (52.11 g, 75% yield).

Step 3:

The aldehyde 5-3 from step 2 (52.0 g, 0.31 mole) was dissolved in DCM (1 L) under an argon atmosphere. Triethylamine (95 mL, 0.68 mole, 2.2 equivalents) was added to the mixture producing a dark red coloration. Trimethylacetyl chloride (40.0 mL, 0.32 mole, 1.05 equivalent) was then added dropwise over 25 min and the reaction mixture stirred for 3 h at room temperature until complete. The mixture was filtered to remove solids (DCM rinses) and the filtrate concentrated under reduced pressure. The residue was diluted with EtOAc and the solution washed with 0.5 M citric acid (500 mL), water (500 mL), $NaHCO_3$ (2×500 mL) and brine (500 mL). After drying ($Na_2SO_4$), volatiles were removed under reduced pressure to yield the desired pivalate 5-4 as an off-white solid (104.2 g).

Step 4:

A 5 L 3-necked flask equipped with a mechanical stirrer and addition funnel was charged with NaH (60% oil dispersion, 19.1 g, 0.478 mole, 1.5 equivalent) under an argon atmosphere. Dry THF (1 L) was added and the mixture cooled in an ice-salt bath to −2° C. Trimethylphosphonoacetate (69.5 g, 0.382 mole, 1.2 equivalent) was added dropwise over 35 min. The thick slurry was stirred for an additional 20 min and the aldehyde 5-4 from step 3 (80.0 g, 0.318 mole) in THF (600 mL) was added over 30 min followed by a THF rinse (400 mL). The orange slurry was then stirred overnight at room temperature. The reaction mixture was quenched with water (50 mL) and THF was removed under reduced pressure. The residue was partitioned between EtOAc (800 mL) and water (800 mL) and the organic phase separated. The aqueous phase was extracted again with EtOAc (1 L) and the organic extracts combined, washed $NaHCO_3$ (2×1 L) and brine (1 L). After drying ($Na_2SO_4$), solvents were removed under reduced pressure until crystallization of the product. After cooling, crystallized material was collected by filtration and washed with cold EtOAc and hexane. After drying, a first crop of product 5-5 (40 g) was obtained as a light yellow solid. Filtrates and washes were combined and concentrated to give an additional 10 g of product (total yield: 50 g).

Step 5:

The cinnamate derivative 5-5 from step 4 (50.0 g, 0.162 mole) was charged into a flask that was immersed in an ice bath. Pre-cooled conc. $H_2SO_4$ (350 mL) was added, producing a dark red solution. After stirring in ice for 30 min, the clear solution was poured over ice (2.5 kg) to give a yellow solid. The material 5-6 was collected by filtration, washed with water and dried (43.6 g).

Note: (E)-3-(2-Hydroxy-4-nitro-phenyl)-2-methyl-acrylic acid ethyl ester (R=Me) was prepared in a similar way replacing trimethylphosphonoacetate by triethyl 2-phosphonopropionate.

Example 6

2-[1-(4-Amino-2-methoxy-phenyl)-meth-(Z)-ylidene]-butyric acid methyl ester

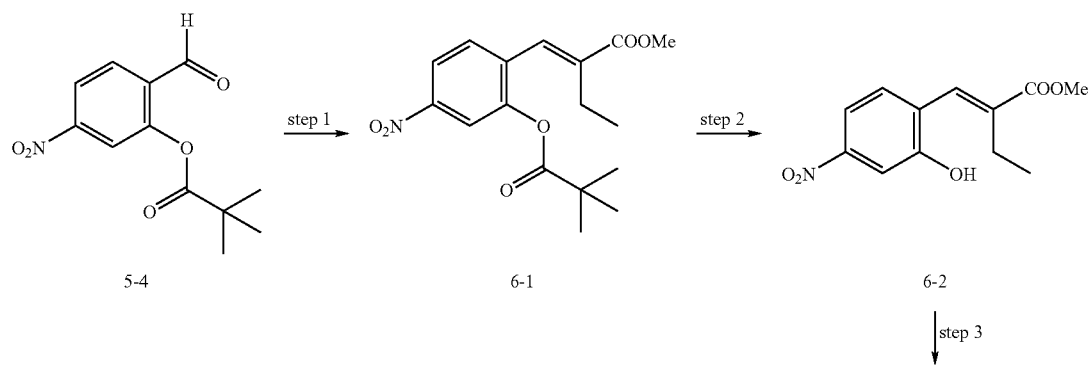

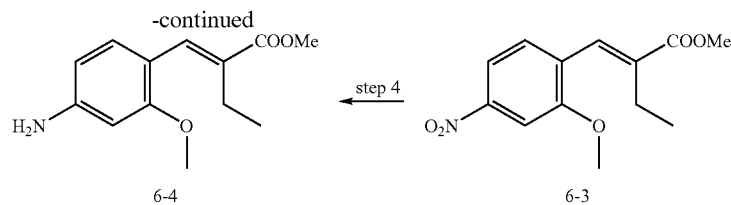

Step 1:

Triethyl-2-phosphonobutyrate (10.16 g, 40.3 mmol, 1.2 equivalent) was charged in a flask under an argon atmosphere and dissolved in dry THF (200 mL). The solution was cooled in an ice bath and NaH (60% dispersion, 1.764 g, 44 mmol, 1.3 equivalent) was added in small portions over 10 min. The mixture was stirred for an additional 1 h at 0° C. and a solution of the aldehyde 5-4 from step 3 of Example 5 (8.44 g, 33.6 mmol) in THF (40 mL) was added dropwise over 15 min. The ice bath was removed and the mixture stirred at room temperature for 70 min after which the reaction was judged to be complete by TLC. THF was removed under reduced pressure and the residue was diluted with EtOAc (300 mL). The solution was washed with NaHCO$_3$ (2×140 mL), 10% aqueous HCl (60 mL) and brine (60 mL). After drying (Na$_2$SO$_4$), volatiles were removed under reduced pressure to give crude product 6-1 (14.0 g).

Step 2:

The crude material 6-1 from step 1 (14.0 g, assume 40 mmol) was treated with conc. H$_2$SO$_4$ (90 mL) as described in step 5 of Example 5. After completion, the reaction mixture was poured on ice resulting in the formation of an oil. The material was extracted into EtOAc and washed with water (3×125 mL) and brine (90 mL). After drying (Na$_2$SO$_4$), the solvent was removed under reduced pressure and the residue purified by flash chromatography on silica gel to give compound 6-2.

Step 3:

The material 6-2 from above (1.20 g, 4.53 mmol) was dissolved in DMF (24 mL) and CS$_2$CO$_3$ (2.95 g, 9.05 mmol, 2 equivalents) was added. After stirring for 15 min, MeI (0.95 g, 6.73 mmol, 1.5 equivalent) was added to the red solution and the mixture was stirred for 1.5 h. Water (80 mL) was added to the reaction mixture, producing a precipitate. The material was collected by filtration, washed with water and dried to give compound 6-3 (1.01 g, 80% yield).

Step 4:

The nitro derivative 6-3 from step 3 (1.00 g, 3.58 mmol) was suspended in a mixture of EtOH (15 mL) and water (4 mL). Iron powder (0.61 g, 10.8 mmol, 3 equivalents) and NH$_4$Cl (0.102 g, 1.91 mmol, 0.52 equivalent) were added and the mixture was stirred at 85° C. for 1 h. The reaction was then cooled to room temperature and filtered through a pad of celite using 1:1 EtOH-DCM (100 mL) for washes. Volatiles were removed under reduced pressure and the residue dissolved in DCM (40 mL). The solution was washed with water (2×15 mL) and brine (15 mL), dried (Na$_2$SO$_4$) and concentrated. The crude product 6-4 was purified by flash chromatography on silica gel using 20% EtOAc in hexane as eluent (0.89 g, 90% yield).

Example 7

2-[1-(4-Amino-2-ethoxy-phenyl)-meth-(E)-ylidene]-butyric acid ethyl ester

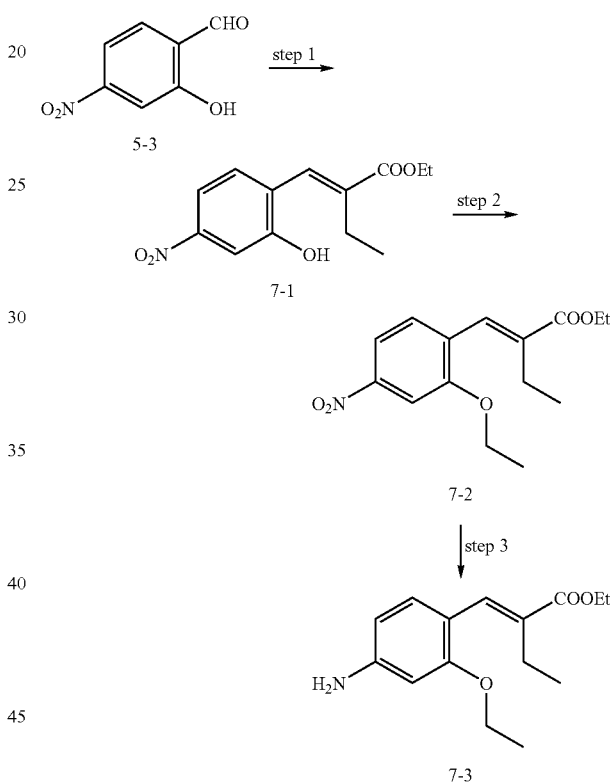

Step 1:

Triethyl-2-phosphonobutyrate (2.52 g, 9.99 mmol, 2 equivalents) was dissolved in dry THF (15 mL) and the solution cooled in an ice bath. NaH (60% dispersion, 0.41 g, 10.2 mmol, 2.0 equivalents) was added in small portions and the white suspension stirred in the ice bath for 1 h. The hydroxyaldehyde 5-3 from step 2 of Example 5 (0.832 g, 5.0 mmol) in THF (10 mL) was added dropwise over 5 min and the ice bath removed. The mixture was stirred for 20 h at room temperature, after which it was judged to be ~60% complete. The reaction mixture was concentrated under reduced pressure, diluted with EtOAc (40 mL) and washed with NaHCO$_3$ (2×20 mL), 10% HCl (10 mL) and brine (10 mL). The organic layer was dried (Na$_2$SO$_4$), evaporated and the residue purified by flash chromatography to give the desired nitrocinnamate ester (0.365 g, 41% yield).

Note: 2-[1-(2-Hydroxy-4-nitro-phenyl)-meth-(Z)-ylidene]-butyric acid ethyl ester was prepared in a similar fashion by replacing triethyl-2-phosphonobutyrate by triethyl-2-phosphonopropionate.

Step 2:

The phenol derivative 7-1 from above (1.01 g, 3.81 mmol) was dissolved in dry DMF (20 mL) and $Cs_2CO_3$ (2.48 g, 7.62 mmol, 2 equivalents) was added. After stirring for 15 min, iodoethane (0.89 g, 5.66 mmol, 1.5 equivalent) was added via syringe and the mixture was stirred for 1.25 h at room temperature, at which point it was judged to be complete (TLC). Water (70 mL) was added to the reaction mixture, producing a white precipitate. The material was collected by filtration, washed with water and dried to give compound 7-2 (1.11 g, 88% yield).

Note: replacing iodoethane by iodomethane gave the corresponding methoxy analog.

Step 3:

The nitrocinnamate derivative 7-2 of step 2 was reduced to the corresponding aniline 7-3 using $Fe/NH_4Cl$ in refluxing aqueous EtOH as described in Example 6 (step 4).

Example 8

7-Amino-2H-1-benzopyran-3-carboxylic acid methyl ester

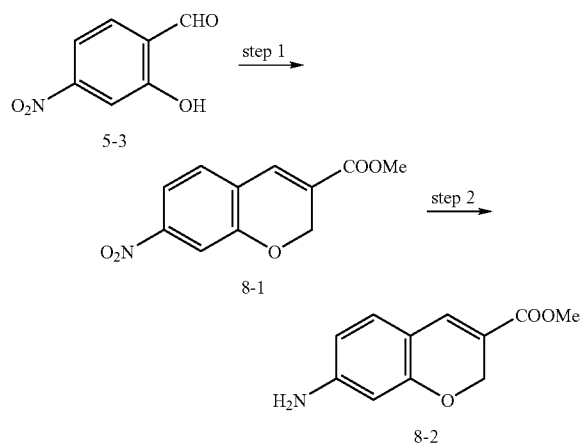

Step 1:

The hydroxynitroaldehyde 5-3 from step 2 of Example 5 (2.50 g, 14.96 mmol) was suspended in methyl acrylate (13.5 mL, 150 mmol, 10 equivalents) and the mixture heated to 50° C. to produce a yellow solution. DABCO (0.42 g, 3.74 mmol, 0.25 equivalent) was added and the mixture heated to 90° C. for 2.5 days. The reaction mixture was cooled to room temperature and diluted with ether (150 mL). The solution was washed with 1N NaOH (2×100 mL), 1N HCl (100 mL) and brine-(100 mL). After drying ($Na_2SO_4$), removal of volatiles gave an orange solid (0.5 g). The combined aqueous phases were re-extracted with EtOAc (2×300 mL) to give 2 g of solid that was purified by flash chromatography on silica gel using 15% EtOAc in hexane as eluent. The desired nitrobenzopyran 8-1 was obtained as an orange solid (0.47 g, 15% yield).

Step 2:

The nitro derivative 8-1 from above (0.41 g) was reduced to the corresponding aniline 8-2 using $Fe/NH_4Cl$ in refluxing aqueous EtOH using the procedure described in Example 6 (step 4).

Example 9

General Procedure for the Alkylation of 2-hydroxy-4-nitrocinnamate esters Using Halides as Electrophiles

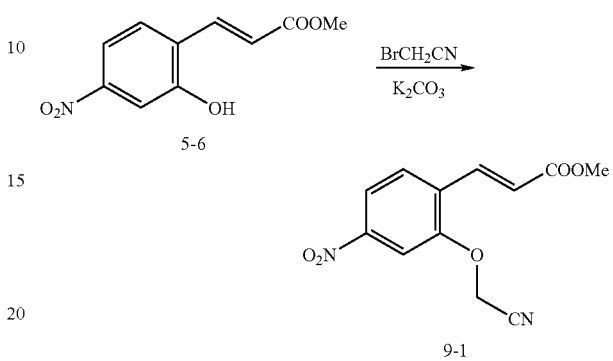

The preparation of (E)-3-(2-Cyanomethoxy-4-nitrophenyl)acrylic acid methyl ester is illustrative: methyl-2-hydroxy-4-nitrocinnamate (compound 5-6; from Example 5, step 6) (2.49 g, 11 mmol) was combined with potassium carbonate (1.70 g, 12 mmol) in anhydrous DMF (20 mL). Bromoacetonitrile (1.17 mL, 17 mmol) was added and the red mixture was stirred at ambient temperature for 3 hours, at which time a yellow/orange heterogeneous mixture was observed. The mixture was diluted in EtOAc and washed with 0.5 N $KHSO_4$, saturated aqueous $NaHCO_3$ and brine. The organic phase was dried with $MgSO_4$, filtered and concentrated under reduced pressure. The crude residue was triturated with ether/DCM and collected by filtration. The desired ether 9-1 was recovered in a 91% yield (2.67 g) as a yellow powder.

It will be apparent to one skilled in the art that the general procedure of Example 9 may be used to prepare intermediates useful in the preparation of compounds of formula (I) by replacing bromoacetonitrile with an appropriate reagent of the formula $R^5$—X, wherein $R^5$ is as defined herein and wherein X is a leaving group such as a halogen, sulfonate ester or the like.

Example 10

General Procedure for the Alkylation of 2-hydroxy-4-nitrocinnamate esters Using a Mitsunobu Etherification Protocol

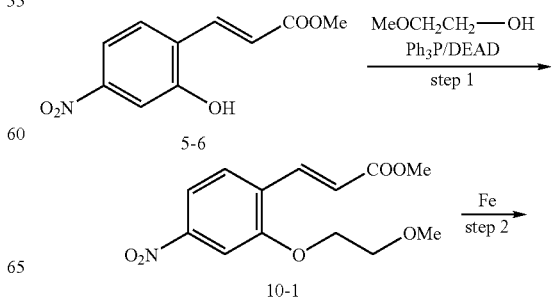

-continued

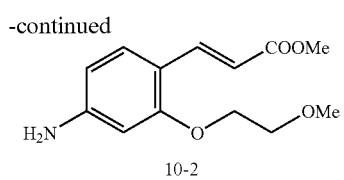

10-2

Step 1:

The preparation of (E)-3-[2-(2-Methoxyethoxy)-4-nitrophenyl]acrylic acid methyl ester 10-1 is illustrative: Methyl-2-hydroxy-4-nitrocinnamate (compound 5-6; from Example 5, step 6) (1.01 g, 4.5 mmol) was combined with 2-methoxyethan-1-ol (0.53 mL, 6.8 mmol) and diethylazodicarboxylate (1.07 mL, 6.8 mmol) in THF (20 mL). Triphenylphosphine (1.78 g, 6.8 mmol) was added and the solution was stirred 15 min at ambient temperature. The reaction mixture was diluted in EtOAc and washed with water and brine. The organic phase was dried with $MgSO_4$, filtered and concentrated under reduced pressure. The crude material was subjected to flash chromatography (1:9 EtOAc/Hex; 1:4; 1:3). The desired product 10-1 was recovered as a light yellow solid in 80% yield (1.01 g).

Step 2:

The nitrocinnamate ester 10-1 (353 mg, 1.3 mmol) was combined with iron powder (209 mg, 3.8 mmol) in absolute ethanol (5 mL). Saturated aqueous ammonium chloride (1 mL) and distilled water (1 mL) were added and the heterogeneous mixture was heated at 80° C. with stirring. After two hours the rust colored mixture was diluted in EtOAc and washed with water and brine. The organic phase was dried with $MgSO_4$, filtered and concentrated under reduced pressure. The residue was subjected to flash chromatography (1:2→1:1 EtOAc/Hex) to afford 223 mg (71%) of desired aniline 10-2 as a yellow solid. FIA-MS m/z=252.1 ($MH^+$).

It will be apparent to one skilled in the art that the general procedure of Example 10 may be used to prepare intermediates useful in the preparation of compounds of formula (I) by replacing 2-methoxyethan-1-ol in Step 1 with an appropriate reagent of the formula $R^5$—OH, wherein $R^5$ is as defined herein.

Example 11

(E)-3-[4-({1-[(3-Cyclopentyl-1-methyl-2-pyridin-2-yl-1H-indole-6-carbonyl)-amino]cyclobutanecarbonyl}amino)-2,6-dimethoxyphenyl]acrylic acid (Compound 2005, Table 2)

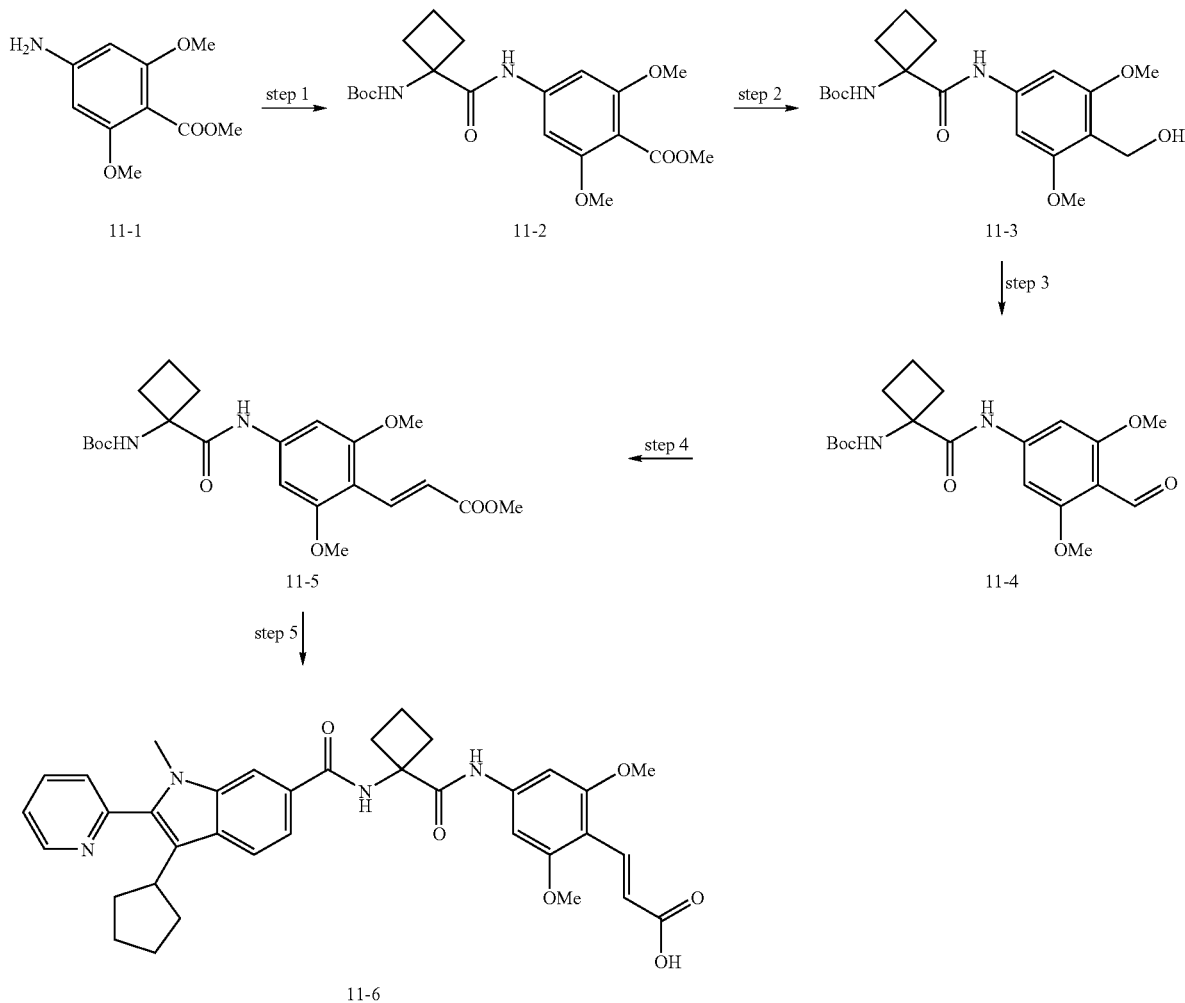

Step 1:

Methyl 4-amino-2,6-dimethoxybenzoate 11-1 (2.00 g, 9.5 mmol), prepared by the method of Broadhurst et al. (J. Chem. Soc. 1977, 2502), was dissolved in DMSO (20 mL). N-Boc-1-aminocyclobutane-1-carboxylic acid (2.07 g, 9.6 mmol) was added followed bytriethylamine (4.18 mL, 30 mmol, 3.2 equivalents) and TBTU (3.69 g, 11.5 mmol, 1.2 equivalent). The mixture was stirred for 24 h at room temperature after which it was added dropwise to a solution of AcOH (15 mL) in water (150 mL). The white precipitate 11-2 was collected by filtration, washed with water and dried in vacuum (3.50 g, 71% yield): MS m/z 409.3 (MH$^+$).

Step 2:

The methyl ester 11-2 from above (1.84 g, 4.5 mmol) was dissolved in THF (20 mL) and the solution cooled in ice under an inert atmosphere. LiAlH$_4$ (1M in ether, 27 mL, 27 mmol) was added dropwise and the reaction mixture allowed to warm up to room temperature. After stirring for 3.5 h, the reaction was judged complete (HPLC analysis). It was quenched by careful addition of AcOH, diluted with DCM (250 mL) and 150 mL of 1M sodium-potassium tartrate solution (Rochelle's salt) was added. After stirring vigorously for 90 min, the mixture was filtered to remove solids, the organic phase was separated, dried (Na$_2$SO$_4$) and concentrated to a white solid. The residue was triturated with TBME (25 mL) and the white solid collected and dried in air to give compound 11-3 (0.65 g, 38% yield): MS m/z 379.2 (M–H).

Step 3:

The benzylic alcohol 11-3 from above (656 mg, 1.72 mmol) was suspended in THF (50 mL) and activated MnO$_2$ (85%, 2.12 g, 20.7 mmol) was added. The mixture was refluxed for 24 h, cooled and diluted with additional THF (50 mL). The mixture was filtered through a small pad of silica gel using THF for washings and the filtrate concentrated to give a brown solid. The solid was suspended in TBME (10 mL), filtered, washed with fresh TBME and dried in air to give compound 11-4 (450 mg, 69% yield): MS m/z 379.2 (MH$^+$).

Step 4:

Triethylphosphonoacetate (0.92 mL, 5.68 mmol) was added dropwise to a suspension of NaH (60% in oil, 0.227 g, 5.68 mmol) in dry THF (25 mL). The resulting thick-white suspension was stirred for 30 min at room temperature and a solution of the aldehyde derivative 11-4 from above (0.43 g, 1.14 mmol) in THF (5 mL+2 mL rinse) was added. The reaction mixture was stirred for an additional 30 min at room temperature and the quenched by addition of AcOH (0.5 mL). THF was removed under reduced pressure and the residue was dissolved in EtOAc (50 mL). The solution was washed with 10% NaHCO$_3$ (20 mL), dried (MgSO$_4$) and concentrated. The residue was purified by flash chromatography on silica gel using 0–20% EtOAc in CHCl$_3$ as eluent. The desired cinnamate derivative 11-5 was obtained as a white solid (452 mg, 91% yield): MS m/z 435.2 (MH$^+$).

Step 5:

The Boc-protected derivative 11-5 from step 4 (120 mg) was suspended in 4M HCl in dioxane (4 mL) and the mixture stirred at room temperature for a few minutes until homogeneous. Reversed-phase HPLC analysis indicated complete conversion to the amine hydrochloride along with some decomposition. Volatiles were removed under reduced pressure and the residue was dissolved in CHCl$_3$ (2 mL). While stirring, TBME (10 mL) was added slowly to produce a white precipitate that was stirred overnight. The solid was then collected, washed with TBME and dried (92 mg of impure material).

The crude amine hydrochloride from above (57 mg, 0.17 mmol) was dissolved in DMSO (1 mL) and the indole derivative (prepared as in WO 03/010141) (50 mg, 0.16 mmol) was added followed by triethylamine (0.1 mL, 0.7 mmol) and TBTU (60 mg, 0.185 mmol). The mixture was stirred overnight at room temperature. NaOH (2.5M, 0.5 mL) was then added followed by additional DMSO (0.75 mL) and the mixture stirred at 50° C. for 2 h, after which saponification of the methyl ester was complete (HPLC). The reaction mixture was cooled to room temperature and acidified by addition of TFA (0.15 mL). The final product 11-6 (Compound 2005, Table 2) was isolated by preparative reversed-phase HPLC (31 mg, 27% yield): MS m/z 623.2 (MH$^+$). $^1$H NMR (DMSO-d$_6$) δ 9.69 (s, 1H), 8.84 (s, 1H), 8.80 (d, J=4.1 Hz, 1H), 8.22 (s, 1H), 8.01 (dt, J=7.6, 1.8 Hz, 1H), 7.85 (d, J=16.2 Hz, 1H), 7.71 (d, J=8.4 Hz, 1H, part of AB), 7.66 (d, J=8.4 Hz, 1H, part of AB), 7.60 (d, J=7.6 Hz, 1H), 7.49 (dd, J=7.4, 5.7 Hz, 1H), 7.16 (s, 2H), 6.57 (d, J=16.2 Hz, 1H), 3.81 (s, 6H), 3.72 (s, 3H), 3.14 (m, 1H), 2.73 (m, 2H), 2.37 (m, 2H), 2.04–1.82 (m, 8H), 1.61 (m, 2H). Note: a similar procedure can be used with other carboxylic acids of general formula II to prepare analogous dimethoxy cinnamate derivatives. In addition, triethylphosphonoacetate can be replaced by other phosphonate derivatives to introduce substitiuents on the double bond α-to the carboxylic acid function (e.g. Me, Et, F).

Example 12

(E)-3-[4-({1-[(3-Cyclopentyl-1-methyl-2-pyridin-2-yl-1H-indole-6-carbonyl)-amino]cyclobutanecarbonyl}amino)-2-ethoxyphenyl]acrylic acid (Compound 1005, Table 1)

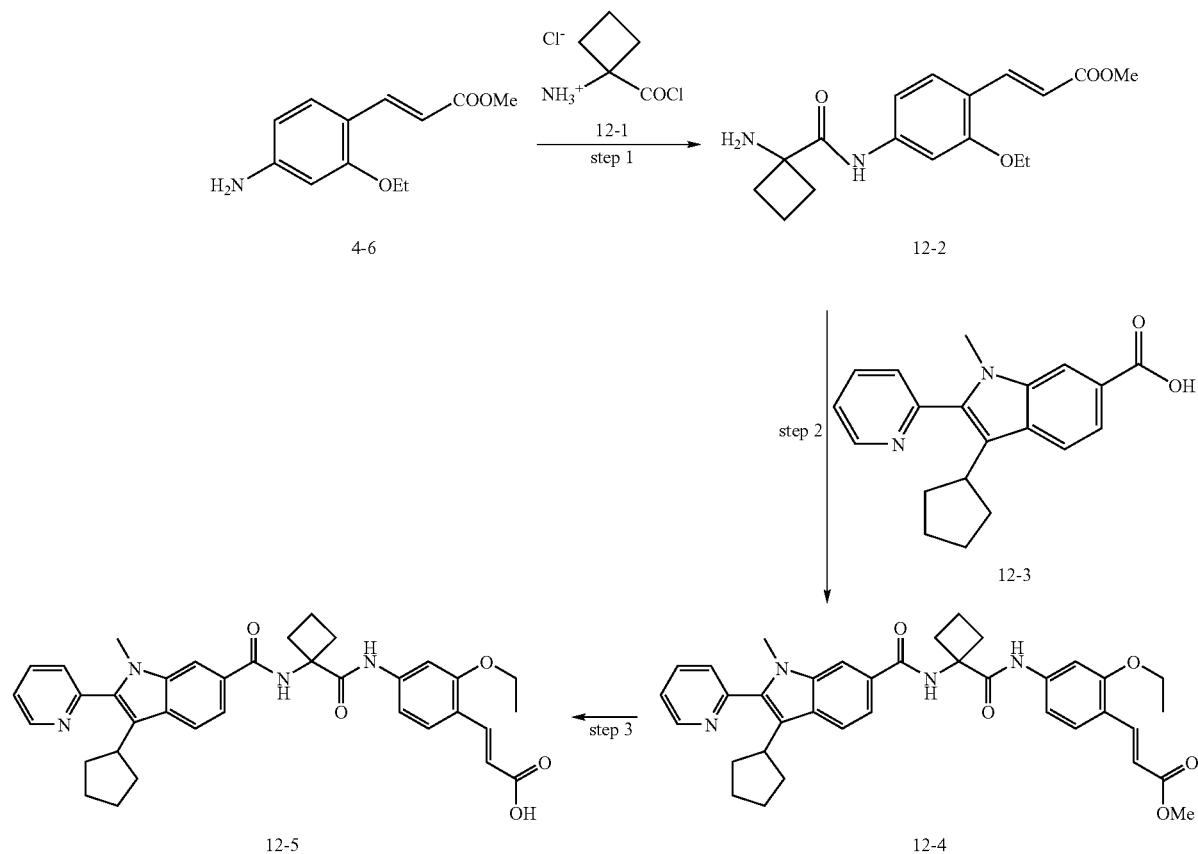

Step 1:

The aniline 4-6 (Example 4) (7.64 g, 34.5 mmol) was added portion wise over 3 min to a suspension of the amino acid chloride hydrochloride 12-1 (prepared as described in WO 03/010141; 6.80 g, 40 mmol) in MeCN (150 mL). The suspension was stirred for 20 h at room temperature. Solid $K_3PO_4$ (18.50 g, 87 mmol) was added and after 15 min, the suspension was poured into water. The oily product was extracted into EtOAc, washed with brine and the solution dried ($Na_2SO_4$). The material was purified by flash chromatography on silica gel using 90% EtOAc in hexane as eluent. The product 12-2 was obtained as a white solid: MS m/z 319.1 ($MH^+$).

Step 2:

The amine 12-2 from step 1 (0.238 g, 0.75 mmol) and indole carboxylic acid 12-3 (prepared as described in WO 03/010141: 0.200 g, 0.62 mmol) were dissolved in DMF (6 mL) and triethylamine (0.265 mL, 1.9 mmol) was added followed by TBTU (0.260 g, 0.81 mmol). The mixture was stirred at room temperature for 15 h. The reaction was then diluted with EtOAc and the solution washed sequentially with aqueous $NaHCO_3$ (2×), water (2×) and brine. After drying ($MgSO_4$), removal of volatiles under reduced pressure gave a solid that was purified by flash chromatography on silica gel using 75% EtOAc in hexane as eluent. The desired product 12-4 was obtained as a white solid (0.345 g, 89% yield).

Step 3:

The ester 12-4 from step 2 (0.200 g, 0.32 mmol) was dissolved in a mixture of THF (3 mL), MeOH (2 mL) and water (1 mL). 10N NaOH (0.20 mL) was added and the mixture stirred 17 h at room temperature and then for 1.5 h at 50° C. to complete the conversion. THF and MeOH were removed under reduced pressure and the remaining solid was suspended in water. The mixture was acidified to pH 3.5 with 1N HCl and the precipitated solid collected by filtration. The white solid was washed with water and dried. The product 12-5 (compound 1005, Table 1) was triturated with EtOAc to remove impurities (46 mg): $^1$H NMR (DMSO-$d_6$) δ 12.12 (broad s, 1H), 9.68 (s, 1H), 8.84 (s, 1H), 8.80 (m, 1H), 8.20 (s, 1H), 7.98 (t, J=7.6 Hz, 1H), 7.75–7.64 (m, 3H), 7.59–7.56 (m, 2H), 7.52 (s, 1H), 7.49–7.46 (m, 1H), 7.21 (d, J=8.2 Hz, 1H), 6.40 (d, J=16.0 Hz, 1H), 4.08–3.99 (m, 2H), 3.72 (s, 3H), 3.15 (m, 1H), 2.77–2.68 (m, 2H), 2.40–2.31 (m, 2H), 2.03–1.80 (m, 8H), 1.65–1.57 (m, 2H), 1.38 (t, J=6.8 Hz, 3H).

Example 13

(E)-3-[4-{2-[(3-Cyclopentyl-1-methyl-2-pyridin-2-yl-1H-indole-6-carbonyl)-amino]-2-methylpropionylamino}-2-(2-methoxyethoxy)phenyl]acrylic acid (Compound 1078, Table 1)

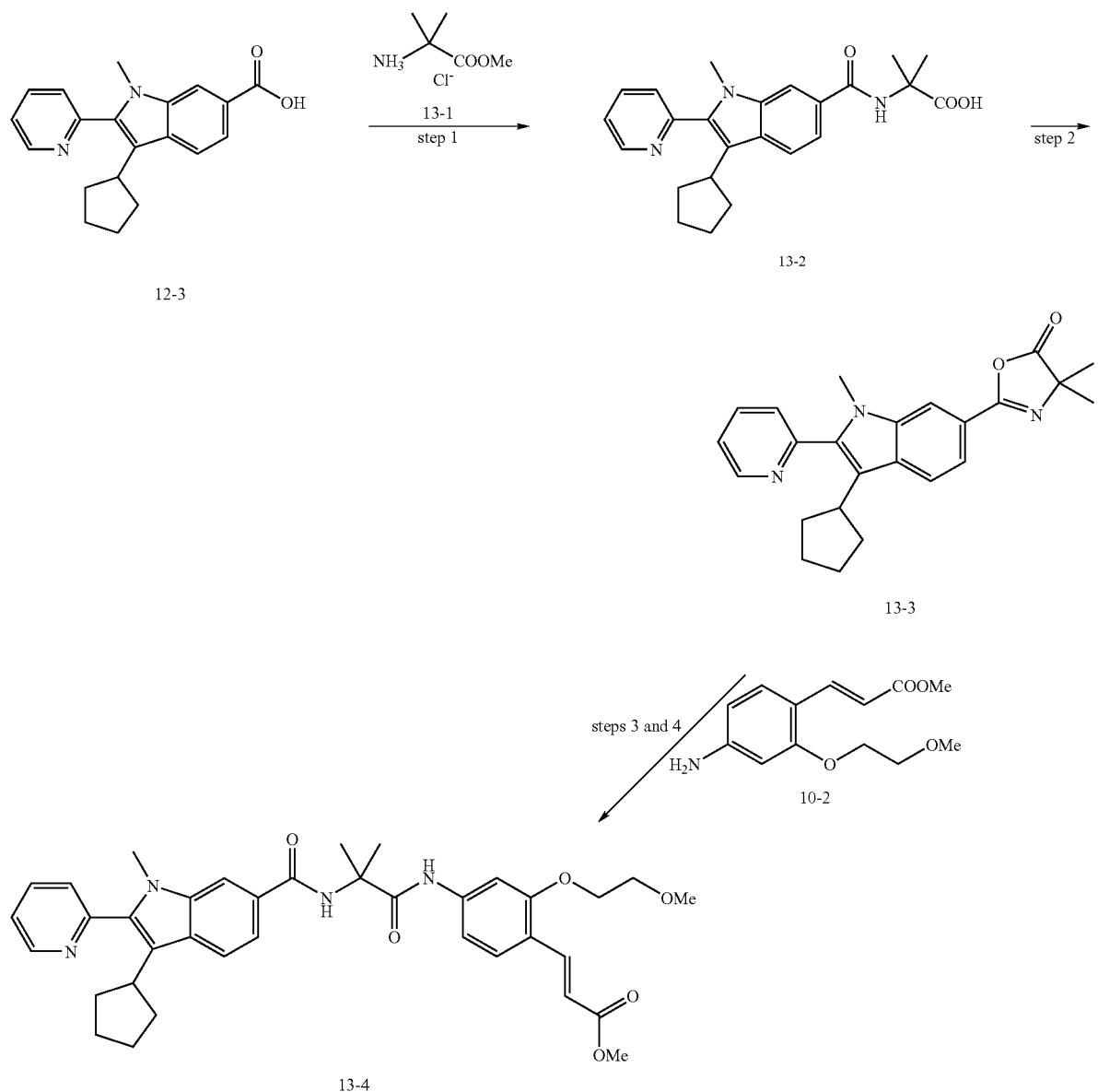

Step 1:

The indole carboxylic acid 12-3 (prepared as described in WO 03/010141: 1.04 g, 3.3 mmol), amino acid ester hydrochloride salt 13-1 (0.45 g, 2.9 mmol) and TBTU (1.12 g, 3.5 mmol) were dissolved in DMF (15 mL). Triethylamine (2.04 mL, 14.7 mmol) was added and the solution was stirred 12 hours. The reaction mixture was diluted in EtOAc and washed with water, 1N NaOH and brine. The organic phase was dried with MgSO$_4$, filtered and concentrated under reduced pressure. The resulting solid was triturated in Et$_2$O/Hex (1:4), filtered and washed with hexanes. The solid was dried in vacuo to afford 1.08 g, of the methyl ester as an off-white powder. MS m/z (MH$^+$) 419.2; RP HPLC: t$_R$=4.96 min., >99% homogeneity at 220 nm. The methyl ester (1.08 g, 2.6 mmol) was dissolved in THF (45 mL), MeOH (10 mL) and water (3 mL). Sodium hydroxide (1N, 12.8 mL) was added and the solution was heated to 60° C. and stirred 1 hour. The organic solvents were then removed under reduced pressure and the pH of the resulting aqueous solution was adjusted to 3 with 1N HCl. The aqueous phase was extracted with EtOAc (×3) and the combined organic extracts were washed with brine then dried with MgSO₄ and filtered. Concentration in vacuo afforded 1.01 g (78%, 2 steps) of the carboxylic acid 13-2 as a yellow solid. MS m/z (MH⁺) 405.2; RP HPLC: $t_R$=4.45 min., >99% homogeneity at 220 nm.

Step 2:

The carboxylic acid 13-2 from step 1 (800 mg, 1.8 mmol) was suspended in acetic anhydride (24 mL). Heating the mixture to 100° C. resulted in the formation of a yellow solution. Analysis by TLC indicated complete conversion to the azalactone. The crude mixture was concentrated under reduced pressure. The yellow residue was dissolved in toluene and concentrated in vacuo (repeated 3 times) to remove residual acetic anhydride. Recovered 745 mg (97%) of the azalactone 13-3 as an amber oil. MS m/z (MH⁺) 388.1.

Step 3:

The azalactone 13-3 from step 2 (39 mg, 0.10 mmol) and aniline 10-2 (Example 10) (23 mg, 0.09 mmol) were suspended in a mixture of toluene (1.5 mL) and acetic acid (0.15 mL). The mixture was heated to 85° C. at which point a yellow solution was observed. After two hours, the solution was diluted in EtOAc and washed with 1 N NaOH (×2), water and brine. The organic phase was dried with MgSO₄, filtered and concentrated under reduced pressure.

Step 4:

The crude residue from step 3 was dissolved in DMSO (2 mL) and sodium hydroxide (1 N, 0.3 mL) was added. The resulting yellow solution was stirred for 12 hours. The reaction was quenched with TFA (0.04 mL, 0.5 mmol) and injected directly onto a preparative reverse phase HPLC for purification. 27 mg (46%) of the desired compound 13-4 (compound 1078, Table 1) was isolated as a yellow lyopholyzed foam. Analytical RP HPLC: $t_R$=5.70 min., >98% @ 220 nm; MS m/z (MH⁺)=625.4; ¹H NMR (400 MHz, DMSO-d₆): 9.62 (s, 1H), 8.80 (d, 1H, J=4.3 Hz), 8.35 (s, 1H), 8.18 (s, 1H), 8.00 (dt, 1H, J=7.6, 1.6 Hz), 7.75–7.45 (m, 7H), 7.28 (dd, 1H, J=8.6, 1.3 Hz), 6.42 (d, 1H, J=16.0 Hz), 4.11–4.07 (m, 2H), 3.72–3.68 (m, 5H), 3.14 (tt, 1H, J=8.9 Hz), 1.94–1.80 (m, 6H), 1.65–1.54 (m, 8H).

Example 14

2-(5-Bromopyrimidin-2-yl)-3-cyclopentyl-1-methyl-1H-indole-6-carboxylic acid

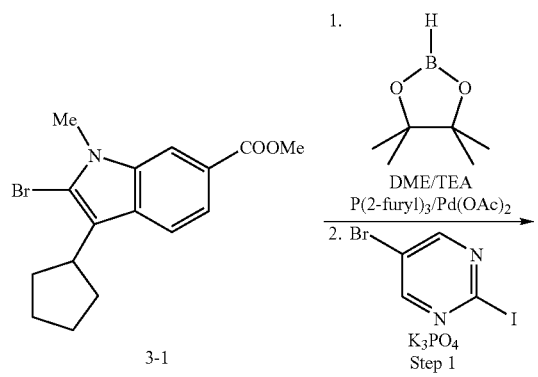

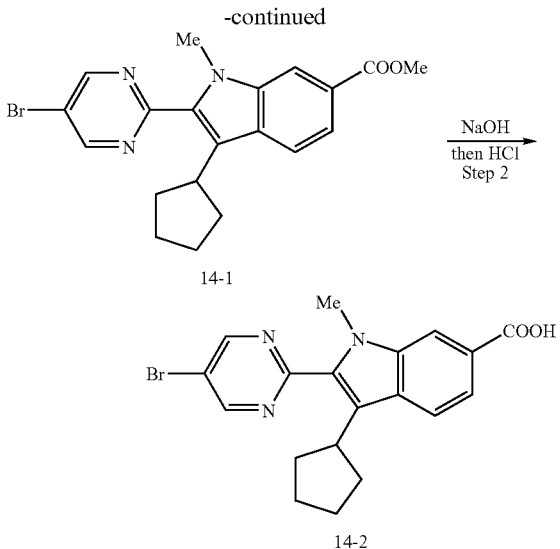

Step 1:

The bromoindole 3-1 (Example 3; prepared as described in Example 12 of WO 03/010141) (3.0 g, 8.9 mmol, 1 equiv.) was dissolved in anhydrous DME (20 mL) and to this solution was added tri-(2-furyl)phosphine (260 mg, 1.1 mmol, 0.12 equiv.), triethylamine (3.0 mL, 21.5 mmol, 2.4 equiv.) and Pd(OAc)₂ (65 mg, 0.28 mmol, 0.03 equiv.). The mixture was purged by bubbling Ar through it for 10 min and pinacolborane (4,4,5,5-tetramethyl-1,3,2-dioxaborolane; 3.0 mL, 20 mmol, 2.2 equiv.) was added by syringe. The resulting dark brown mixture was stirred at 68° C. for 16 h under an argon atmosphere. The reaction mixture was then cooled to RT and the 5-bromo-2-iodopyrimidine (3.0 g, 10.5 mmol, 1.18 equiv.) was added as a solid, followed by careful, slow addition of a cooled suspension of K₃PO₄ (10.5 g, 47.1 mmol, 5.4 equiv.) in water (7 mL). Alternatively, the addition of K₃PO₄ may precede the addition of 5-bromo-2-iodopyrimidine. The dark brown reaction mixture was then heated to 80° C. under argon for 24 h. The reaction mixture was cooled to RT and poured into 10% aqueous NaCl (100 mL). The brown suspension was extracted with EtOAc (150 mL). The extract was washed with water (2×50 mL) and brine (100 mL), dried and concentrated to a volume of 50 mL. Cooling 2 h in the refrigerator gave a beige precipitate that was collected by filtration, washed with a small amount of EtOAc and dried. The filtrate was concentrated under vacuum and the residue was slurried in acetone (20 mL), heated to boiling and cooled in the fridge overnight. The solid was collected by filtration and the combined solids were further purified by chromatography using CHCl₃ as solvent to give the desired indole ester 14-1 as a beige solid in 77% yield.

Step 2:

The ester 14-1 (300 mg, 0.72 mmol) was suspended in DMSO (10 mL) and the suspension warmed gently to dissolve the solid. The slightly cloudy yellow solution was cooled and stirred while 2.5 N NaOH (2.0 mL, 5.0 mmol, 8.6 equiv.) was added and stirring was continued for 4 h at RT. The mixture was slowly poured into 0.5 N HCl (200 mL). The yellow precipitate was collected by filtration, washed with water and dried to give compound 14-2 (273 mg, 94% yield, 100% homogeneity).

Example 15

2-(5-Chloropyrimidin-2-yl)-3-cyclopentyl-1-methyl-1H-indole-6-carboxylic acid

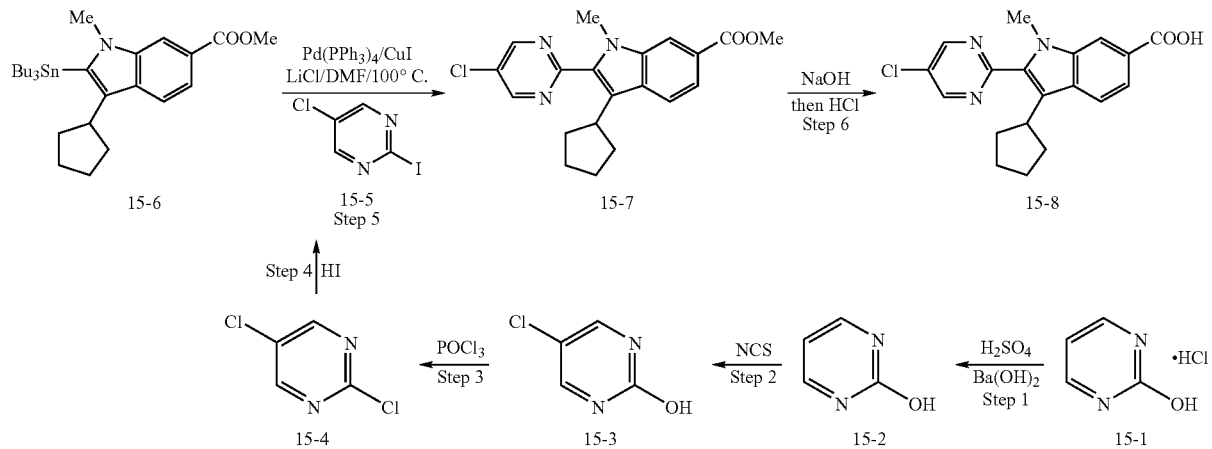

Step 1:

2-Hydroxypyrimidine hydrochloride 15-1 (100 g, 0.754 mole) was dissolved in water (180 mL) and conc. $H_2SO_4$ (42 mL, 0.788 mole) was added dropwise with vigorous stirring. After stirring for an additional 30 min, water was removed under reduced pressure at 70° C. and the orange residue dried under high vacuum to leave a residue (146 g). The residue was transferred into a 4 L flask and water (500 mL) was added. A suspension of $Ba(OH)_2$ (129 g, 0.752 mole) in water (1200 mL) was added and the cloudy suspension stirred for 30 min. The mixture was filtered through Celite™ and the water removed under reduced pressure to provide 15-2 as a bright yellow solid (66.4 g)

Step 2:

2-Hydroxypyrimidine 15-2 from step 1 (42 g, 0.44 mole) was added to AcOH (500 mL) and the mixture heated to 120° C. N-Chlorosuccinimide (67 g, 0.5 mole, 1.15 equivalent) was added cautiously (15 min) in small amounts to the hot solution. Stirring was continued for an additional 5 min and the reaction mixture cooled to RT. The material was concentrated under reduced pressure and the residue was stirred overnight with $CH_2Cl_2$ (200 mL). The suspended solid was removed by filtration and the filtrate evaporated under reduced pressure to give 15-3 as a beige solid (17.3 g)

Step 3:

The 5-chloro-2-hydroxypyrimidine 15-3 from step 2 (8.0 g, 0.06 mole) was placed in a dry 500 mL flask under an Ar atmosphere, and $POCl_3$ (79.4 mL) was added followed by N,N-dimethylaniline (2.6 g). The mixture was heated to 120° C. and stirred for 1 h. The dark brown mixture was concentrated under reduced pressure at 50° C. The residue was quenched carefully with ice water and the precipitated material was extracted with pentane (3×200 mL). The extract was washed with water and aqueous $NaHCO_3$ solution, and dried ($Na_2SO_4$). Volatiles were removed under reduced pressure with no external heating to prevent sublimation of the volatile dichloropyrimidine, to provide the desired product 15-4 as a white solid (6 g).

Step 4:

A flask was charged with 57% HI (48 mL) and cooled to 0° C. in an ice-salt mixture. The dichloropyrimidine 15-4 from step 3 (6 g) was added and the mixture stirred for 4 h. The yellow suspension was treated carefully with $K_2CO_3$ (32 g) in water (60 mL) and the pale yellow solid was collected by filtration. The solid was washed with water and dried to give compound 15-5 (8 g); $^1$H NMR (CDCl$_3$) δ 8.47 (s, 2H).

Step 5:

The 2-iodo-5-chloropyrimidine 15-5 from step 4 was cross-coupled to the stannylindole derivative 15-6 (prepared using a procedure similar to that described in example 5 of WO 03/010140 starting from the 2-bromoindole analog of example 12 of WO 03/010140) using the conditions of the Stille reaction as described in example 6 of WO 03/010140, to give compound 15-7.

Step 6:

The intermediate indole ester 15-7 from step 5 was saponified with NaOH using a similar procedure to that described in step 2 in example 14.

Example 16

(E)-3-{4-[(1-{[2-(5-Chloro-pyrimidin-2-yl)-3-cyclopentyl-1-methyl-1H-indole-6-carbonyl]-amino}-cyclobutanecarbonyl)-amino]-2-ethoxy-phenyl}-acrylic acid (Compound 1070, Table 1)

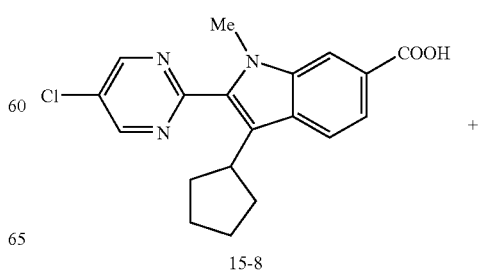

+

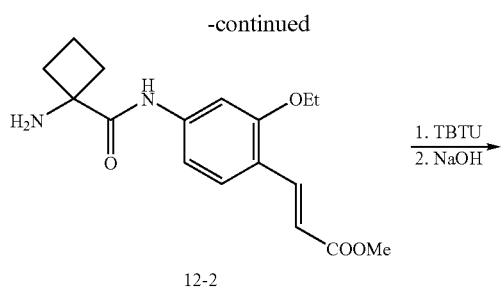

12-2

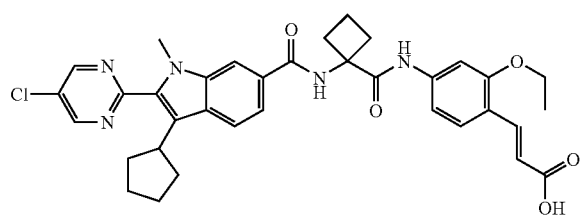

16-1

The 5-chloro-2-pyrimidylindole 15-8 (Example 15) (337 mg, 0.95 mmol), the cyclobutylamine derivative 12-2 (Example 12) (370 mg, 1.04 mmol) and TBTU (334 mg, 1.04 mmol) were combined and dissolved in DMSO (10 mL). Triethylamine (0.4 mL, 2.84 mmol) was added and the mixture stirred for 30 min at RT. The reaction mixture was then diluted with EtOAc and washed with saturated aqueous KHSO$_4$, NaHCO$_3$ and brine. After drying (MgSO$_4$), volatiles were removed under reduced pressure and the residue was triturated with ether to provide the coupled product as the methyl ester (507 mg).

The ester (319 mg) was dissolved in DMSO (10 mL) and 10 N NaOH (0.49 mL) was added. The mixture was stirred at RT for 4.5 h, then was diluted with EtOAc and washed with saturated aqueous KHSO$_4$, NaHCO$_3$ and brine. The extract was dried (MgSO$_4$) and concentrated to a residue that was purified by preparative RP-HPLC to give the title compound 16-1 (Compound 1070, Table 1) (247 mg): $^1$H NMR (400 MHz, DMSO-d$_6$) δ 12.11 (s, 1H), 9.68 (s, 1H), 9.14 (s, 2H), 8.87 (s, 1H), 8.25 (s, 1H), 7.77 (d, J=8.2 Hz, 1H), 7.75 (d, J=16.0 Hz, 1H), 7.67 (d, J=8.4 Hz, 1H), 7.58 (d, J=8.6 Hz, 1H), 7.54 (s, 1H), 7.22 (d, J=8.6 Hz, 1H), 6.41 (d, J=16.1 Hz, 1H), 4.07 (q, J=7.0 Hz, 2H), 3.90 (s, 3H), 3.72 (quintet, J=8.4 Hz, 1H), 2.74 (m, 2H), 2.37 (broad q, J=9.8 Hz, 2H), 2.05–1.82 (m, 8H), 1.65 (m, 2H), 1.39 (t, J=6.9 Hz, 3H).

Example 17

(E)-3-{4-[(1-{[2-(5-Chloro-pyrimidin-2-yl)-3-cyclopentyl-1-methyl-1H-indole-6-carbonyl] amino}cyclobutanecarbonyl)amino]-2-(2-methoxyethoxy)-phenyl}acrylic acid (Compound 1077, Table 1) and (E)-3-{4-[(1-{[3-Cyclopentyl-2-(5-methoxy-pyrimidin-2-yl)-1-methyl-1H-indole-6-carbonyl]amino}cyclobutanecarbonyl)amino]-2-(2-methoxyethoxy)-phenyl}acrylic acid (Compound 1083, Table 1)

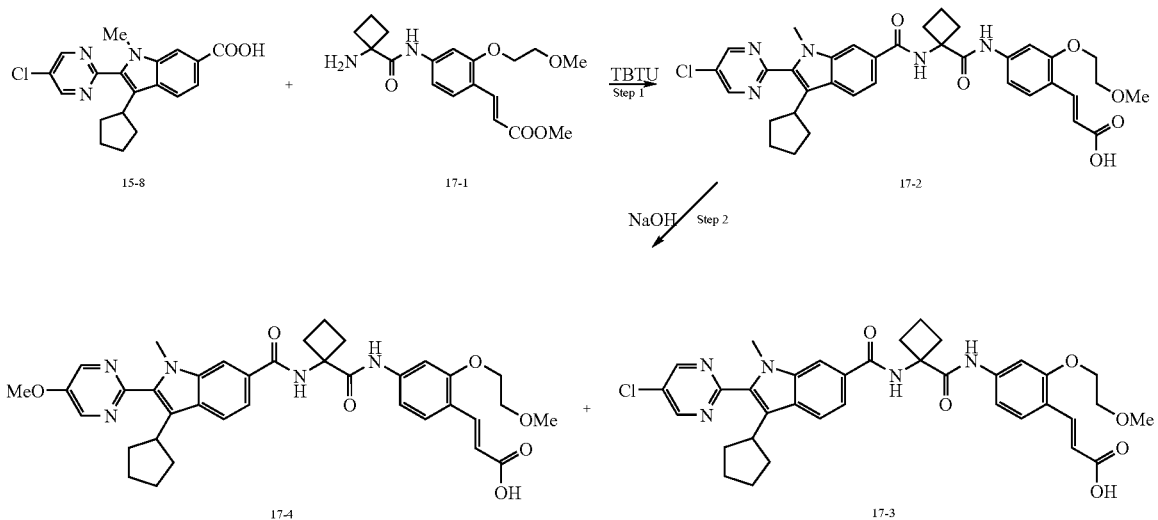

Step 1:

Using the procedure of example 16, indole carboxylic acid 15-8 was coupled to amine derivative 17-1 (prepared using a procedure similar to that described in step 1 of Example 12, but using aniline 10-2 (Example 10) instead of aniline 4-6) to give ester 17-2.

Step 2:

The intermediate ester 17-2 was saponified using the procedure described in Example 16. Purification by RP-HPLC provided 5-chloropyrimidine indole 17-3 (compound 1077, Table 1) as the major product. 5-methoxypyrimidine indole 17-4 (compound 1083, Table 1) was also isolated as side product.

Example 18

3-Cyclopentyl-1,2-dimethyl-6-indolecarboxylic acid

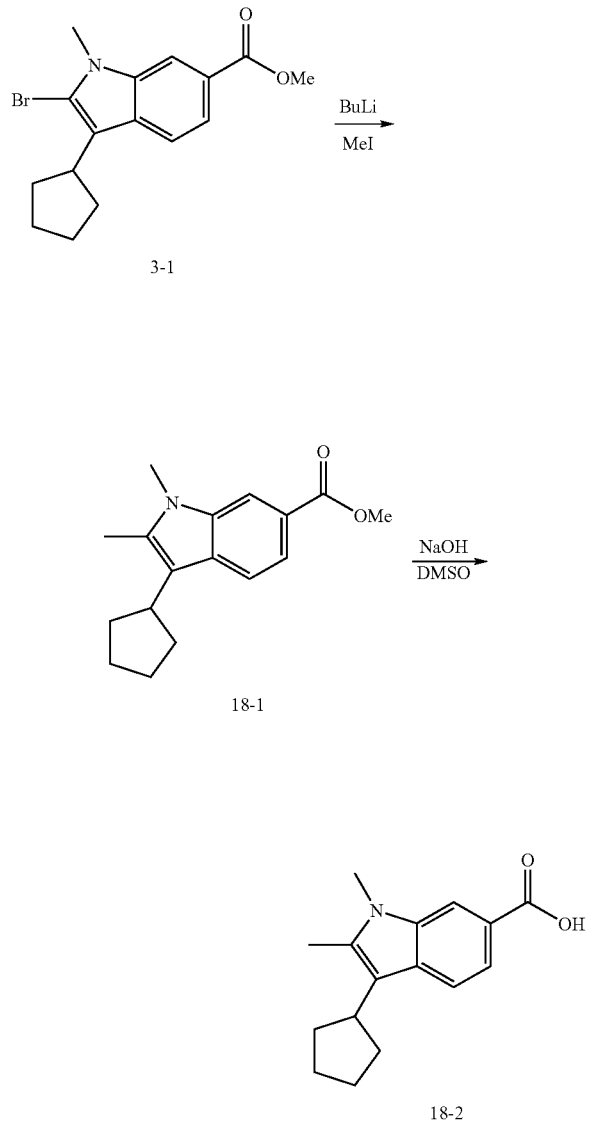

The 2-bromoindole derivative 3-1 (1.009 g, 3.00 mmol, prepared as described in Example 12 of WO 03/010141) was dissolved in anhydrous THF (25 mL) under an argon atmosphere and the solution cooled to −78° C. n-BuLi (2.0 M in hexane, 1.60 mL, 3.20 mmol) was added dropwise and the mixture stirred for 15 min. MeI (0.37 mL, 2.00 mmol) was added and stirring was continued for an additional 30 min. The reaction mixture was then warmed up to RT and volatiles removed under reduced pressure. The residue was dissolved in TBME (100 mL) and the solution washed with brine (2×25 mL). The extract was dried (MgSO$_4$), concentrated under reduced pressure and the residue purified by flash chromatography using 0–15% EtOAc in hexane as eluent. The desired 2-methylindole derivative 18-1 was obtained as a waxy solid (0.658 g, 80% yield): MS-ES m/z 272.1 (MH$^+$). The methyl ester 18-1 was saponified in the usual way (NaOH/DMSO) to give the corresponding carboxylic acid 18-2 in 96% yield: MS-ES m/z258.1 (MH$^+$).

Example 19

2-Acetyl-3-cyclopentyl-1-methyl-1H-indole-6-carboxylic acid

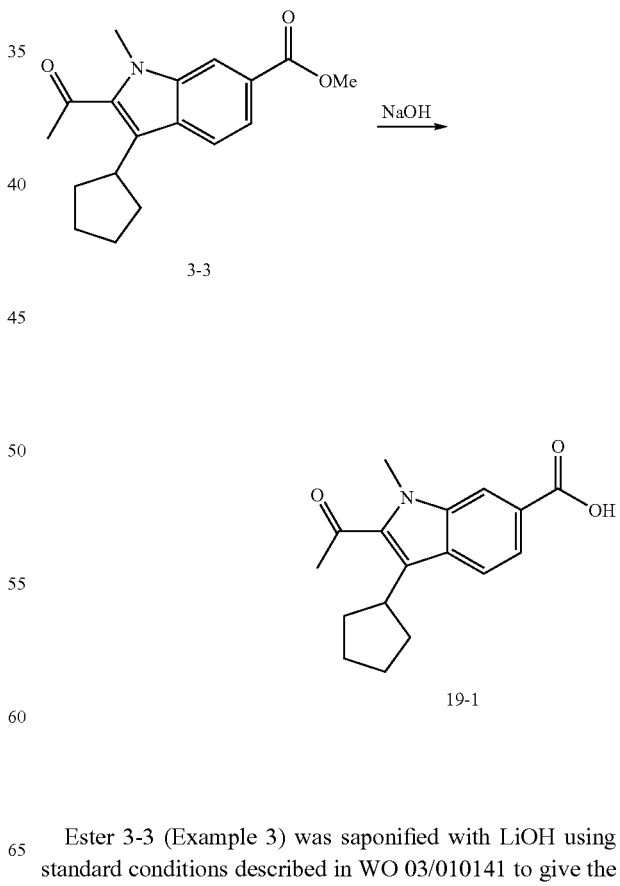

Ester 3-3 (Example 3) was saponified with LiOH using standard conditions described in WO 03/010141 to give the desired indole carboxylic acid 19-1.

Example 20

3-Cyclopentyl-2-ethynyl-1-methyl-1H-indole-6-carboxylic acid

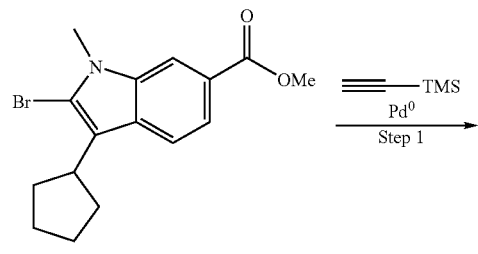

3-1

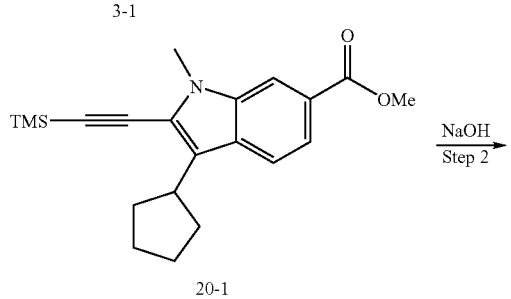

20-1

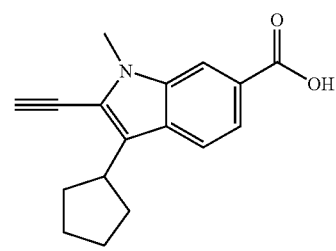

20-2

Step 1:

The 2-bromoindole 3-1 (Example 3; prepared as described in Example 12 of WO 03/010141), Pd(Ph₃P)₄ (10 mole %) and CuI (10 mole %) were combined in degassed toluene under a nitrogen atmosphere. TMS-acetylene (10 equivalents) and triethylamine (5 equivalents) were added and the reaction heated to 100° C. under sealed conditions. After 2 h, the reaction mixture was diluted with EtOAc and the extract washed with saturated aqueous NH₄Cl, bicarbonate and brine. The extract was dried (MgSO₄), volatiles were removed under reduced pressure and the residue was purified by flash chromatography to give compound 20-1.

Step 2:

The partially purified material 20-1 was dissolved in THF/MeOH and 10 N NaOH (10 equivalents) was added. The solution was warmed to 50° C. and stirred overnight. After cooling to RT, the reaction mixture was diluted with EtOAc and washed with KHSO₄ and brine. Drying of the extract (MgSO₄), removal of volatiles under reduced pressure and purification of the residue by flash chromatography gave the desired 2-ethynylindole carboxylic acid 20-2 in ~50% overall yield.

Example 21

1-Cyclohexyl-2-(5-fluoropyridin-2-yl)-3-methyl-1H-indole-5-carboxylic acid

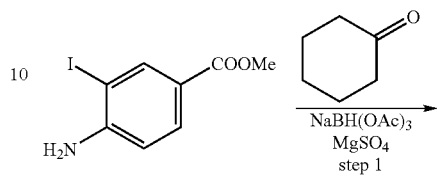

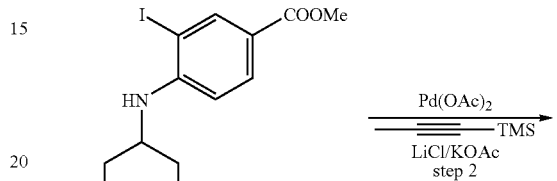

21-1

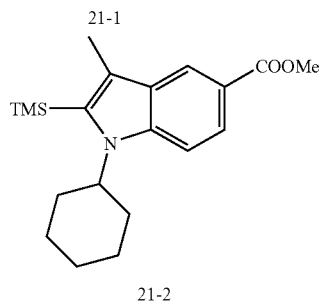

21-2

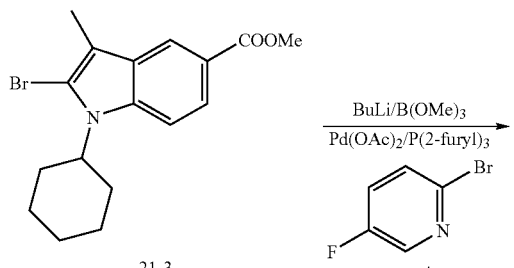

21-3

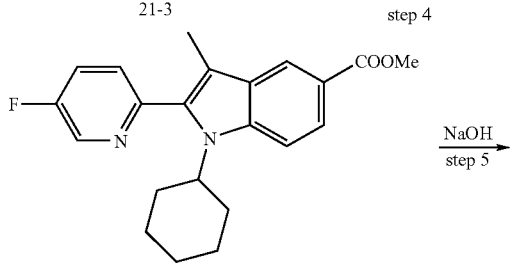

21-4

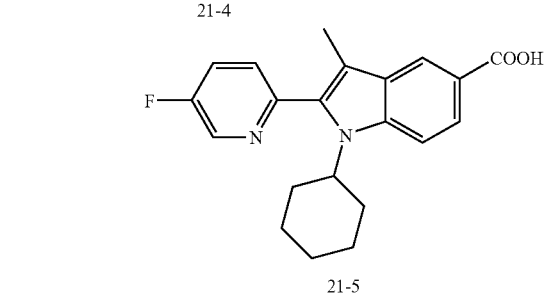

21-5

Step 1:

Methyl 4-amino-3-iodobenzoate (43.75 g, 157.9 mmol) was dissolved in AcOH (900 mL) and anhydrous MgSO$_4$ (190 g) was added. Cyclohexanone (93 g, 0.95 mol, 6 equivalents) was added dropwise over 45 min to the stirred suspension. The resulting mixture was then stirred for an additional 2.5 h at RT. Sodium triacetoxyborohydride (117 g, 0.55 mol, 3.5 equivalents) was added in 8 portions over 20 min and the reaction mixture was stirred overnight at RT. Solids were then removed by filtration using EtOAc for washings and saturated aqueous NaHCO$_3$ (1.1 L) was added dropwise to the filtrate, until the pH of the aqueous phase was 5. EtOAc (800 mL) was added and the product extracted. The aqueous phase was extracted again with EtOAc (2×300 mL) and the combined extracts washed with saturated NaHCO$_3$ and brine, and dried (Na$_2$SO$_4$). The solvent was removed under reduced pressure and the residue purified by flash chromatography using 3% EtOAc in hexane as eluent. The desired product 21-1 was obtained as a yellow oil (60.95 g).

Step 2:

A dry 3-neck flask was equipped with a reflux condenser and purged with Ar. The iodoarene 21-1 from step 1 (51.8 g, 0.144 mole) was added to the flask followed by anhydrous DMF (1 L), LiCl (7.19 g, 0.17 mole), KOAc (33.31 g, 0.34 mole) and 1-trimethylsilyl-1-propyne (57.15 g, 0.51 mole). The red suspension was degassed by passing Ar gas through the mixture for 30 min and Pd(OAc)$_2$ (1.91 g, 8.5 mmol) was added. The mixture was heated to 100° C. and stirred at that temperature overnight, at which point a clear dark red solution was obtained. The reaction mixture was cooled to RT and saturated NH$_4$Cl (1 L) was added. The mixture was then extracted with EtOAc (1 L+2×500 mL) and the combined organic extracts washed with brine (4×600 mL). After drying (Na$_2$SO$_4$), volatiles were removed under reduced pressure and the residue was purified by flash chromatography using hexane and then 9:1 to 9:3 hexane—EtOAc as eluents. The fractions containing the product (40 g) were crystallized from hot hexane (10+3 mL) to give the desired 2-(trimethylsilyl)indole 21-2 as a white solid (37.6 g, 69% yield).

Step 3:

The 2-silylindole 21-2 from step 2 (26.50 g, 77 mmol) was dissolved in CH$_2$Cl$_2$ (600 mL) and the solution cooled in an ice-water bath. A solution of bromine (11.10 g, 69 mmol, 0.9 equivalent) in CH$_2$Cl$_2$ (70 mL) was added dropwise over 1.5 h, keeping the internal temperature close to 0° C. After completion, the light amber solution was stirred for an additional 30 min in the cold. Volatiles were then removed under reduced pressure and the solid purple residue was triturated with CH$_2$Cl$_2$ (5 mL) and hexane (20 mL). The light pink solid was collected by filtration and dried to give compound 21-3 (23.22 g, 86% yield).

Step 4:

The 2-bromoindole 21-3 from step 3 (4.99 g, 14.23 mmol) was placed in a dry 250 mL flask equipped with a reflux condenser and the system was purged with argon gas. Anhydrous THF (25 mL) was added and the yellow solution cooled to −78° C. in a dry-ice acetone bath. n-BuLi (2.5 M in hexane, 6.0 mL, 14.94 mmol, 1.05 equivalent) was added dropwise over 30 min and the dark yellow solution was stirred at −78° C. for an additional 1 h. Trimethylborate (1.77 g, 17.1 mmol, 1.2 equivalent) was added dropwise over 10 min and the mixture stirred for 1 h at −78° C. The dry ice bath was then replaced with an ice-water bath and stirring continued at 0° C. for 1 h and then at RT for 45 min. Additional anhydrous THF (25 mL) was added followed by P(para-tolyl)$_3$ (0.26 g, 0.85 mmol, 0.06 equivalent) and 2-bromo-5-fluoropyridine (2.52 g, 14.3 mmol, 1.0 equivalent). The red solution was degassed by bubbling argon gas through the mixture for 45 min. Anhydrous K$_2$CO$_3$ (3.93 g, 28.5 mmol, 2.0 equivalents), Pd(OAc)$_2$ (32 mg, 0.14 mmol, 0.01 equivalent) and MeOH (16.5 mL) were added and the mixture was refluxed overnight under Ar. The reaction mixture was then cooled to RT and quenched by addition of ether (80 mL) and water (20 mL). The aqueous phase was separated and extracted a second time with ether (80 mL). The combined extracts were washed with water and brine and dried (Na$_2$SO$_4$). Solvents were removed under reduced pressure and the residue was purified by flash chromatography using 5% EtOAc in hexane as eluent. The desired indole derivative 21-4 was obtained as a white solid (3.84 g, 73% yield).

Step 5:

The methyl ester 21-4 from step 4 (3.84 g, 10.5 mmol) was dissolved in DMSO (30 mL) and 1 N NaOH (12.6 mL, 1.2 equivalent) was added dropwise over 15 min. The mixture was stirred for 1 h at which point additional DMSO (20 mL) was added to the thick suspension. After stirring for 5 h, the reaction was judged complete by TLC. Water (30 mL) was added and the resulting clear solution was washed with ether (30 mL) and hexane (2×30 mL). The aqueous phase was then acidified with AcOH to pH=4 and the precipitated solid collected by filtration. The material was washed with water and dried to constant weight under vacuum to give compound 21-5 (3.51 g, 95% yield). MS (ES+) m/z 353.1 (MH$^+$).

Example 22

(E)-3-{4-[(1-{[1-Cyclohexyl-2-(5-fluoropyridin-2-yl)-3-methyl-1H-indole-5-carbonyl]amino}cyclobutanecarbonyl)amino]-2-ethoxyphenyl}acrylic acid (Compound 4001, Table 4)

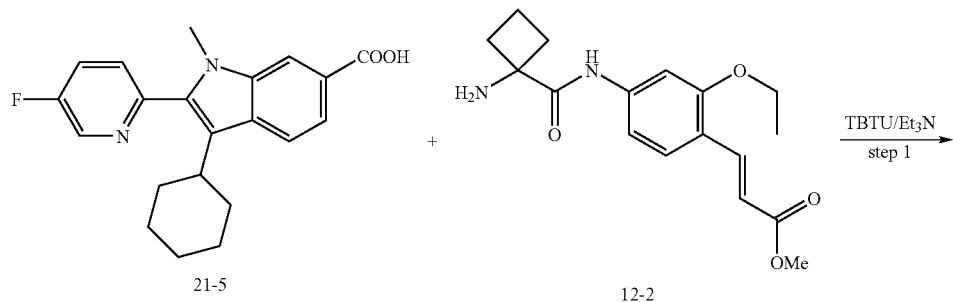

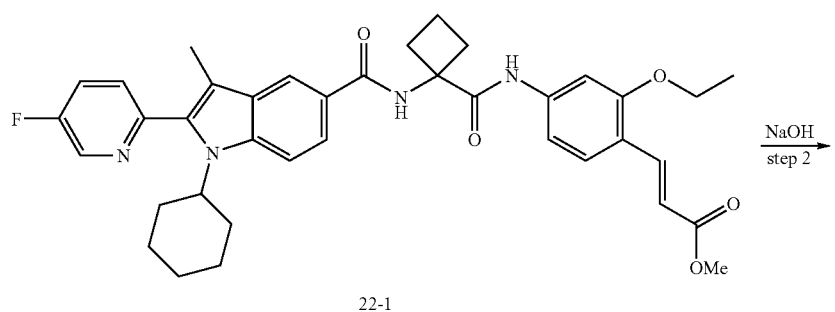

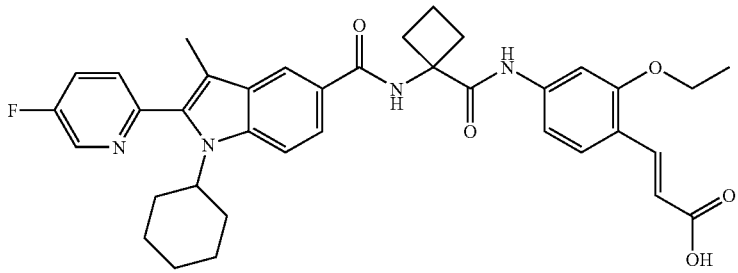

Following the procedure of step 2 of Example 12, the indole derivative 21-5 (Example 21) was coupled to amine 12-2 (Example 12). The ester was saponified using the procedure of step 3 of example 12 and the title compound (compound 4001 of Table 4) was obtained and purified by preparative RP-HPLC: $^1$H NMR (400 MHz, DMSO-$d_6$) δ 12.10 (broad s, 1H), 9.68 (s, 1H), 8.80 (s, 1H), 8.79 (s, 1H), 8.33 (s, 1H), 7.93 (dt, J=8.6, 2.9, 1H), 7.76 (m, 2H), 7.73 (d, J=15.5 Hz, 1H), 7.70 (dd, J=8.6, 4.5 Hz, 1H), 7.57 (d, J=8.6 Hz, 1H), 7.53 (d, J=1.6 Hz, 1H), 7.22 (dd, J=8.4, 1.4 Hz, 1H), 6.40 (d, J=16.0 Hz, 1H), 4.20 (ft, J=12.1, 2.0 Hz, 1H), 4.05 (q, J=6.9 Hz, 2H), 2.72 (m, 2H), 2.37 (m, 2H), 2.27 (s, 3H), 2.19 (m, 2H), 1.98 (m, 1H), 1.94–1.75 (m, 5H), 1.60 (m, 1H), 1.39 (t, J=6.9 Hz, 3H), 1.35–1.15 (m, 3H).

Example 23

Inhibition of NS5B RNA Dependent RNA Polymerase Activity

The compounds of the invention were tested for inhibitory activity against the hepatitis C virus RNA dependent polymerase (NS5B), according to protocol described in WO 03/010141.

Example 24

Specificity of NS5B RNA Dependent RNA Polymerase Inhibition

The compounds of the invention were tested for inhibitory activity against polio virus RNA dependent RNA polymerase in the format that is described for the HCV polymerase, with the exception that poliovirus polymerase was used in place of the HCV NS5B polymerase, as is described in WO 03/010141. The compounds were also profiled for inhibition of the calf thymus DNA dependent RNA polymerase 11 in a previously described assay format (McKercher et al., 2004 Nucleic Acids Res. 32: 422–431).

Example 25

Cell-Based Luciferase Reporter HCV RNA Replication Assay Cell Culture

Huh-7 cells with a stable subgenomic HCV replicon that encodes a modified luciferase reporter gene (expressed as a luciferase-FMDV2A-neomycin phosphotransferase fusion gene) were established as previously described (Lohman et al., 1999. Science 285: 110–113; Vroljik et al., 2003 J. Virol Methods 110:201–209.), with the exception that replicon cells were selected with 0.25 mg/mL G418. The amount of luciferase expressed by selected cells directly correlates with the level of HCV replication. These cells, designated as MP-1 cells, are maintained in Dulbecco's Modified Earle Medium (DMEM) supplemented with 10% FBS and 0.25 mg/mL neomycin (standard medium). The cells are passaged by trypsinization and frozen in 90% FBS/10% DMSO. During the assay, DMEM medium supplemented with 10% FBS, containing 0.5% DMSO and lacking neomycin, was used (Assay medium). The day of the assay, MP-1 cells are trypsinized and diluted to 100 000 cells/mL in assay medium. 100 μL is distributed into each well of a black 96-well ViewPlate™ (Packard). The plate is then incubated at 37° C. with 5% $CO_2$ for two hours.

Reagents and Materials:

| Product | Company | Catalog # | Storage |
|---|---|---|---|
| DMEM | Wisent Inc. | 10013CV | 4° C. |
| DMSO | Sigma | D-2650 | RT |
| Dulbecco's PBS | Gibco-BRL | 14190-136 | RT |
| Fetal Bovine Serum | Bio-Whittaker | 14-901F | −20° C./4° C. |
| Geneticin (G418) | Gibco-BRL | 10131-027 | −20° C./4° C. |
| Trypsin-EDTA | Gibco-BRL | 25300-054 | −20° C./4° C. |
| ViewPlate ™-96, Black | Packard | 6005182 | RT |
| Backing tape, Black | Packard | 6005189 | RT |
| PVDF 0.22μ m Filter Unit | Millipore | SLGV025LS | RT |
| Deep-Well Titer Plate Polypropylene | Beckman | 267007 | RT |

Preparation of Test Compound:

The test compound in 100% DMSO was first diluted in assay medium to a final DMSO concentration of 0.5%. The solution was sonicated for 15 min and filtered through a 0.22 μM Millipore Filter unit. Into column 3 of a Polypropylene Deep-Well Titer Plate, the appropriate volume is transferred into assay medium to obtain the starting concentration (2×) to be tested. In columns 2 and 4 to 12, add 200 μL of assay medium (containing 0.5% DMSO). Serial dilutions (½) are prepared by transferring 200 μL from column 3 to column 4, then from column 4 to column 5, serially through to column 11. Columns 2 and 12 are the no inhibition controls.

Addition of Test Compound to Cells:

A volume of 100 μL from each well of the compound dilution plate is transferred to a corresponding well of the Cell Plate (Two columns will be used as the "No inhibition control"; ten [10] columns are used for the dose response). The cell culture plate 20 was incubated at 37° C. with 5% $CO_2$ for 72 hours.

Luciferase Assay:

Following the 72h incubation period, the medium is aspirated from the 96-well assay plate and a volume of 100 μL of 1× Glo Lysis Buffer (Promega) previously warmed to room temperature was added to each well. The plate was incubated at room temperature for 10 min with occasional shaking. A black tape was put at the bottom of the plate. 100 μL of Bright-Glo luciferase substrate (Promega) previously warmed to room temperature was added to each well followed by gentle mixing. The luminescence was determined on a Packard Topcount instrument using the Data Mode Luminescence (CPS) with a count delay of 1 min and a count time of 2 sec.

| Product | Company | Catalog # | Storage |
|---|---|---|---|
| Glo Lysis Buffer | Promega | E266A | 4° C. |
| Bright-Glo Luciferase Assay System | Promega | E2620 | −20° C. |

The luminescence determination (CPS) in each well of the culture plate was a measure of the amount of HCV RNA replication in the presence of various concentrations of inhibitor. The % inhibition was calculated with the following equation:

% inhibition=100−[CPS(inhibitor)/CPS (control)× 100]

A non-linear curve fit with the Hill model was applied to the inhibition-concentration data, and the 50% effective concentration ($EC_{50}$) was calculated by the use of SAS software (Statistical Software; SAS Institute, Inc. Cary, N.C.).

Tables of Compounds

The following tables lists compounds representative of the invention. All compounds listed in Tables 1 to 5 below were found to have unexpectedly good activity in the cell-based HCV RNA replication assay described in Example 25. Retention times ($t_R$) for each compound were measured using the standard analytical HPLC conditions described in the Examples. As is well known to one skilled in the art, retention time values are sensitive to the specific measurement conditions. Therefore, even if identical conditions of solvent, flow rate, linear gradient, and the like are used, the retention time values may vary when measured, for example, on different HPLC instruments. Even when measured on the same instrument, the values may vary when measured, for example, using different individual HPLC columns, or, when measured on the same instrument and the same individual column, the values may vary, for example, between individual measurements taken on different occasions.

TABLE I
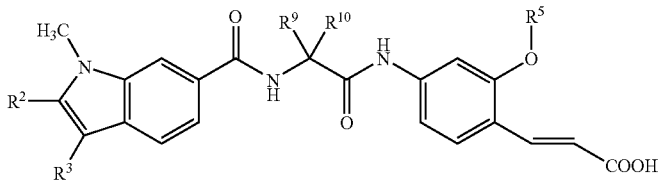
wherein R², R³, R⁵, R⁹ and R¹⁰ are given in the table.
| Cpd. # | R² | R³ | R⁵ | R⁹ R¹⁰ | m/z (M + H)⁺ | $t_R$ (min) |
|---|---|---|---|---|---|---|
| 1001 | 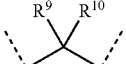 | 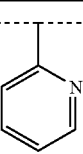 | CH₃ | 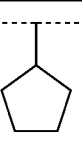 | 593.3 | 5.7 |
| 1002 | 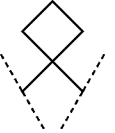 |  | CH₃ |  | 594.3 | 5.5 |
| 1003 | 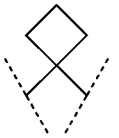 | 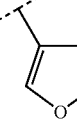 | CH₃ | 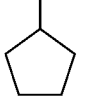 | 582.3 | 7.2 |
| 1004 | 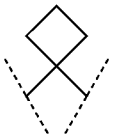 | 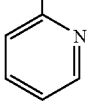 | CH₃ | 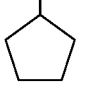 | 622.4 | 4.7 |
| 1005 | 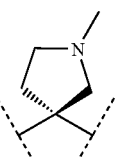 | 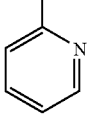 | 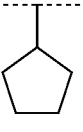 |  | 607.3 | 6.2 |
| 1006 | 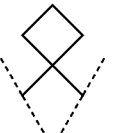 | 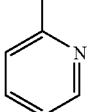 | 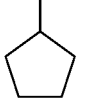 |  | 625.4 | 7.1 |
| 1007 | 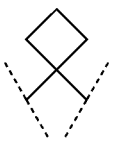 | 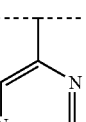 | 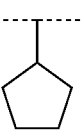 |  | 608.4 | 5.7 |

TABLE I-continued
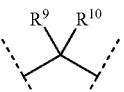
wherein R², R³, R⁵, R⁹ and R¹⁰ are given in the table.
| Cpd. # | R² | R³ | R⁵ | R⁹ R¹⁰ | m/z (M + H)⁺ | t_R (min) |
|---|---|---|---|---|---|---|
| 1008 | 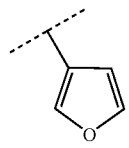 | 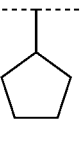 |  | 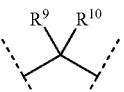 | 596.4 | 6.3 |
| 1009 | 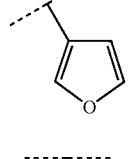 |  | H | 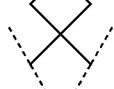 | 568.3 | 7.8 |
| 1010 | 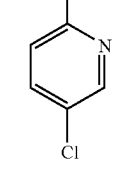 | 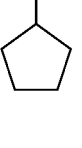 |  |  | 641.3 | 7.8 |
| 1011 | 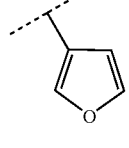 | 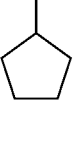 | 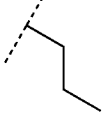 |  | 610.3 | 9.0 |
| 1012 | 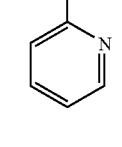 | 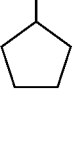 |  |  | 621.3 | 6.3 |
| 1013 | 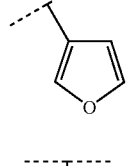 | 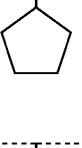 |  |  | 610.3 | 8.8 |
| 1014 | 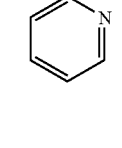 | 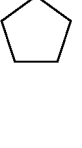 |  |  | 621.3 | 6.4 |

TABLE I-continued
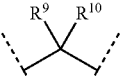
wherein R², R³, R⁵, R⁹ and R¹⁰ are given in the table.
| Cpd. # | R² | R³ | R⁵ | R⁹ R¹⁰ | m/z (M + H)⁺ | $t_R$ (min) |
|---|---|---|---|---|---|---|
| 1015 | 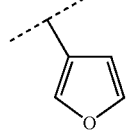 | 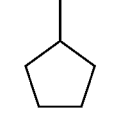 | 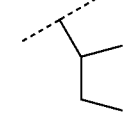 | 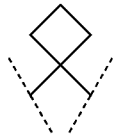 | 624.2 | 9.1 |
| 1016 | 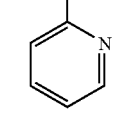 | 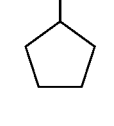 | 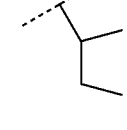 | 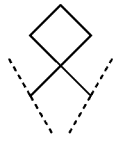 | 635.2 | 6.6 |
| 1017 | 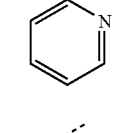 | 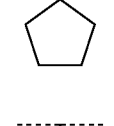 | 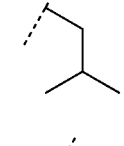 | 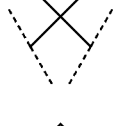 | 635.3 | 6.7 |
| 1018 | 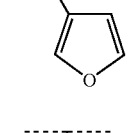 | 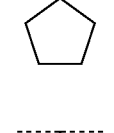 | 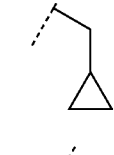 | 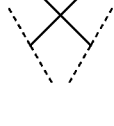 | 622.2 | 8.9 |
| 1019 | 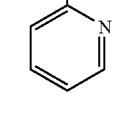 | 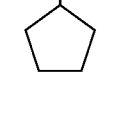 | 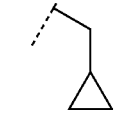 | 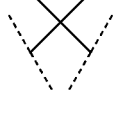 | 633.3 | 6.5 |
| 1020 | 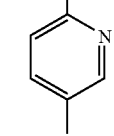 | 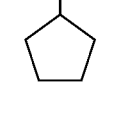 | 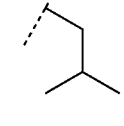 | 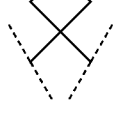 | 653.3 | 8.8 |
| 1021 | 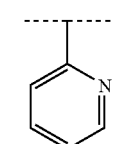 | 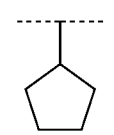 | CH₃ | 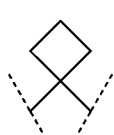 | 611.3 | 6.8 |

TABLE I-continued
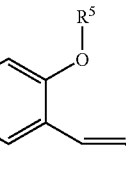
wherein R², R³, R⁵, R⁹ and R¹⁰ are given in the table.
| Cpd. # | R² | R³ | R⁵ | R⁹ R¹⁰ | m/z (M + H)⁺ | $t_R$ (min) |
|---|---|---|---|---|---|---|
| 1022 |  | 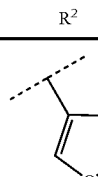 | 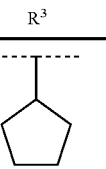 | 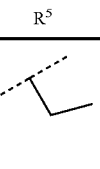 | 628.3 | 7.0 |
| 1023 | 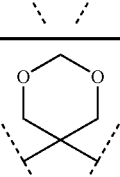 | 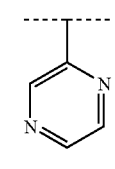 | 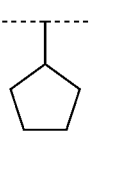 | 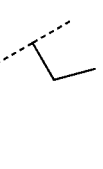 | 620.3 | 6.5 |
| 1024 | 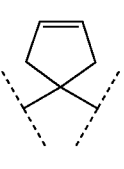 | 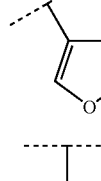 |  |  | 608.3 | 7.3 |
| 1025 | 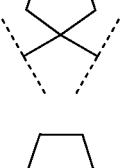 | 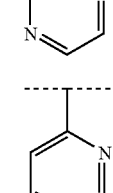 | 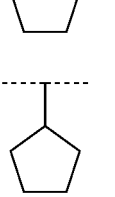 |  | 622.3 | 6.7 |
| 1026 | 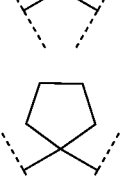 | 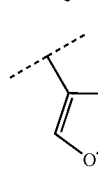 | 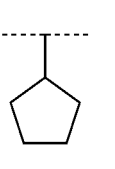 | 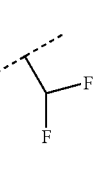 | 621.3 | 5.9 |
| 1027 | 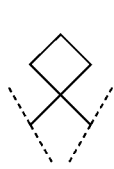 | 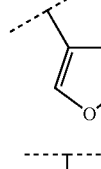 | 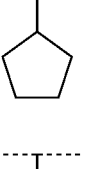 | 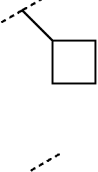 | 618.2 | 8.4 |
| 1028 | 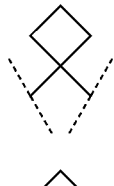 | 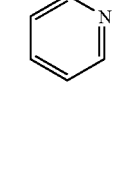 |  |  | 622.2 | 8.8 |
| 1029 |  | | | | 633.2 | 6.3 |

TABLE I-continued
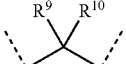
wherein R², R³, R⁵, R⁹ and R¹⁰ are given in the table.
| Cpd. # | R² | R³ | R⁵ | R⁹ R¹⁰ | m/z (M + H)⁺ | $t_R$ (min) |
|---|---|---|---|---|---|---|
| 1030 | 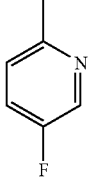 | 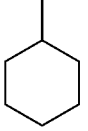 | CH₃ | 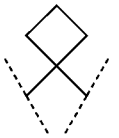 | 623.3 | 7.1 |
| 1031 | 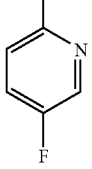 | 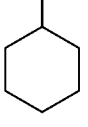 |  | 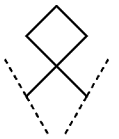 | 639.3 | 7.2 |
| 1032 | 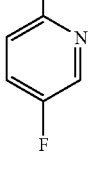 |  | CH₃ | 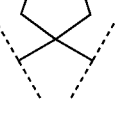 | 621.2 (M − H)⁺ | 6.9 |
| 1033 | 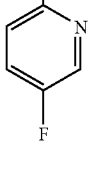 |  |  | 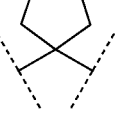 | 637.3 | 7.0 |
| 1034 | 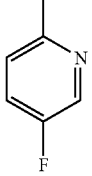 |  | 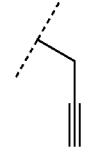 | 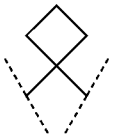 | 635.3 | 7.7 |
| 1035 | 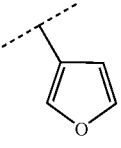 |  | 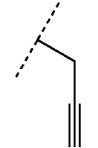 | 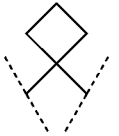 | 606.3 | 8.2 |

TABLE I-continued
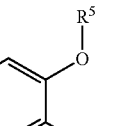
wherein R², R³, R⁵, R⁹ and R¹⁰ are given in the table.
| Cpd. # | R² | R³ | R⁵ | R⁹ R¹⁰ | m/z (M + H)⁺ | t$_R$ (min) |
|---|---|---|---|---|---|---|
| 1036 | 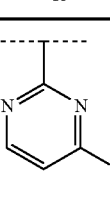 | 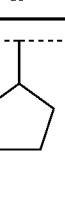 | 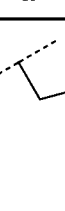 | 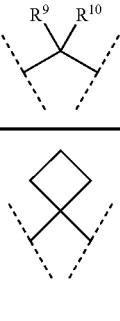 | 638.3 | 7.2 |
| 1037 | 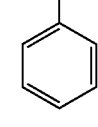 |  |  |  | 606.3 | 7.7 |
| 1038 | 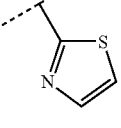 | 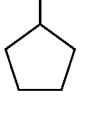 |  | 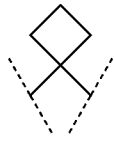 | 613.3 | 7.1 |
| 1039 | 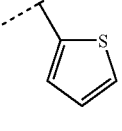 | 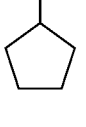 |  |  | 612.2 | 7.6 |
| 1040 | 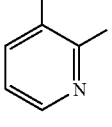 | 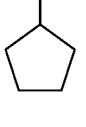 |  | 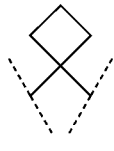 | 625.3 | 7.1 |
| 1041 | 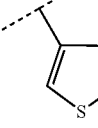 |  | 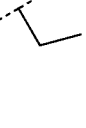 | 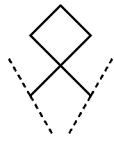 | 612.3 | 7.6 |
| 1042 | 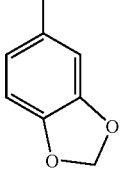 | 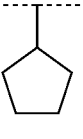 | 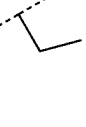 | 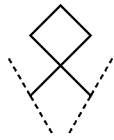 | 650.3 | 7.6 |

TABLE I-continued
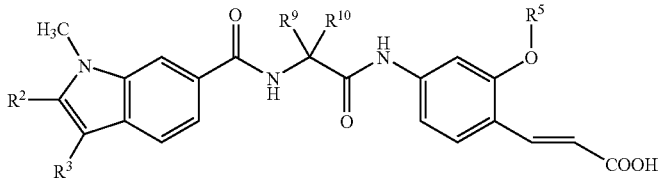
wherein R², R³, R⁵, R⁹ and R¹⁰ are given in the table.
| Cpd. # | R² | R³ | R⁵ | R⁹ R¹⁰ | m/z (M + H)⁺ | t_R (min) |
|---|---|---|---|---|---|---|
| 1043 | 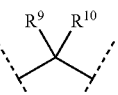 | 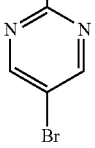 | 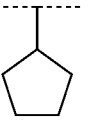 |  | 686.2 | 7.5 |
| 1044 | 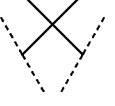 |  | 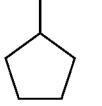 |  | 637.3 | 7.5 |
| 1045 | 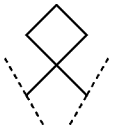 | 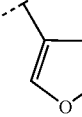 | 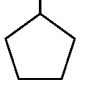 | 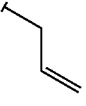 | 608.3 | 8.8 |
| 1046 | 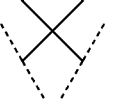 |  |  | 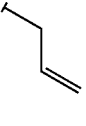 | 619.4 | 6.3 |
| 1047 | 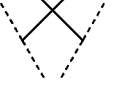 | 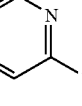 |  | 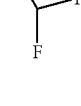 | 572.3 | 6.6 |
| 1048 | 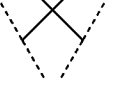 | 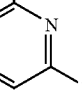 | 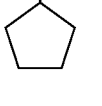 |  | 622.3 | 5.7 |
| 1049 | 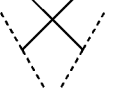 | 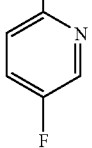 |  |  | 613.3 | 6.7 |

TABLE I-continued

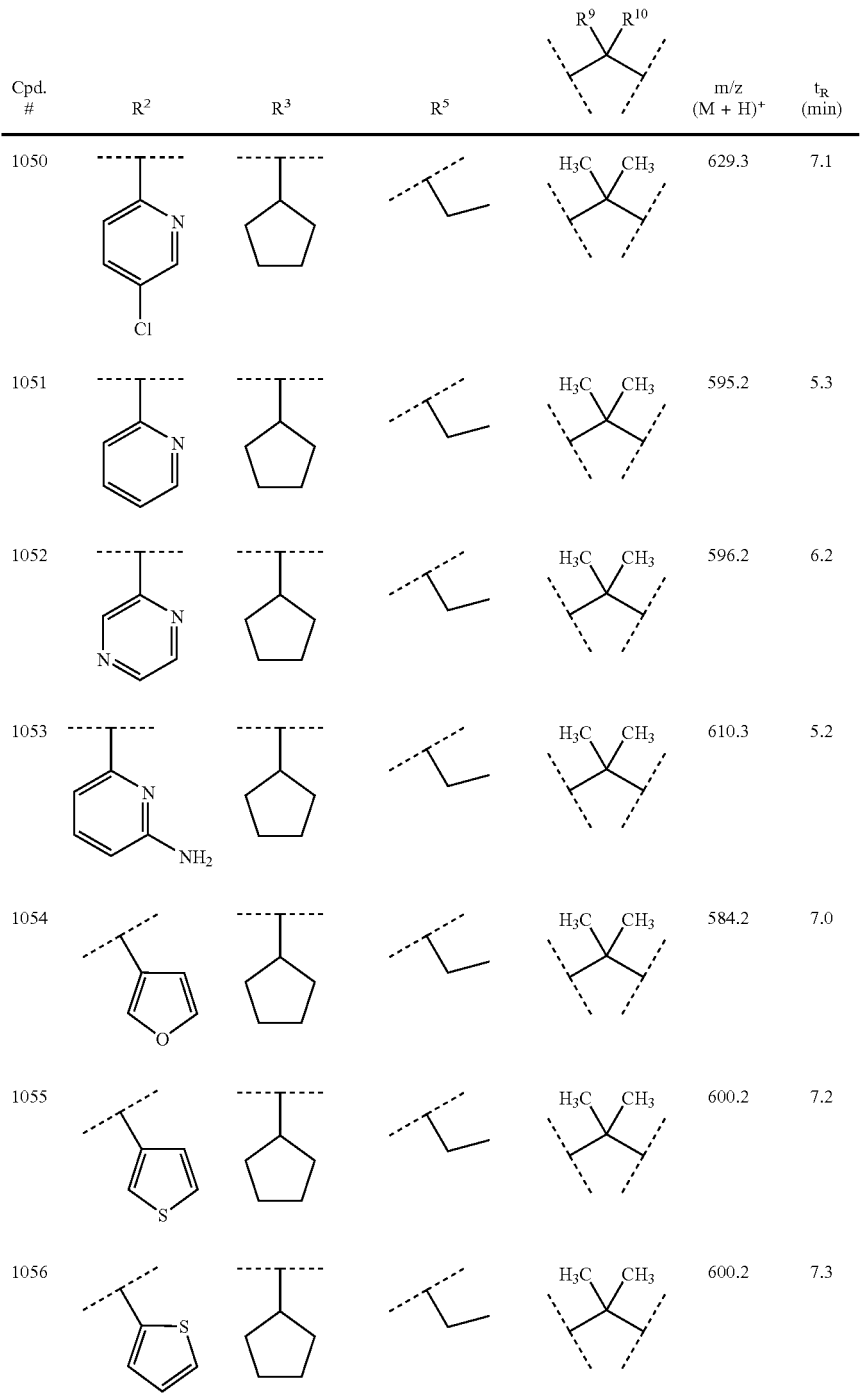

wherein R², R³, R⁵, R⁹ and R¹⁰ are given in the table.

| Cpd. # | R² | R³ | R⁵ | R⁹ R¹⁰ | m/z (M + H)⁺ | $t_R$ (min) |
|---|---|---|---|---|---|---|
| 1050 | 5-chloropyridin-2-yl | cyclopentyl | ethyl | C(CH₃)₂ (gem-dimethyl) | 629.3 | 7.1 |
| 1051 | pyridin-2-yl | cyclopentyl | ethyl | C(CH₃)₂ | 595.2 | 5.3 |
| 1052 | pyrazin-2-yl | cyclopentyl | ethyl | C(CH₃)₂ | 596.2 | 6.2 |
| 1053 | 6-aminopyridin-2-yl | cyclopentyl | ethyl | C(CH₃)₂ | 610.3 | 5.2 |
| 1054 | furan-3-yl | cyclopentyl | ethyl | C(CH₃)₂ | 584.2 | 7.0 |
| 1055 | thiophen-3-yl | cyclopentyl | ethyl | C(CH₃)₂ | 600.2 | 7.2 |
| 1056 | thiophen-2-yl | cyclopentyl | ethyl | C(CH₃)₂ | 600.2 | 7.3 |

TABLE I-continued
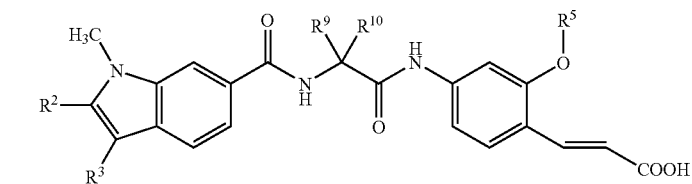
wherein R², R³, R⁵, R⁹ and R¹⁰ are given in the table.
| Cpd. # | R² | R³ | R⁵ | R⁹ R¹⁰ | m/z (M + H)⁺ | t_R (min) |
|---|---|---|---|---|---|---|
| 1057 | 2-(methylsulfonyl)pyridin-5-yl | cyclopentyl | ethyl | spiro[3.3] | 685.2 | 7.0 |
| 1058 | 5-cyanopyridin-2-yl | cyclopentyl | ethyl | spiro[3.3] | 632.2 | 7.5 |
| 1059 | ethynyl | cyclopentyl | ethyl | spiro[3.3] | 554.1 | 7.1 |
| 1060 | 2-methoxypyridin-3-yl | cyclopentyl | ethyl | C(CH₃)₂ | 625.3 | 7.3 |
| 1061 | 5-chloropyridin-2-yl | cyclopentyl | CH₃ | spiro[3.3] | 628.2 | 7.3 |
| 1062 | 2-aminopyrimidin-4-yl | cyclopentyl | ethyl | spiro[3.3] | 623.4 | 5.7 |

TABLE I-continued
wherein R², R³, R⁵, R⁹ and R¹⁰ are given in the table.
| Cpd. # | R² | R³ | R⁵ | R⁹ R¹⁰ | m/z (M + H)⁺ | $t_R$ (min) |
|---|---|---|---|---|---|---|
| 1063 | 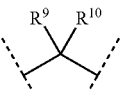 | 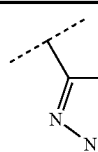 | 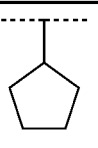 |  | 596.3 | 7.0 |
| 1064 | 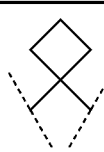 | 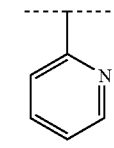 | 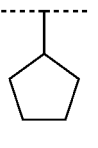 |  | 593.3 | 6.0 |
| 1065 |  | 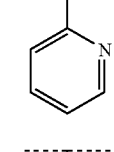 | 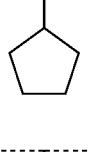 |  | 637.3 | 6.1 |
| 1066 |  | 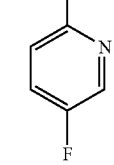 | 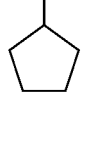 |  | 655.3 | 7.6 |
| 1067 | 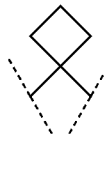 | 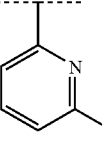 | 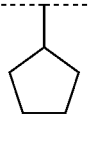 |  | 652.3 | 5.7 |
| 1068 | 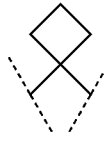 | 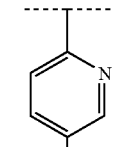 | 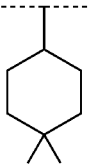 |  | 675.3 | 6.4 |
| 1069 | 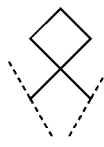 | 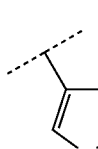 | 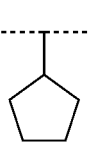 | 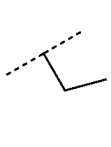 | 608.2 (M − H)⁻ | 7.2 |

TABLE I-continued
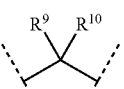
wherein R², R³, R⁵, R⁹ and R¹⁰ are given in the table.
| Cpd. # | R² | R³ | R⁵ | R⁹ R¹⁰ | m/z (M + H)⁺ | $t_R$ (min) |
|---|---|---|---|---|---|---|
| 1070 | 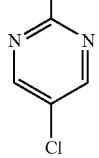 | 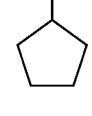 |  | 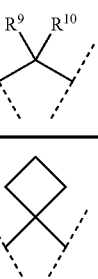 | 643.2; 642.2 | 8.1 |
| 1071 | 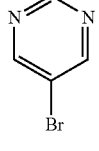 |  |  | 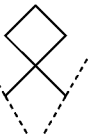 | 718.1; 716.1 | 7.9 |
| 1072 | 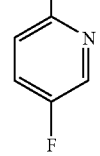 |  |  |  | 611.3 | 7.3 |
| 1073 | 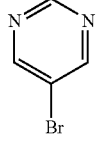 |  |  |  | did not ionize | 7.8 |
| 1074 | 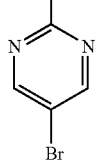 |  |  |  | did not ionize | 7.8 |
| 1075 | 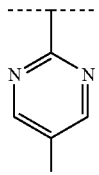 |  |  |  | 630.4 | 7.8 |

TABLE I-continued

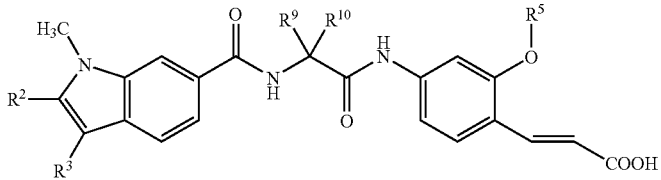

wherein R², R³, R⁵, R⁹ and R¹⁰ are given in the table.

| Cpd. # | R² | R³ | R⁵ | R⁹ R¹⁰ | m/z (M + H)⁺ | $t_R$ (min) |
|---|---|---|---|---|---|---|
| 1076 | 5-chloropyrimidin-2-yl | cyclopentyl | ethyl | cyclopropylidene | 628.3 | 7.7 |
| 1077 | 5-chloropyrimidin-2-yl | cyclopentyl | CH₂CH₂OMe | cyclobutylidene | did not ionize | 7.8 |
| 1078 | pyridin-2-yl | cyclopentyl | CH₂CH₂OMe | C(CH₃)₂ | 625.4 | 5.7 |
| 1079 | CH₃ | cyclopentyl | ethyl | cyclobutylidene | 544.3 | 7.4 |
| 1080 | 5-fluoropyridin-2-yl | cyclopentyl | CH₂CH₂OMe | C(CH₃)₂ | 643.4 | 7.2 |
| 1081 | 5-chloropyrimidin-2-yl | cyclopentyl | CH₂CH₂OMe | C(CH₃)₂ | 660.3 | 7.5 |

TABLE I-continued

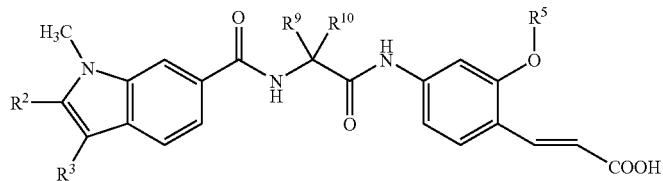

wherein R², R³, R⁵, R⁹ and R¹⁰ are given in the table.

| Cpd. # | R² | R³ | R⁵ | R⁹ R¹⁰ | m/z (M + H)⁺ | t_R (min) |
|---|---|---|---|---|---|---|
| 1082 | 5-Br-pyrimidin-2-yl | cyclopentyl | -CH₂CH₂CH₂OMe | H₃C, CH₃ (gem-dimethyl) | 704.3 | 7.6 |
| 1083 | 5-OMe-pyrimidin-2-yl | cyclopentyl | -CH₂CH₂CH₂OMe | spiro-cyclobutyl | 668.1 | 7.2 |
| 1084 | 5-Cl-pyrimidin-2-yl | cyclopentyl | -CH₂-(pyridin-3-yl) | spiro-cyclobutyl | 705.3 | 6.0 |
| 1085 | 5-Cl-pyrimidin-2-yl | cyclopentyl | -CH₂CH₂CH₂-morpholin-4-yl | spiro-cyclobutyl | 727.3 | 5.9 |
| 1086 | 5-Br-pyrimidin-2-yl | cyclopentyl | -CH₂-(pyridin-3-yl) | spiro-cyclobutyl | 749.2 | 6.1 |
| 1087 | 5-Br-pyrimidin-2-yl | cyclopentyl | -CH₂CH₂CH₂-morpholin-4-yl | spiro-cyclobutyl | 771.3 | 6.0 |

TABLE 1-continued

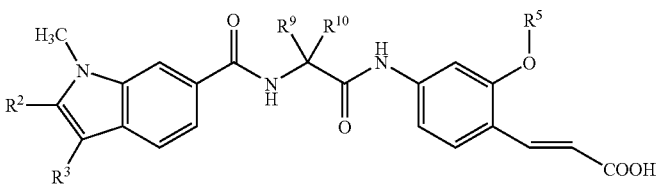

wherein $R^2$, $R^3$, $R^5$, $R^9$ and $R^{10}$ are given in the table.

| Cpd. # | $R^2$ | $R^3$ | $R^5$ | $R^9\ R^{10}$ | m/z $(M + H)^+$ | $t_R$ (min) |
|---|---|---|---|---|---|---|
| 1088 | pyrimidin-5-yl | cyclopentyl | ethyl | cyclobutylidene | 608.3 | 6.7 |

TABLE 2

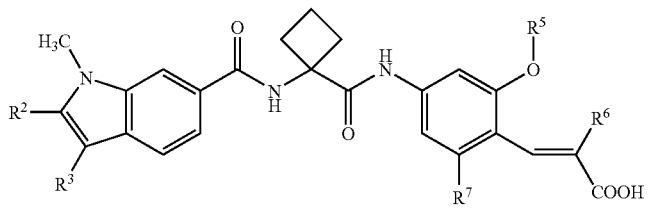

wherein $R^2$, $R^3$, $R^5$, $R^6$ and $R^7$ are given in the table.

| Cpd. # | $R^2$ | $R^3$ | $R^5$ | $R^6$ | $R^7$ | m/z $(M + H)^+$ | $t_R$ (min) |
|---|---|---|---|---|---|---|---|
| 2001 | 5-fluoropyridin-2-yl | cyclopentyl | CH$_3$ | CH$_3$ | H | 625.3 | 7.7 |
| 2002 | 5-fluoropyridin-2-yl | cyclopentyl | ethyl | CH$_3$ | H | 639.3 | 7.8 |
| 2003 | 5-fluoropyridin-2-yl | cyclopentyl | ethyl | F | H | 643.3 | 8.0 |

TABLE 2-continued
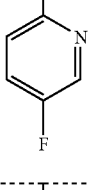
wherein R², R³, R⁵, R⁶ and R⁷ are given in the table.
| Cpd. # | R² | R³ | R⁵ | R⁶ | R⁷ | m/z (M + H)⁺ | $t_R$ (min) |
|---|---|---|---|---|---|---|---|
| 2004 |  |  |  | 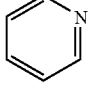 | H | 653.3 | 8.0 |
| 2005 |  | 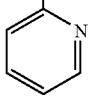 | CH₃ | H | —OCH₃ | 623.2 | 5.9 |
| 2006 |  |  | 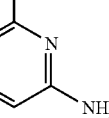 | F | H | 625.3 | 6.0 |
| 2007 |  |  | 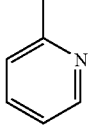 | F | H | 640.3 | 5.7 |
TABLE 3
wherein R², R³, R⁵, R⁹, and R¹⁰ are given in the table.
| Cpd. # | R² | R³ | R⁵ | R⁹ R¹⁰ | m/z (M + H)⁺ | $t_R$ (min) |
|---|---|---|---|---|---|---|
| 3001 |  |  |  |  | 593.3 | 5.5 |

TABLE 3-continued wherein R², R³, R⁵, R⁹, and R¹⁰ are given in the table.

| Cpd. # | R² | R³ | R⁵ | R⁹ R¹⁰ | m/z (M + H)⁺ | $t_R$ (min) |
|---|---|---|---|---|---|---|
| 3002 | 2-pyridyl | cyclohexyl | ethyl | cyclobutylidene | 607.3 | 5.8 |
| 3003 | 3-furyl | cyclopentyl | ethyl | cyclobutylidene | 582.3 | 6.9 |
| 3004 | 3-furyl | cyclohexyl | ethyl | cyclobutylidene | Did not ionize | 7.2 |
| 3005 | 2-pyridyl | cyclohexyl | ethyl | H₃C, CH₃ | 595.2 | 5.5 |
| 3006 | 3-furyl | cyclopentyl | ethyl | H₃C, CH₃ | 570.3 | 6.8 |
| 3007 | 3-furyl | cyclopentyl | CH₃ | cyclobutylidene | 568.3 | 6.9 |
| 3008 | 2-pyridyl | cyclohexyl | CH₃ | cyclobutylidene | 593.3 | 5.7 |
| 3009 | 2-thiazolyl | cyclohexyl | ethyl | cyclobutylidene | 613.3 | 7.1 |

TABLE 3-continued
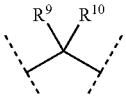
wherein R², R³, R⁵, R⁹, and R¹⁰ are given in the table.
| Cpd. # | R² | R³ | R⁵ | R⁹ R¹⁰ | m/z (M + H)⁺ | t_R (min) |
|---|---|---|---|---|---|---|
| 3010 | 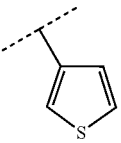 |  | 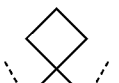 | 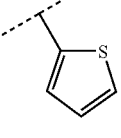 | 612.3 | 7.4 |
| 3011 |  |  | 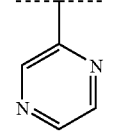 |  | 612.3 | 7.4 |
| 3012 | 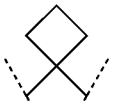 | 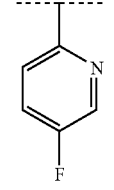 |  |  | 608.4 | 6.6 |
| 3013 | 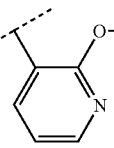 |  | 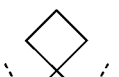 | 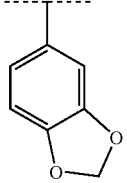 | 625.4 | 7.2 |
| 3014 |  | | | | 637.4 | 7.1 |
| 3015 |  | | | | 650.4 | 7.4 |
| 3016 | 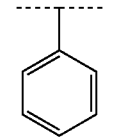 |  | 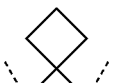 | | 606.4 | 7.5 |

TABLE 3-continued
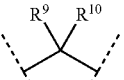
wherein R², R³, R⁵, R⁹, and R¹⁰ are given in the table.
| Cpd. # | R² | R³ | R⁵ | R⁹ R¹⁰ | m/z (M + H)⁺ | t_R (min) |
|---|---|---|---|---|---|---|
| 3017 | 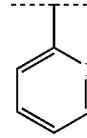 | 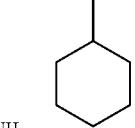 | 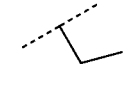 | 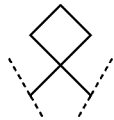 | 622.4 | 5.2 |
| 3018 | 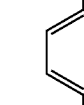 | 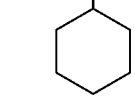 |  | 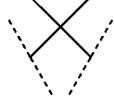 | 655.3 | 7.7 |
TABLE 4
wherein R², R³, R⁵, R⁶, R⁹, and R¹⁰ are given in the table.
| Cpd. # | R² | R³ | R⁵ | R⁶ | R⁹ R¹⁰ | m/z (M + H)⁺ | t_R (min) |
|---|---|---|---|---|---|---|---|
| 4001 | 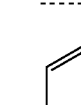 | 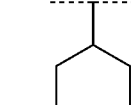 | 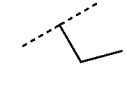 | H | 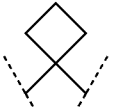 | 639.3 | 7.9 |
| 4002 | 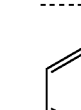 | 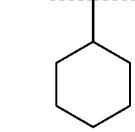 | CH₃ | H |  | 625.3 | 7.0 |

TABLE 4-continued
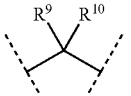
wherein R², R³, R⁵, R⁶, R⁹, and R¹⁰ are given in the table.
| Cpd. # | R² | R³ | R⁵ | R⁶ | R⁹ R¹⁰ | m/z (M + H)⁺ | $t_R$ (min) |
|---|---|---|---|---|---|---|---|
| 4003 | 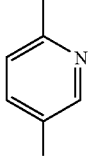 | 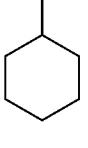 |  | H | 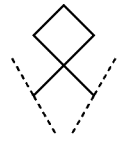 | 649.3 | 8.0 |
| 4004 | 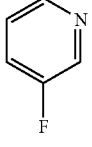 | 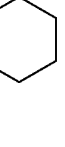 | CH₃ | CH₃ | 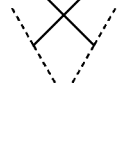 | 639.3 | 7.8 |
| 4005 | 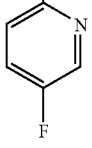 | 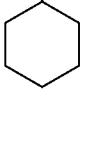 |  | CH₃ | 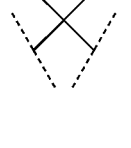 | 653.3 | 8.0 |
| 4006 | 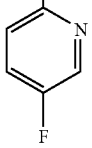 | 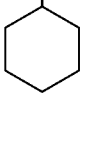 | CH₃ | H | 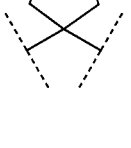 | 637.3 | 7.2 |
| 4007 | 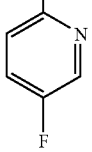 | 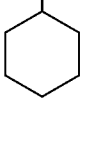 |  | H | 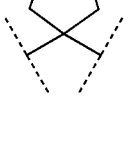 | 651.3 | 7.4 |
| 4008 | 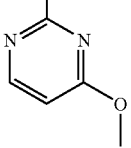 | 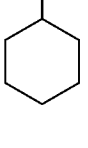 |  | H | 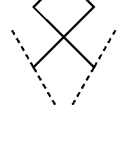 | 652.3 | 7.1 |

TABLE 4-continued

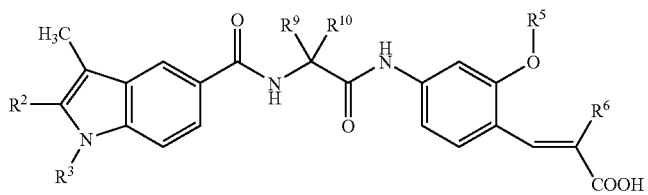

wherein $R^2$, $R^3$, $R^5$, $R^6$, $R^9$, and $R^{10}$ are given in the table.

| Cpd. # | $R^2$ | $R^3$ | $R^5$ | $R^6$ | $R^9$ $R^{10}$ | m/z (M + H)$^+$ | $t_R$ (min) |
|---|---|---|---|---|---|---|---|
| 4009 | 5-fluoropyridin-2-yl | cyclohexyl | ethyl | F | cyclobutylidene | 657.3 | 8.3 |
| 4010 | phenyl | cyclohexyl | ethyl | H | cyclobutylidene | 620.3 | 7.8 |
| 4011 | thiazol-2-yl | cyclohexyl | ethyl | H | cyclobutylidene | 627.3 | 7.2 |
| 4012 | thien-2-yl | cyclohexyl | ethyl | H | cyclobutylidene | 626.3 | 7.7 |
| 4013 | thien-3-yl | cyclohexyl | ethyl | H | cyclobutylidene | 626.3 | 7.7 |
| 4014 | benzo[1,3]dioxol-5-yl | cyclohexyl | ethyl | H | cyclobutylidene | 664.3 | 7.6 |
| 4015 | 5-bromopyrimidin-2-yl | cyclohexyl | ethyl | H | cyclobutylidene | 700.2 | 7.6 |

TABLE 4-continued

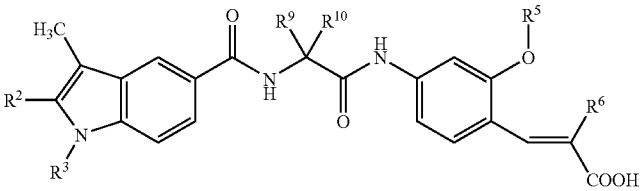

wherein R², R³, R⁵, R⁶, R⁹, and R¹⁰ are given in the table.

| Cpd. # | R² | R³ | R⁵ | R⁶ | R⁹ R¹⁰ | m/z (M + H)⁺ | $t_R$ (min) |
|---|---|---|---|---|---|---|---|
| 4016 | 5-fluoropyridin-2-yl | cyclohexyl | ethyl | alkenyl | cyclobutylidene | 667.3 | 8.2 |
| 4017 | 5-fluoropyridin-2-yl | cyclohexyl | CH₃ | alkenyl | cyclobutylidene | 653.3 | 8.0 |
| 4018 | pyridin-2-yl | cyclohexyl | ethyl | H | cyclobutylidene | 621.3 | 5.6 |
| 4019 | furan-3-yl | cyclohexyl | ethyl | H | cyclobutylidene | 610.3 | 7.3 |
| 4020 | pyrazin-2-yl | cyclohexyl | ethyl | H | cyclobutylidene | 622.3 | 6.6 |
| 4021 | pyridin-2-yl | cyclohexyl | ethyl | H | C(CH₃)₂ | 609.3 | 5.3 |
| 4022 | furan-3-yl | cyclohexyl | ethyl | H | C(CH₃)₂ | 598.3 | 7.1 |

TABLE 4-continued
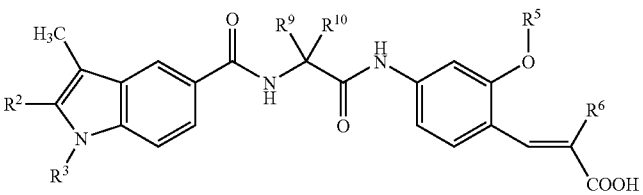
wherein R², R³, R⁵, R⁶, R⁹, and R¹⁰ are given in the table.
| Cpd. # | R² | R³ | R⁵ | R⁶ | R⁹ R¹⁰ | m/z (M + H)⁺ | $t_R$ (min) |
|---|---|---|---|---|---|---|---|
| 4023 | 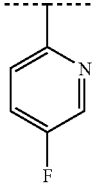 | 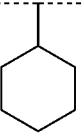 |  | H | 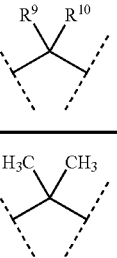 | 627.3 | 6.9 |
| 4024 | 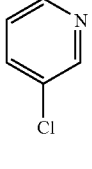 | 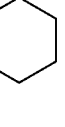 |  | H |  | 643.3 | 7.3 |
| 4025 | 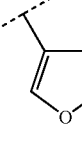 | 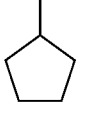 |  | H | 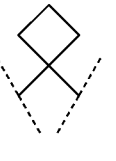 | 596.2 | 7.1 |
| 4026 | 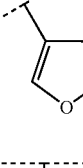 |  |  | H | 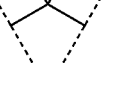 | 584.2 | 6.8 |
| 4027 | 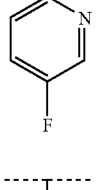 | 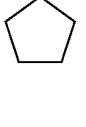 |  | H | 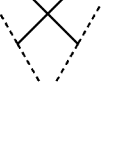 | 625.2 | 6.9 |
| 4028 | 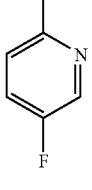 | 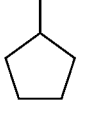 |  | H |  | 613.2 | 6.6 |

TABLE 4-continued
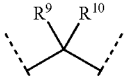
wherein R², R³, R⁵, R⁶, R⁹, and R¹⁰ are given in the table.
| Cpd. # | R² | R³ | R⁵ | R⁶ | R⁹ R¹⁰ | m/z (M + H)⁺ | $t_R$ (min) |
|---|---|---|---|---|---|---|---|
| 4029 | 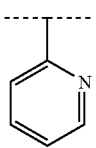 | 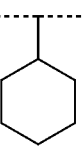 |  | F | 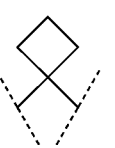 | 639.3 | 5.9 |
| 4030 | 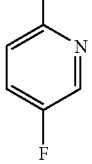 | 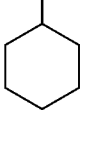 | 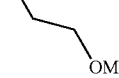 | H | 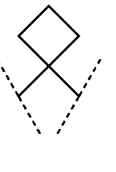 | 669.3 | 7.7 |
| 4031 | 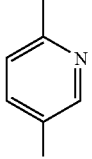 | 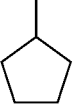 | 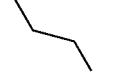 | H | 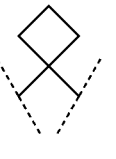 | 655.4 | 7.4 |
| 4032 | 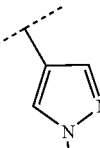 | 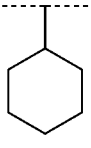 |  | H | 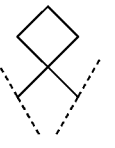 | 654.4 | 6.9 |
| 4033 | 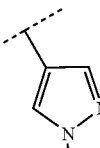 | 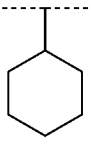 |  | H | 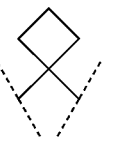 | 624.3 | 7.2 |
| 4034 | 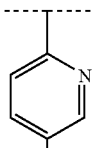 | 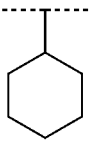 |  | H | 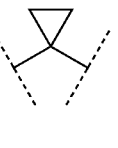 | 625.3 | 7.5 |

TABLE 4-continued

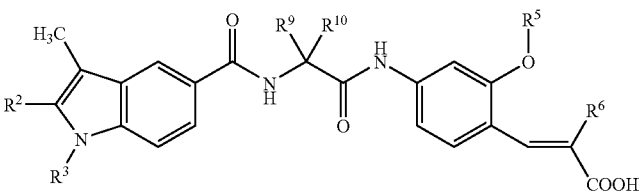

wherein $R^2$, $R^3$, $R^5$, $R^6$, $R^9$, and $R^{10}$ are given in the table.

| Cpd. # | $R^2$ | $R^3$ | $R^5$ | $R^6$ | $R^9$ $R^{10}$ | m/z (M + H)$^+$ | $t_R$ (min) |
|---|---|---|---|---|---|---|---|
| 4035 | 5-fluoropyridin-2-yl | cyclohexyl | H | H | cyclobutylidene (spiro) | 611.3 | 7.2 |
| 4036 | 5-fluoropyridin-2-yl | cyclohexyl | -CH₂CH₂CH₂OMe | H | H₃C, CH₃ | 657.4 | 7.4 |
| 4037 | 5-fluoropyridin-2-yl | cyclohexyl | -CH₂CH(Me)CH₂OMe | H | H₃C, CH₃ | 683.5 | 7.3 |
| 4038 | 5-fluoropyridin-2-yl | cyclohexyl | -CH₂CH₂CH₂NHSO₂Me | H | cyclobutylidene (spiro) | 732.4 | 7.3 |
| 4039 | 5-chloropyrimidin-2-yl | cyclohexyl | -CH(Me)CH₂CH₃ | H | cyclobutylidene (spiro) | 656.4 | 7.6 |
| 4040 | 5-fluoropyridin-2-yl | cyclohexyl | -CH₂CH₂CH₂N(Me)₂ | H | cyclobutylidene (spiro) | 682.5 | 6.5 |

TABLE 4-continued
wherein R², R³, R⁵, R⁶, R⁹, and R¹⁰ are given in the table.
| Cpd. # | R² | R³ | R⁵ | R⁶ | R⁹ R¹⁰ | m/z (M + H)⁺ | $t_R$ (min) |
|---|---|---|---|---|---|---|---|
| 4041 | 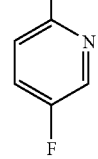 | 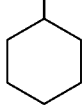 |  | H |  | 683.4 | 7.3 |
| 4042 | 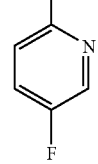 | 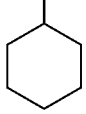 |  | H | 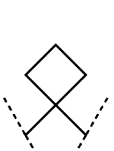 | 696.5 | 5.8 |
| 4043 | 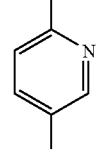 | 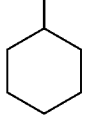 |  | H |  | 694.5 | 5.7 |
| 4044 | 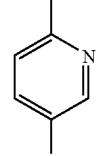 | 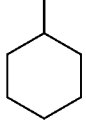 |  | H |  | 691.4 | 7.5 |
| 4045 | 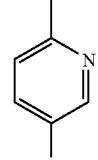 | 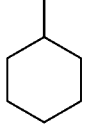 |  | H |  | 691.4 | 7.5 |
| 4046 | 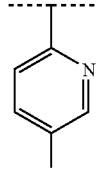 | 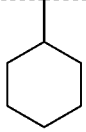 | 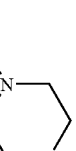 | H |  | 724.5 | 5.8 |

TABLE 4-continued

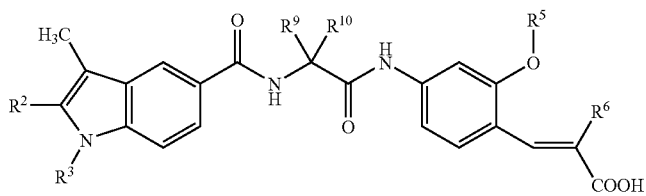

wherein R², R³, R⁵, R⁶, R⁹, and R¹⁰ are given in the table.

| Cpd. # | R² | R³ | R⁵ | R⁶ | R⁹ R¹⁰ | m/z (M + H)⁺ | $t_R$ (min) |
|---|---|---|---|---|---|---|---|
| 4047 | 5-F-pyridin-2-yl | cyclohexyl | CH₂-(pyridin-3-yl) | H | cyclobutyl | 702.4 | 5.9 |
| 4048 | 5-F-pyridin-2-yl | cyclohexyl | CH(CH₃)CH₂OMe | H | cyclobutyl | 683.5 | 7.3 |
| 4049 | 5-F-pyridin-2-yl | cyclohexyl | CH₂-(tetrahydrofuran-2-yl) | H | cyclobutyl | 695.5 | 7.3 |

TABLE 5

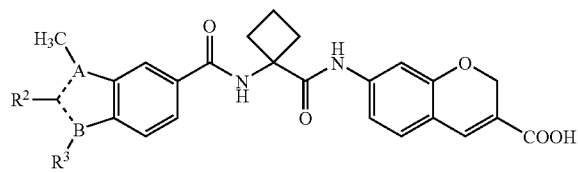

wherein R², R³, A and B are given in the table and wherein
---- between two C-atoms represents a double bond and ----
between a C-atom and a N-atom represents a single bond.

| Cpd. # | A | B | R² | R³ | m/z (M + H)⁺ | $t_R$ (min) |
|---|---|---|---|---|---|---|
| 5001 | N | C | 5-F-pyridin-2-yl | cyclopentyl | 609.3 | 7.5 |

TABLE 5-continued

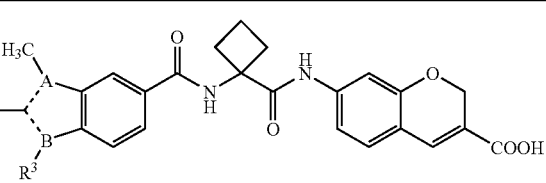

wherein R², R³, A and B are given in the table and wherein
---- between two C-atoms represents a double bond and ----
between a C-atom and a N-atom represents a single bond.

| Cpd. # | A | B | R² | R³ | m/z (M + H)⁺ | $t_R$ (min) |
|---|---|---|---|---|---|---|
| 5002 | N | C | pyridin-2-yl | cyclopentyl | 591.3 | 6.0 |

TABLE 5-continued wherein $R^2$, $R^3$, A and B are given in the table and wherein ----- between two C-atoms represents a double bond and ----- between a C-atom and a N-atom represents a single bond.

| Cpd. # | A | B | $R^2$ | $R^3$ | m/z (M + H)$^+$ | $t_R$ (min) |
|---|---|---|---|---|---|---|
| 5003 | C | N | 5-fluoropyridin-2-yl | cyclohexyl | 623.3 | 7.7 |

What is claimed is:

1. A compound of formula (I):

(I)

wherein:
either A or B is N and the other B or A is C, wherein— between two C-atoms represents a double bond and— between a C-atom and a N-atom represents a single bond;

$R^1$ is H or $(C_{1-6})$alkyl;

$R^2$ is $(C_{1-6})$alkyl, $(C_{2-6})$alkynyl, —C(=O)—$(C_{1-6})$alkyl, aryl or Het; the aryl and Het being optionally substituted with $R^{21}$;
  wherein $R^{21}$ is one, two or three substituents each independently selected from $(C_{1-6})$alkyl, $(C_{3-7})$cycloalkyl, Het, —CN, —NH$_2$, —NH$(C_{1-6})$alkyl, —N$((C_{1-6})$alkyl$)_2$, halo, —O—$(C_{1-6})$alkyl, —S—$(C_{1-6})$alkyl, —SO—$(C_{1-6})$alkyl and —SO$_2$—$(C_{1-6})$alkyl;
    wherein the $(C_{1-6})$alkyl, —O—$(C_{1-6})$alkyl, —S—$(C_{1-6})$alkyl, —SO—$(C_{1-6})$alkyl and —SO$_2$—$(C_{1-6})$alkyl are each optionally substituted with one, two or three halo substituents;

$R^3$ is $(C_{5-6})$cycloalkyl, optionally substituted with from one to four halo substituents;

$R^5$ is selected from H, $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, Het and Het-$(C_{1-6})$alkyl-;
  wherein the $(C_{1-6})$alkyl is optionally substituted with from one to three substituents each independently selected from halo, cyano, $(C_{1-6})$alkoxy, —NH$(C_{1-6})$alkyl, —N$((C_{1-6})$alkyl$)_2$ and —NHSO$_2(C_{1-6})$alkyl; and
  wherein each of the Het and the Het portion of the Het-$(C_{1-6})$alkyl- is optionally substituted with $(C_1)$alkyl; and $R^6$ is selected from H, $(C_{1-6})$alkyl and halo; or $R^5$ and $R^6$ are linked such that the group of the subformula is a group of formula wherein n is 0, 1 or 2; and wherein $R^{50}$ is selected independently in each instance from H, halo, cyano, $(C_{1-6})$alkoxy, $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, Het and Het-$(C_{1-6})$alkyl-;
  wherein the $(C_{1-6})$alkyl is optionally substituted with from one to three substituents each independently selected from halo, cyano, $(C_{1-6})$alkoxy, —NH$(C_{1-6})$alkyl, —N$((C_{1-6})$alkyl$)_2$ and —NHSO$_2$-$(C_{1-6})$alkyl; and wherein each of the Het and the Het portion of the Het-$(C_{1-6})$alkyl- is optionally substituted with $(C_{1-6})$alkyl;

$R^7$ is selected from H, $(C_{1-6})$alkyl, $(C_{1-6})$alkoxy, $(C_{1-6})$alkylthio, —NH$_2$, —NH$(C_{1-6})$alkyl, —N$((C_{1-6})$alkyl$)_2$ and halo;

$R^9$ and $R^{10}$ are each independently selected from $(C_{1-6})$alkyl; or $R^9$ and $R^{10}$ are covalently bonded together to form $(C_{3-7})$cycloalkyl, $(C_{5-7})$cycloalkenyl or a 4-, 5- or 6-membered heterocycle having from 1 to 3 heteroatoms each independently selected from O, N, and S;
  wherein the cycloalkyl, cycloalkenyl or heterocycle is optionally substituted with $(C_{1-4})$alkyl;

wherein Het is defined as a 4- to 7-membered heterocycle having 1 to 4 heteroatoms each independently selected from O, N and S, which may be saturated, unsaturated or aromatic, and which is optionally fused to at least one other cycle to form a 7 to 14-membered heteropolycycle having wherever possible 1 to 5 heteroatoms, each independently selected from O, N and S, the heteropolycycle being saturated, unsaturated or aromatic;

or an enantiomer, diastereoisomer or tautomer thereof, including a salt, ester or derivative thereof.

2. The compound according to claim 1 of formula (Ia):

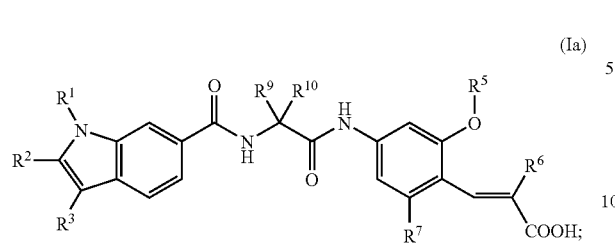

(Ia)

wherein $R^1$, $R^2$, $R^3$, $R^5$, $R^6$, $R^7$, $R^9$ and $R^{10}$ are defined as in claim 1.

3. The compound according to claim 1 of formula (Ib):

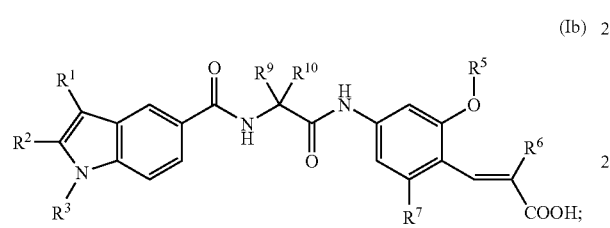

(Ib)

wherein $R^1$, $R^2$, $R^3$, $R^5$, $R^6$, $R^7$, $R^9$ and $R^{10}$ are defined as in claim 1.

4. The compound according to claim 1 wherein $R^1$ is H or methyl.

5. The compound according to claim 4 wherein $R^1$ is methyl.

6. The compound according to claim 1 wherein $R^2$ is $(C_{1-6})$alkyl, $(C_{2-6})$alkynyl or —C(=O)—$(C_{1-6})$alkyl.

7. The compound according to claim 1 wherein $R^2$ is aryl or Het, wherein Het is a 5- or 6-membered monocyclic aromatic heterocycle having 1 to 4 heteroatoms each independently selected from O, N and S, which is optionally fused to one other cycle to form an 8- to 11-membered aromatic heteropolycycle having wherever possible 1 to 5 heteroatoms, each independently selected from O, N and S;

wherein $R^2$ is unsubstituted or substituted with $R^{21}$, wherein $R^{21}$ is defined as in claim 1.

8. The compound according to claim 7 wherein $R^2$ is phenyl or Het, wherein Het is selected from

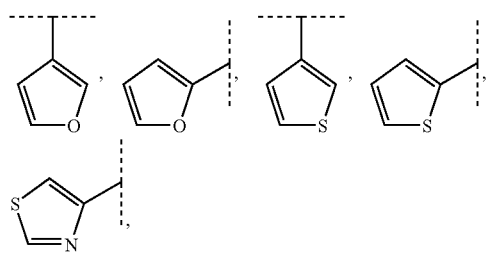

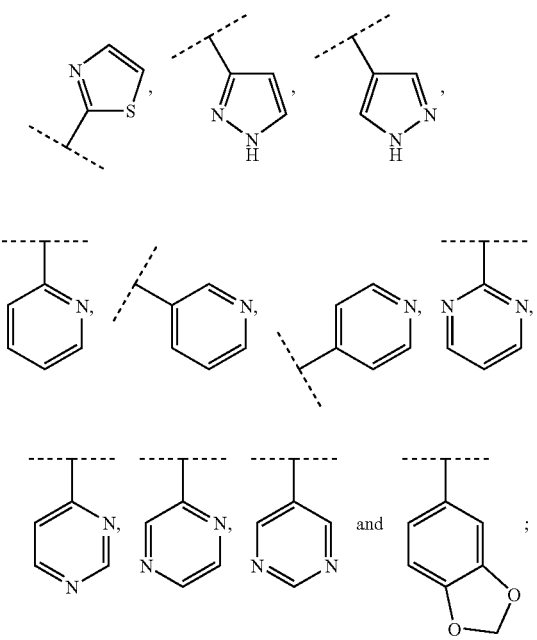

wherein $R^2$ is unsubstituted or substituted with $R^{21}$, wherein $R^{21}$ is defined as in claim 1.

9. The compound according to claim 7 wherein $R^{21}$ is one, two or three substituents each independently selected from $(C_{1-3})$alkyl, $(C_{3-6})$cycloalkyl, —CN, —$NH_2$, —NH$(C_{1-3})$alkyl, —N(($C_{1-3}$)alkyl)$_2$, halo, —O—$(C_{1-3})$alkyl, —S—$(C_{1-3})$alkyl, —SO—$(C_{1-3})$alkyl and —$SO_2$—$(C_{1-3})$alkyl;

wherein the $(C_{1-3})$alkyl, —O—$(C_{1-3})$alkyl, —S—$(C_{1-3})$alkyl, —SO—$(C_{1-3})$alkyl and —$SO_2$—$(C_{1-3})$alkyl are each optionally substituted with one, two or three halo substituents.

10. The compound according to claim 9 wherein $R^{21}$ is one, two or three substituents each independently selected from fluoro, chloro, bromo, methyl, ethyl, propyl, 1-methylethyl, trifluoromethyl, cyclopropyl, cyclobutyl, cyclopentyl, cyclohexyl, methoxy, ethoxy, propoxy, 1-methylethoxy, methylthio, ethylthio, propylthio, 1-methylethylthio, amino, N-methylamino, N,N-dimethylamino, —$SO_2CH_3$ and cyano.

11. The compound according to claim 10 wherein $R^{21}$ is one or two substituents each independently selected from fluoro, chloro, bromo, methyl, methoxy, amino, —$SO_2CH_3$ and cyano.

12. The compound according to claim 1 wherein $R^3$ is cyclopentyl or cyclohexyl, each being optionally substituted with one to four fluoro substituents.

13. The compound according to claim 12 wherein $R^3$ is cyclopentyl optionally substituted with one to four fluoro substituents.

14. The compound according to claim 12 wherein $R^3$ is cyclohexyl optionally substituted with one to four fluoro substituents.

15. The compound according to claim 1 wherein $R^5$ is selected from $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, Het and Het-$(C_{1-6})$alkyl-; wherein the Het and the Het portion of the Het-$(C_{1-6})$alkyl- are each selected from a 5- or 6-membered saturated, unsaturated or aromatic monocyclic heterocycle, having one to three heteroatoms each independently selected from N, O and S; and wherein the $(C_{1-6})$alkyl is optionally substituted with from one to three substituents each independently selected from halo, cyano, $(C_{1-6})$alkoxy, —NH$(C_{1-6})$alkyl, —N$((C_{1-6})$alkyl$)_2$ and —NHSO$_2(C_{1-6})$alkyl; and wherein each of the Het and the Het portion of the Het-$(C_{1-6})$alkyl- is optionally substituted with $(C_{1-6})$ alkyl.

16. The compound according to claim 15 wherein $R^5$ is selected from methyl, ethyl, propyl, 1-methylethyl, butyl, 1-methylpropyl, 2-methylpropyl, 1,1-dimethylethyl, 2-propenyl, 2-propynyl, cyclopropyl, cyclobutyl, cyclopropylmethyl, cyclobutylmethyl,

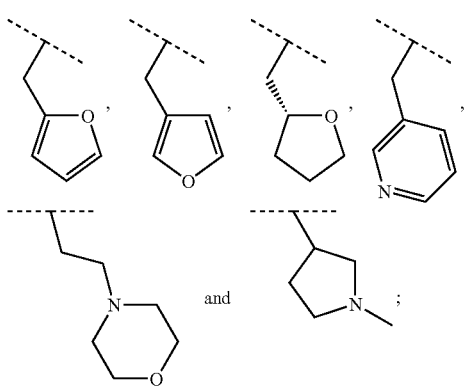

and wherein the methyl, ethyl, propyl, 1-methylethyl, butyl, 1-methylpropyl, 2-methylpropyl and 1,1-dimethylethyl are each optionally substituted with from one to three substituents each independently selected from fluoro, methoxy, ethoxy, —N(CH$_3$)$_2$, and —NHSO$_2$CH$_3$.

17. The compound according to claim 1 wherein $R^6$ is H, methyl, ethyl or fluoro.

18. The compound according to claim 1 wherein $R^5$ and $R^6$ are linked such that the group of the subformula

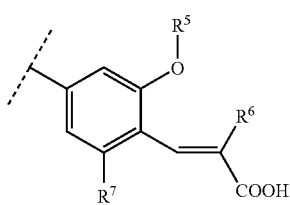

is a group of formula

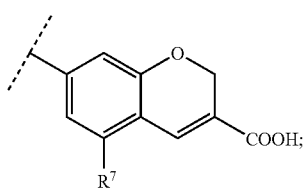

wherein $R^7$ is defined as in claim 1.

19. The compound according to claim 1 wherein $R^7$ is H, methyl, ethyl, methoxy or ethoxy.

20. The compound according to claim 19 wherein $R^7$ is H or methoxy.

21. The compound according to claim 1 wherein $R^9$ and $R^{10}$ are each independently selected from $(C_{1-3})$alkyl or $R^9$ and $R^{10}$ are covalently bonded together to form $(C_{3-6})$cycloalkyl, $(C_{5-6})$cycloalkenyl or a 5- or 6-membered heterocycle having from 1 to 2 heteroatoms each independently selected from O and N; wherein the cycloalkyl, cycloalkenyl and heterocycle are each optionally substituted with $(C_{1-4})$alkyl.

22. The compound according to claim 21 wherein the group

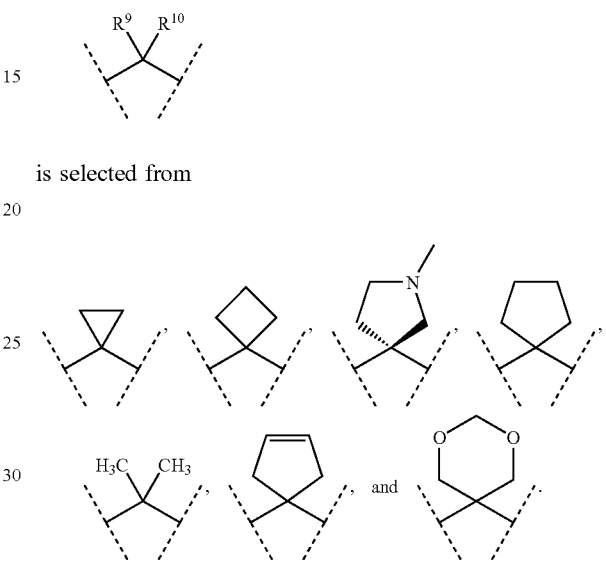

is selected from

23. The compound according to claim 1 wherein:
$R^1$ is H or methyl;
$R^2$ is aryl or Het, wherein Het is a 5- or 6-membered monocyclic aromatic heterocycle having 1 to 4 heteroatoms each independently selected from O, N and S, which is optionally fused to one other cycle to form an 8- to 11-membered aromatic heteropolycycle having wherever possible 1 to 5 heteroatoms, each independently selected from O, N and S;
wherein the aryl and Het are each optionally substituted with $R^{21}$,
wherein $R^{21}$ is one, two or three substituents each independently selected from $(C_{1-3})$alkyl, $(C_{3-6})$cycloalkyl, —CN, —NH$_2$, —NH$(C_{1-3})$alkyl, —N$((C_{1-3})$alkyl$)_2$, halo, —O—$(C_{1-3})$alkyl, —S—$(C_{1-3})$alkyl, —SO—$(C_{1-3})$alkyl and —SO$_2$-$(C_{1-3})$alkyl;
wherein the $(C_{1-3})$alkyl, —O—$(C_{1-3})$alkyl, —S—$(C_{1-3})$alkyl, —SO—$(C_{1-3})$alkyl and —SO$_2$—$(C_{1-3})$alkyl are each optionally substituted with one, two or three halo substituents;
$R^3$ is cyclopentyl or cyclohexyl, each being optionally substituted with one to four fluoro substituents;
$R^5$ is selected from $(C_{1-6})$alkyl, $(C_{2-6})$alkenyl, $(C_{2-6})$alkynyl, $(C_{3-7})$cycloalkyl, $(C_{3-7})$cycloalkyl-$(C_{1-6})$alkyl-, Het and Het-$(C_{1-6})$alkyl-; wherein the Het and the Het portion of the Het-$(C_{1-6})$alkyl- are each selected from a 5- or 6-membered saturated, unsaturated or aromatic monocyclic heterocycle, having one to three heteroatoms each independently selected from N, O and S; and
wherein the $(C_{1-6})$alkyl is optionally substituted with from one to three substituents each independently selected from halo, cyano, $(C_{1-6})$alkoxy, —NH$(C_{1-6})$ alkyl, —N((C$_{1-6}$)alkyl)$_2$ and —NHSO$_2$(C$_{1-6}$)alkyl; and wherein each of the Het and the Het portion of the Het-(C$_{1-6}$)alkyl- is optionally substituted with (C$_{1-6}$)alkyl; and R$^6$ is H, methyl, ethyl or fluoro; or R$^5$ and R$^6$ are linked such that the group of the subformula

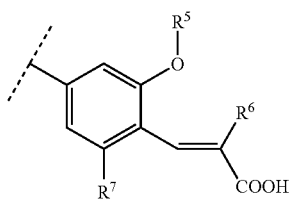

is a group of formula

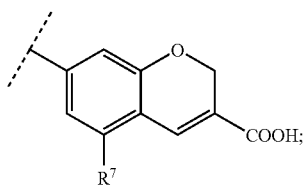

R$^7$ is H, methyl, ethyl, methoxy or ethoxy; and

R$^9$ and R$^{10}$ are each independently selected from (C$_{1-3}$) alkyl or R$^9$ and R$^{10}$ are covalently bonded together to form (C$_{3-6}$)cycloalkyl, (C$_{5-6}$)cycloalkenyl or a 5- or 6-membered heterocycle having from 1 to 2 heteroatoms each independently selected from O and N; wherein the cycloalkyl, cycloalkenyl and heterocycle are each optionally substituted with (C$_{1-4}$)alkyl.

24. The compound according to claim 1 wherein:

R$^1$ is H or methyl;

R$^2$ is phenyl or Het, wherein Het is selected from

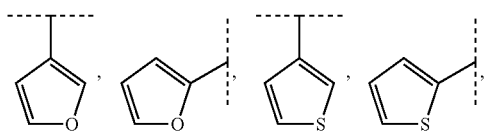

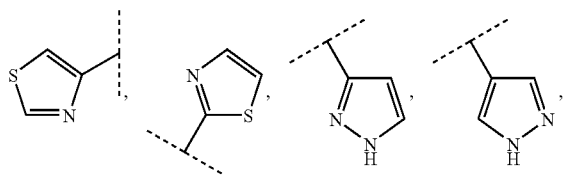

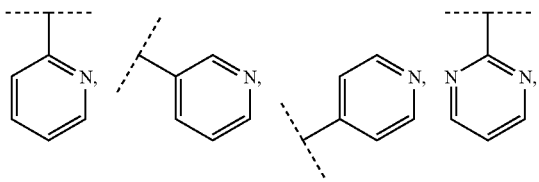

-continued

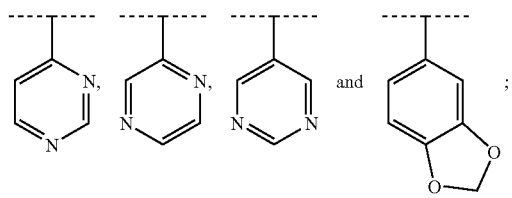

wherein R$^2$ is unsubstituted or substituted with R$^{21}$, wherein

R$^{21}$ is one, two or three substituents each independently selected from fluoro, chloro, bromo, methyl, ethyl, propyl, 1-methylethyl, trifluoromethyl, cyclopropyl, cyclobutyl, cyclopentyl, cyclohexyl, methoxy, ethoxy, propoxy, 1-methylethoxy, methylthio, ethylthio, propylthio, 1-methylethylthio, amino, N-methylamino, N,N-dimethylamino, —SO$_2$CH$_3$ and cyano;

R$^3$ is cyclopentyl or cyclohexyl, each optionally substituted with one to four fluoro substituents;

R$^5$ is selected from methyl, ethyl, propyl, 1-methylethyl, butyl, 1-methylpropyl, 2-methylpropyl, 1,1-dimethylethyl, 2-propenyl, 2-propynyl, cyclopropyl, cyclobutyl, cyclopropylmethyl, cyclobutylmethyl,

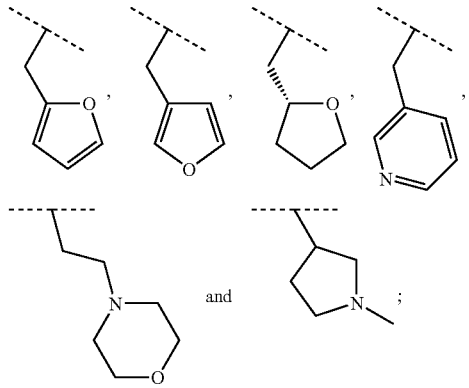

wherein the methyl, ethyl, propyl, 1-methylethyl, butyl, 1-methylpropyl, 2-methylpropyl and 1,1-dimethylethyl are each optionally substituted with from one to three substituents each independently selected from fluoro, methoxy, ethoxy, —N(CH$_3$)$_2$, and —NHSO$_2$CH$_3$;

R$^6$ is H, methyl, ethyl or fluoro;

R$^7$ is H or methoxy; and the group

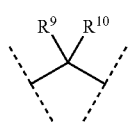

is selected from:

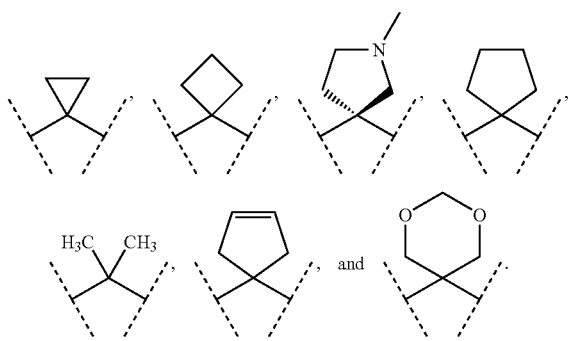

25. The compound according to claim 1 wherein:
$R^1$ is H or methyl;
$R^2$ is phenyl or Het, wherein Het is selected from

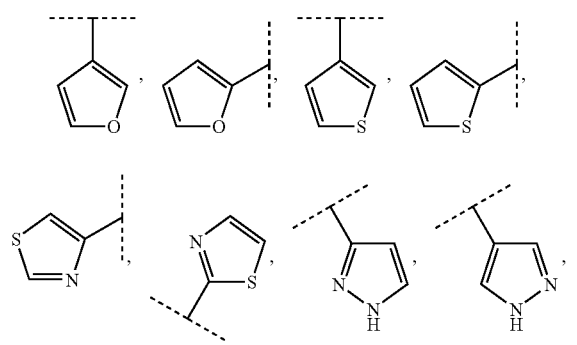

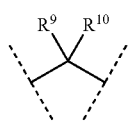

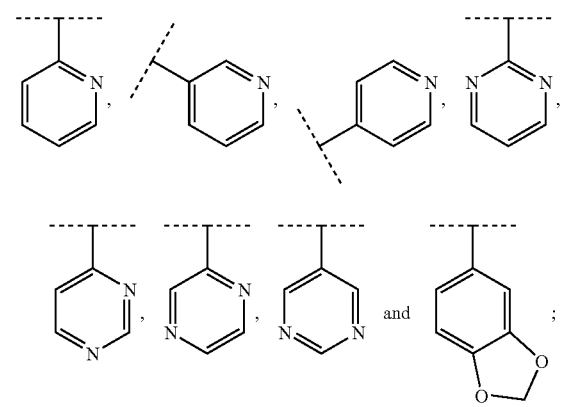

wherein $R^2$ is unsubstituted or substituted with $R^{2t}$, wherein
$R^{21}$ is one, two or three substituents each independently selected from fluoro, chloro, bromo, methyl, ethyl, propyl, 1-methylethyl, trifluoromethyl, cyclopropyl, cyclobutyl, cyclopentyl, cyclohexyl, methoxy, ethoxy, propoxy, 1-methylethoxy, methylthio, ethylthio, propylthio, 1-methylethylthio, amino, N-methylamino, N,N-dimethylamino, —SO$_2$CH$_3$ and cyano;
$R^3$ is cyclopentyl or cyclohexyl, each optionally substituted with one to four fluoro substituents;

$R^5$ and $R^6$ are linked, together with the atoms to which they are attached, to form a 6-membered ring, such that the group of the subformula

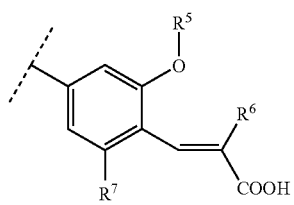

is a group of formula

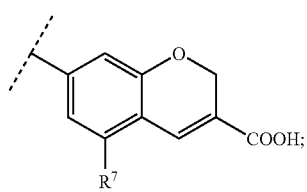

$R^7$ is H or methoxy; and
the group

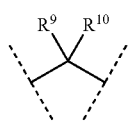

is selected from:

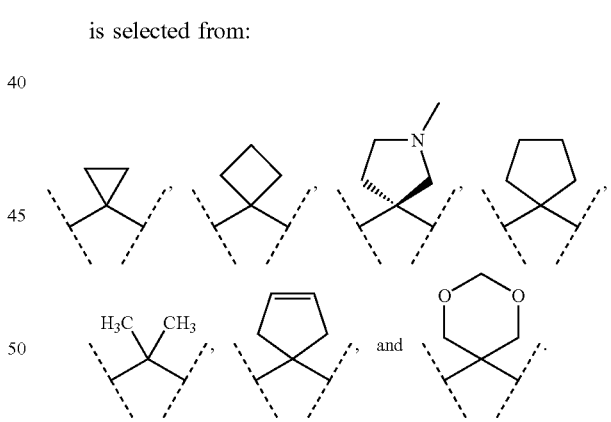

26. A compound of formula (I):

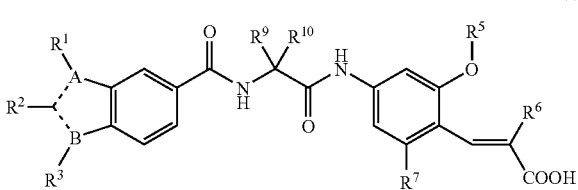

(I)

wherein:
either A or B is N and the other B or A is C, wherein—
between two C-atoms represents a double bond and—
between a C-atom and a N-atom represents a single bond;

$R^1$ is H or $(C_{1-6})$alkyl;

$R^2$ is $(C_{2-6})$alkynyl, —C(=O)—$(C_{1-6})$alkyl, aryl or Het; the aryl and Het being optionally substituted with $R^{21}$;
wherein $R^{21}$ is one, two or three substituents each independently selected from $(C_{1-6})$alkyl, $(C_{3-7})$cycloalkyl, Het, —CN, —NH$_2$, —NH$(C_{1-6})$alkyl, —N($(C_{1-6})$alkyl)$_2$, halo, —O—$(C_{1-6})$alkyl, —S—$(C_{1-6})$alkyl, —SO—$(C_{1-6})$alkyl and —SO$_2$—$(C_{1-6})$alkyl;
wherein the $(C_{1-6})$alkyl, —O—$(C_{1-6})$alkyl, —S—$(C_{1-6})$alkyl, —SO—$(C_{1-6})$alkyl and —SO$_2$—$(C_{1-6})$alkyl are each optionally substituted with one, two or three halo substituents;

$R^3$ is $(C_{5-6})$cycloalkyl, optionally substituted with from one to four halo substituents;

$R^5$ is selected from H, $(C_{1-6})$alkyl, $(C_{2-6})$alkenyl, $(C_{2-6})$alkynyl, $(C_{3-7})$cycloalkyl, and $(C_{3-7})$cycloalkyl-$(C_{1-6})$alkyl-;
wherein the $(C_{1-6})$alkyl is optionally substituted with from one to three substituents each independently selected from halo, cyano and $(C_{1-6})$alkoxy; and $R^6$ is selected from H, $(C_{1-6})$alkyl and halo; or $R^5$ and $R^6$ are linked, together with the atoms to which they are attached, to form a 5-, 6- or 7-membered ring;

$R^7$ is selected from H, $(C_{1-6})$alkyl, $(C_{1-6})$alkoxy, $(C_{1-6})$alkylthio, —NH$_2$, —NH$(C_{1-6})$alkyl, —N($(C_{1-6})$alkyl)$_2$ and halo;

$R^9$ and $R^{10}$ are each independently selected from $(C_{1-6})$alkyl; or $R^9$ and $R^{10}$ are covalently bonded together to form $(C_{3-7})$cycloalkyl, $(C_{5-7})$cycloalkenyl or a 4-, 5- or 6-membered heterocycle having from 1 to 3 heteroatoms each independently selected from O, N, and S; wherein the cycloalkyl, cycloalkenyl or heterocycle are each optionally substituted with $(C_{1-4})$alkyl;

wherein Het is defined as a 3- to 7-membered heterocycle having 1 to 4 heteroatoms each independently selected from O, N and S, which may be saturated, unsaturated or aromatic, and which is optionally fused to at least one other cycle to form a 4- to 14-membered heteropolycycle having wherever possible 1 to 5 heteroatoms, each independently selected from O, N and S, the heteropolycycle being saturated, unsaturated or aromatic; or an enantiomer, diastereoisomer or tautomer thereof, including a salt thereof.

27. A pharmaceutical composition comprising a therapeutically effective amount of a compound according to claim 1, or a pharmaceutically acceptable salt or ester thereof, and a pharmaceutically acceptable carrier.

28. The pharmaceutical composition according to claim 27 additionally comprising a therapeutically effective amount of one or more other antiviral agents.

29. A method of inhibiting the RNA-dependent RNA polymerase activity of the enzyme NS5B, encoded by HCV, comprising exposing the enzyme NS5B to an effective amount of a compound according to claim 1 under conditions where the RNA-dependent RNA polymerase activity of the enzyme NS5B is inhibited.

30. A method of inhibiting HCV replication, comprising exposing a cell infected with HCV to an effective amount of a compound according to claim 1 under conditions where replication of HCV is inhibited.

31. A method of treating HCV infection in a mammal, comprising administering to the mammal an effective amount of a compound according to claim 1, or a pharmaceutically acceptable salt or ester thereof.

32. A method of treating HCV infection in a mammal, comprising administering to the mammal an effective amount of a combination of a compound according to claim 1, or a pharmaceutically acceptable salt or ester thereof, and at least one other antiviral agent.

33. An article of manufacture comprising
a composition effective to treat an HCV infection; and
packaging material comprising a label which indicates that the composition can be used to treat infection by the hepatitis C virus,
wherein said composition comprises a compound according to claim 1 or a pharmaceutically acceptable salt or ester thereof.

* * * * *